US011517355B2

(12) United States Patent
Smisson, III et al.

(10) Patent No.: US 11,517,355 B2
(45) Date of Patent: Dec. 6, 2022

(54) INTERSPINOUS PROCESS SPACING DEVICE

(71) Applicant: Southern Spine, LLC, Macon, GA (US)

(72) Inventors: Hugh F. Smisson, III, Macon, GA (US); David C. Field, Snellville, GA (US); Brandi L. Bohleber, Macon, GA (US); Hiywot Yilma, Atlanta, GA (US); Michael A. Cowan, Charlotte, NC (US)

(73) Assignee: Southern Spine, LLC, Macon, GA (US)

( * ) Notice: Subject to any disclaimer, the term of this patent is extended or adjusted under 35 U.S.C. 154(b) by 81 days.

(21) Appl. No.: 17/016,524

(22) Filed: Sep. 10, 2020

(65) Prior Publication Data

US 2021/0204986 A1    Jul. 8, 2021

Related U.S. Application Data

(63) Continuation of application No. 16/036,329, filed on Jul. 16, 2018, now Pat. No. 10,792,078, which is a
(Continued)

(51) Int. Cl.
*A61B 17/70* (2006.01)
*A61B 90/00* (2016.01)
*A61B 17/86* (2006.01)

(52) U.S. Cl.
CPC ...... *A61B 17/7068* (2013.01); *A61B 17/7055* (2013.01); *A61B 17/7062* (2013.01);
(Continued)

(58) Field of Classification Search
CPC ........................................ A61B 17/7062–7071
See application file for complete search history.

(56) References Cited

U.S. PATENT DOCUMENTS

| 5,645,599 A | 7/1997 | Samani |
| 5,702,453 A | 12/1997 | Rabbe et al. |

(Continued)

FOREIGN PATENT DOCUMENTS

| CN | 101129271 A | 2/2008 |
| KR | 101030462 B1 | 4/2011 |

(Continued)

OTHER PUBLICATIONS

PCT International Search Report for PCT/US2011/028365, dated Nov. 30, 2011.
(Continued)

*Primary Examiner* — Eduardo C Robert
*Assistant Examiner* — Steven J Cotroneo
(74) *Attorney, Agent, or Firm* — Eversheds Sutherland (US) LLP

(57) ABSTRACT

Interspinous process spacing devices and associated methods are provided. In one embodiment, an interspinous process spacing device includes a first attachment side, a second attachment side, and a spacer. The first attachment side and the second attachment side each include a central portion, a first wing portion, and a second wing portion. The central portion includes an inner surface extending along at least a majority of an anterior-posterior height of the central portion, and the first wing portion includes an inner surface extending along at least a majority of an anterior-posterior height of the first wing portion. The inner surface of the first wing portion extends in a direction transverse to the inner surface of the central portion, and the anterior-posterior height of the first wing portion is less than the anterior-posterior height of the central portion.

19 Claims, 38 Drawing Sheets

Related U.S. Application Data continuation of application No. 15/339,216, filed on Oct. 31, 2016, now Pat. No. 10,022,162, which is a continuation of application No. 14/069,832, filed on Nov. 1, 2013, now Pat. No. 9,561,061, which is a continuation of application No. 13/047,472, filed on Mar. 14, 2011, now Pat. No. 8,591,547.

(60) Provisional application No. 61/313,169, filed on Mar. 12, 2010.

(52) U.S. Cl.
CPC ...... *A61B 17/7067* (2013.01); *A61B 17/7076* (2013.01); *A61B 17/86* (2013.01); *A61B 90/06* (2016.02); *A61B 2090/061* (2016.02)

(56) References Cited

U.S. PATENT DOCUMENTS

| | | | |
|---|---|---|---|
| 6,364,883 B1* | 4/2002 | Santilli | A61B 17/7068 606/279 |
| 7,048,736 B2 | 5/2006 | Robinson et al. | |
| 7,189,234 B2 | 3/2007 | Zucherman et al. | |
| 7,727,233 B2 | 6/2010 | Blackwell et al. | |
| 7,871,426 B2 | 1/2011 | Chin et al. | |
| 7,981,875 B2 | 4/2011 | Lins et al. | |
| 8,206,420 B2 | 6/2012 | Patel et al. | |
| 8,241,330 B2 | 8/2012 | Lamborne et al. | |
| 8,262,697 B2 | 9/2012 | Kirschman | |
| 8,343,190 B1 | 1/2013 | Mueller et al. | |
| 8,636,771 B2 | 1/2014 | Butler et al. | |
| 8,882,805 B1 | 11/2014 | Maccree | |
| 9,192,414 B2 | 11/2015 | Haas et al. | |
| 9,585,699 B2 | 3/2017 | Robinson | |
| 9,622,793 B1 | 4/2017 | Ponmudi et al. | |
| 9,724,136 B2 | 8/2017 | Taber et al. | |
| 9,737,344 B2 | 8/2017 | Stern et al. | |
| 9,743,960 B2 | 8/2017 | Lamborne et al. | |
| 9,750,544 B2 | 9/2017 | Taber et al. | |
| 2003/0040746 A1 | 2/2003 | Mitchell et al. | |
| 2003/0216736 A1 | 11/2003 | Robinson et al. | |
| 2006/0015181 A1 | 1/2006 | Elberg | |
| 2006/0064165 A1 | 3/2006 | Zucherman et al. | |
| 2006/0089654 A1 | 4/2006 | Lins et al. | |
| 2006/0247634 A1 | 11/2006 | Warner et al. | |
| 2006/0247640 A1 | 11/2006 | Blackwell et al. | |
| 2007/0233082 A1 | 10/2007 | Chin et al. | |
| 2007/0276493 A1 | 11/2007 | Malandain et al. | |
| 2008/0033556 A1 | 2/2008 | Le Couedic et al. | |
| 2008/0082172 A1 | 4/2008 | Jackson | |
| 2008/0140125 A1* | 6/2008 | Mitchell | A61B 17/1671 606/279 |
| 2008/0177306 A1 | 7/2008 | Lamborne et al. | |
| 2008/0183211 A1* | 7/2008 | Lamborne | A61B 17/7061 606/248 |
| 2008/0183218 A1 | 7/2008 | Mueller et al. | |
| 2008/0221692 A1 | 9/2008 | Zucherman et al. | |
| 2008/0281359 A1 | 11/2008 | Abdou | |
| 2008/0281423 A1* | 11/2008 | Sheffer | A61B 17/7062 623/17.11 |
| 2008/0294199 A1 | 11/2008 | Kohm et al. | |
| 2008/0300686 A1 | 12/2008 | Khoo | |
| 2009/0062915 A1 | 3/2009 | Kohm et al. | |
| 2009/0264927 A1* | 10/2009 | Ginsberg | A61B 17/7068 606/279 |
| 2010/0036419 A1* | 2/2010 | Patel | A61B 17/7068 606/279 |
| 2010/0087860 A1 | 4/2010 | Chin et al. | |
| 2010/0211101 A1 | 8/2010 | Blackwell et al. | |
| 2010/0241167 A1 | 9/2010 | Taber et al. | |
| 2011/0022090 A1* | 1/2011 | Gordon | A61B 17/7068 606/248 |
| 2011/0054531 A1 | 3/2011 | Lamborne et al. | |
| 2011/0066186 A1* | 3/2011 | Boyer, II | A61B 17/7065 606/249 |
| 2011/0118788 A1 | 5/2011 | Hochschuler et al. | |
| 2011/0144692 A1 | 6/2011 | Saladin et al. | |
| 2011/0166600 A1* | 7/2011 | Lamborne | A61B 17/7061 606/249 |
| 2011/0264221 A1 | 10/2011 | Woodward et al. | |
| 2012/0010660 A1 | 1/2012 | Fallin et al. | |
| 2012/0016418 A1 | 1/2012 | Chin et al. | |
| 2012/0059422 A1 | 3/2012 | Esce | |
| 2012/0089184 A1 | 4/2012 | Yeh | |
| 2012/0109203 A1 | 5/2012 | Dryer et al. | |
| 2012/0136390 A1 | 5/2012 | Butler et al. | |
| 2012/0150228 A1 | 6/2012 | Zappacosta et al. | |
| 2012/0221050 A1 | 8/2012 | Ingalhalikar et al. | |
| 2012/0221051 A1 | 8/2012 | Robinson | |
| 2012/0226312 A1 | 9/2012 | Thalgott et al. | |
| 2012/0226314 A1 | 9/2012 | Chin et al. | |
| 2012/0253396 A1 | 10/2012 | Stern et al. | |
| 2013/0072979 A1 | 3/2013 | Butler et al. | |
| 2013/0079880 A1 | 3/2013 | Wolters et al. | |
| 2013/0178904 A1 | 7/2013 | Arcenio et al. | |
| 2013/0184753 A1 | 7/2013 | Keiper et al. | |
| 2013/0184754 A1 | 7/2013 | Taber et al. | |
| 2013/0190820 A1 | 7/2013 | Siegfried et al. | |
| 2013/0197581 A1 | 8/2013 | Justis et al. | |
| 2013/0253585 A1 | 9/2013 | Garcia et al. | |
| 2013/0296940 A1 | 11/2013 | Northcutt et al. | |
| 2013/0304125 A1 | 11/2013 | Timm et al. | |
| 2014/0081331 A1 | 3/2014 | Zappacosta et al. | |
| 2014/0114355 A1 | 4/2014 | Robinson | |
| 2014/0128917 A1 | 5/2014 | Abdou | |
| 2014/0180297 A1 | 6/2014 | Jamshidi | |
| 2014/0188170 A1 | 7/2014 | Zappacosta et al. | |
| 2014/0207198 A1 | 7/2014 | Taber et al. | |
| 2014/0277143 A1 | 9/2014 | Zappacosta | |
| 2014/0371794 A1 | 12/2014 | Kirschman | |
| 2015/0066087 A1 | 3/2015 | Ingalhalikar et al. | |
| 2015/0265413 A1 | 9/2015 | Taber et al. | |
| 2015/0305785 A1 | 10/2015 | Taber et al. | |
| 2015/0313650 A1 | 11/2015 | Taber et al. | |
| 2015/0359640 A1 | 12/2015 | Taber et al. | |
| 2016/0228157 A1 | 8/2016 | Shoshtaev et al. | |
| 2017/0112547 A1 | 4/2017 | Lange et al. | |
| 2017/0143383 A1 | 5/2017 | Ingalhalikar et al. | |
| 2017/0181773 A1 | 6/2017 | Gustine et al. | |
| 2017/0189078 A1 | 7/2017 | Lamborne et al. | |
| 2017/0196598 A1 | 7/2017 | Mitchell et al. | |
| 2017/0215927 A1 | 8/2017 | Ponmudi et al. | |
| 2017/0333091 A1 | 11/2017 | Taber et al. | |

FOREIGN PATENT DOCUMENTS

| | | |
|---|---|---|
| WO | 2010019783 A2 | 2/2010 |
| WO | 2014159788 A1 | 10/2014 |

OTHER PUBLICATIONS

Extended European Search Report and Search Opinion for European Patent Application 11754250, dated Sep. 19, 2014.

* cited by examiner

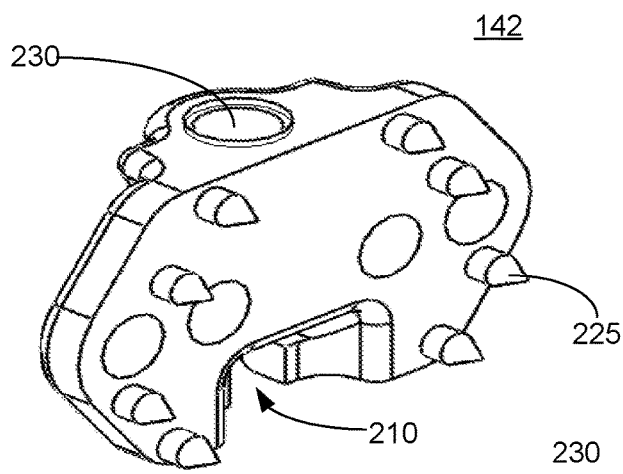
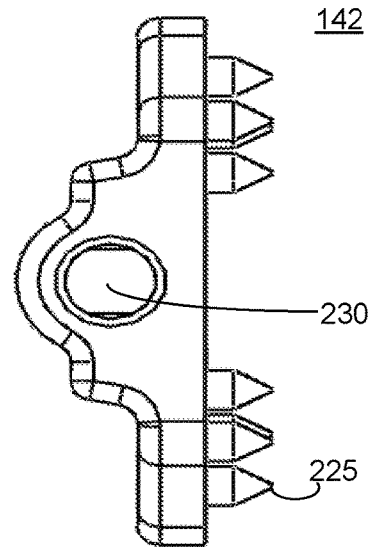
FIG. 2A
FIG. 2B
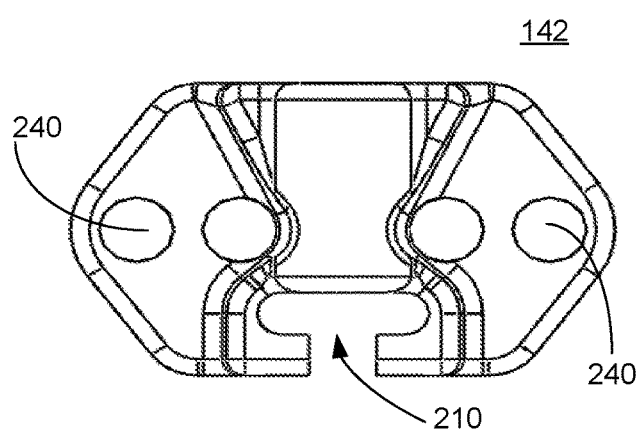
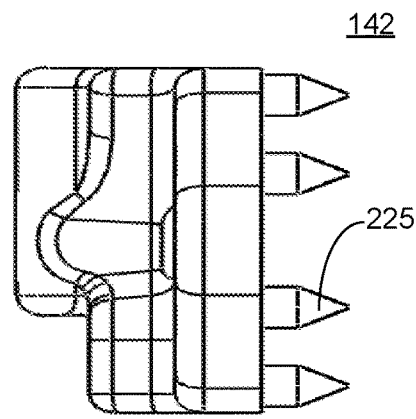
FIG. 2C
FIG. 2D

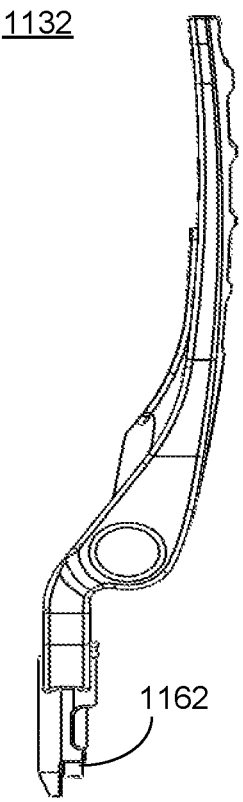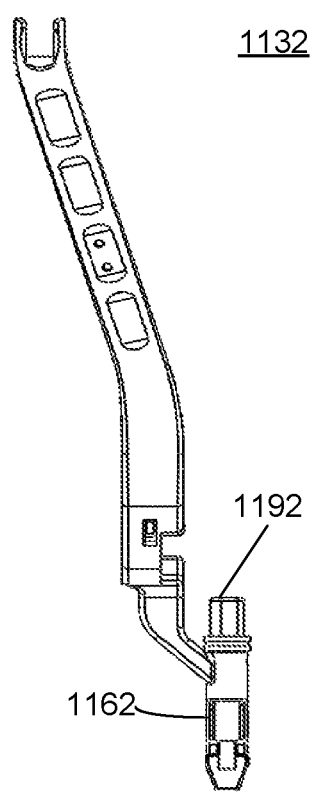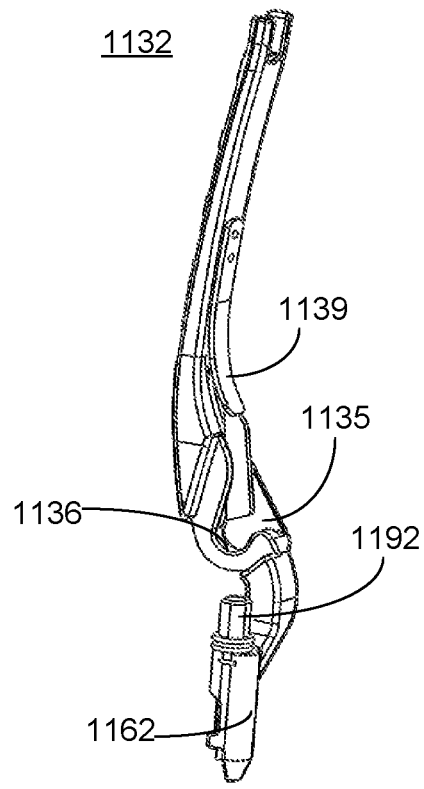
FIG. 14A
FIG. 14B
FIG. 14C

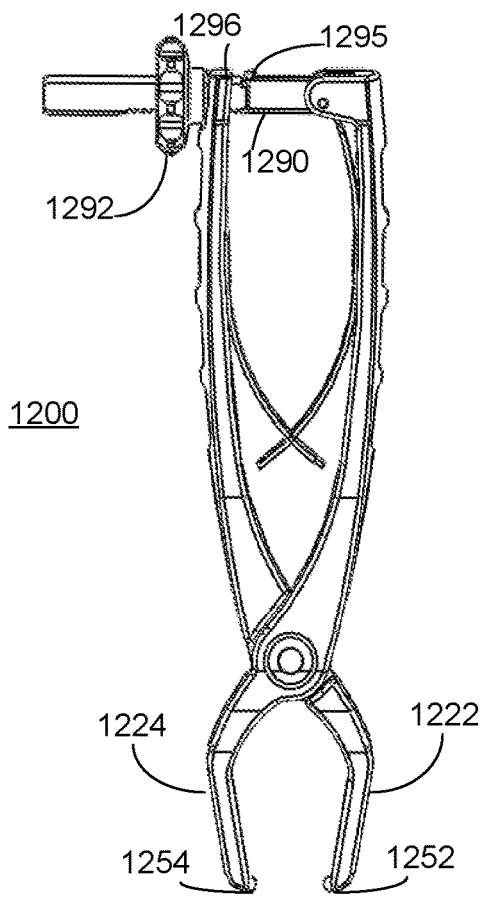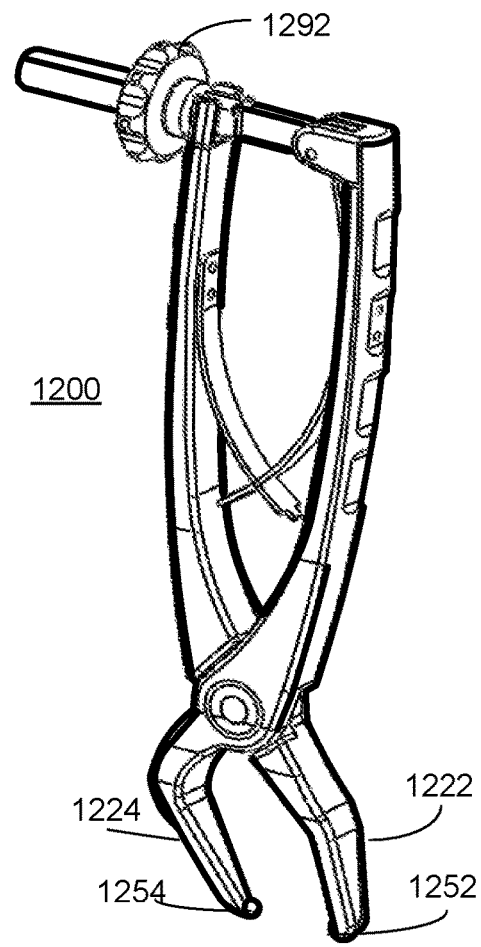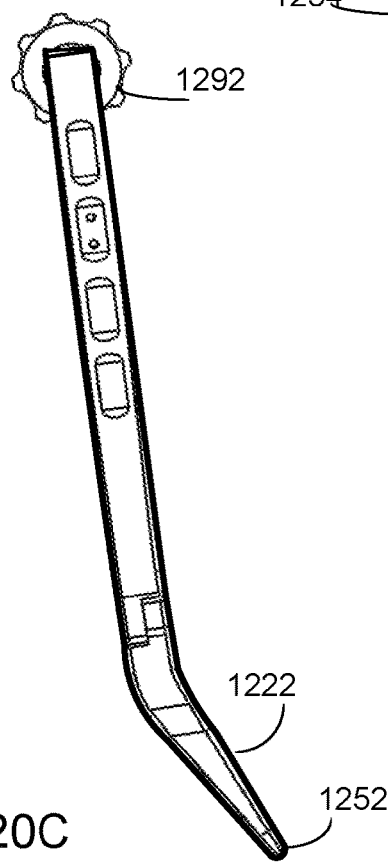
FIG. 20A
FIG. 20B
FIG. 20C

INTERSPINOUS PROCESS SPACING DEVICE

CROSS-REFERENCE TO RELATED APPLICATIONS

This application is a continuation of U.S. patent application Ser. No. 16/036,329, filed Jul. 16, 2018, which is a continuation of U.S. patent application Ser. No. 15/339,216, filed Oct. 31, 2016, now U.S. Pat. No. 10,022,162, which is a continuation of U.S. patent application Ser. No. 14/069,832, filed Nov. 1, 2013, now U.S. Pat. No. 9,561,061, which is a continuation of U.S. patent application Ser. No. 13/047,472, filed Mar. 14, 2011, now U.S. Pat. No. 8,591,547, issued Nov. 26, 2013, which claims priority to U.S. Provisional Patent Application Ser. No. 61/313,169 filed on Mar. 12, 2010, the entire contents of which are hereby incorporated by reference.

FIELD OF THE INVENTION

The invention relates generally to devices for use during spinal surgery, and methods pertaining thereto, and more particularly to devices and methods for providing spacing between adjacent spinous processes.

BACKGROUND OF THE INVENTION

Spinal discs and/or other vertebral changes can cause spinal disease that often leads to patient discomfort or even paralysis. For example, intervertebral spinal discs, which lie between adjacent vertebrae, can break down or degenerate, resulting in disc fluid loss and consequently resulting in a loss of disc flexibility. In addition, discs can become thinner, allowing the vertebrae to move closer together, may tear or crack in the outer layer and/or the annulus of the disc, and/or bulge outwardly. Facet joint degeneration may also lead to spinal disease. Physical trauma (e.g., accidents, injuries, strains, etc.) may cause spinal column changes, and spinal stenosis can cause the spinal canal to narrow due to excessive bone growth and/or thickening of tissue. In all of these conditions, the spinal canal through which the spinal cord and the spinal nerve roots pass may become narrowed, creating pressure on nerve tissue. Such pressure can cause pain, numbness, weakness, or even paralysis in various parts of the body.

Some methods for treating spinal diseases, such as those described above, limit the movement of adjacent vertebrae relative to one another to limit the additional pressure on the local nerve tissue by maintaining a minimum disc space and/or space surrounding the adjacent vertebrae. Various methods have been performed to maintain this minimum space, including disc implants and spinal fusions. One method includes implanting a spacer between two adjacent posteriorly extending spinous processes, which in effect maintains a maximum space between the corresponding vertebrae. Some existing spacer implant devices are implanted by affixing the device to adjacent spinous processes. Existing spacer implants, however, do not provide complete access to insert bone growth promoting substances into the spacer after implant. In addition, existing spacer implants do not provide structural integrity between two adjacently implanted spacers. Moreover, the procedures required to implant existing spacer implant devices are overly complicated, requiring the use of multiple tools to position, tighten, and secure the implants to the spinous processes.

Therefore, there remains a need for improved interspinous process spacer implants.

SUMMARY OF THE INVENTION

Various embodiments described herein provide devices and associated methods for treating spinal disease. According to one embodiment, an interspinous process spacing device is provided. The device includes a first attachment side and a second attachment side, whereby each attachment side includes one or more slots formed in the outer surface and oriented proximate one end for receiving fasteners extending inwardly from a second interspinous process spacing device. The device further includes a spacer tray positioned between the first attachment side and the second attachment side, the spacer tray extending in a substantially perpendicular orientation from the first attachment side and slideably insertable through a tray slot formed in the second attachment side, wherein the spacer tray is adapted to retain adjacent spinous processes in a spaced apart orientation. The device further includes securing means for securing the second attachment side relative to the first attachment side, wherein, upon securing the second attachment side relative to the first attachment side by the securing means, the interspinous process spacing device is engaged with the adjacent spinous processes.

In one aspect, the spacer tray comprises an arcuate cross-sectional shape and is substantially open and accessible from the posterior direction. The spacer tray is adapted to retain bone growth promoting substance and to maximize the open space above the spacer tray and between the spinous processes, wherein the bone growth promoting substance is packable after engaging the first attachment side and the second attachment side to adjacent spinous processes. In another embodiment, the spacer tray comprises two separate members forming a space therebetween.

According to one aspect, the securing means can include at least one of: (a) at least one worm drive assembly; (b) at least one rack and pinion assembly; (c) at least one screw extending between and operably connecting the first attachment side and the second attachment side; (d) a geared rack and ratchet assembly; or (e) at least one set screw assembly.

In one aspect, there are at least two spaced apart securing mechanisms extending between and operably connecting the first attachment side and the second attachment side, wherein each of the at least two spaced apart securing mechanisms can be independently and incrementally actuated causing each end of the attachment sides to engage the respective spinous process independently.

According to one aspect, the interspinous process spacing device is a first interspinous process spacing device, and a second interspinous process spacing device is included. The second interspinous process spacing device includes a first bent attachment side and a second bent attachment side, wherein each bent attachment side comprises a substantially flat end and an offset end adapted to overlap an adjacent portion of the respective attachment sides of the first interspinous process spacing device.

According to one aspect including a second interspinous process spacing device, each of the first attachment side and the second attachment side of the second interspinous process spacing device has one or more integration means for integrating and attaching the offset end of the second interspinous process spacing device with a portion of the respective attachment side of the first interspinous process spacing device.

According to various aspects, the first interspinous process spacing device may be implantable inferior or superior to the second interspinous process spacing device.

In a different embodiment, an interspinous process spacing system is provided. The interspinous process spacing system includes a first interspinous process spacing device and a second interspinous process spacing device. The interspinous process spacing device comprises two substantially flat attachment sides and a first spacer tray positioned therebetween, wherein one of the two substantially flat attachment sides is slideably positionable over the spacer tray. The second interspinous process spacing device comprises two bent attachment sides and a second spacer tray positioned therebetween, wherein each of the bent attachment sides comprises a substantially flat end and an offset end. After implantation of the first interspinous process spacing device on a first and a second adjacent spinous process, the offset ends of the two bent attachment sides of the second interspinous process spacing device at least partially overlap respective adjacent ends of the substantially flat attachment sides of the first interspinous process spacing device when implanting the second interspinous process spacing device on the second and a third spinous process adjacent to the second spinous process.

According to yet another embodiment, an interspinous process spacing device kit is provided. The interspinous process spacing device kit may include: a first interspinous process spacing device comprising a first attachment side and a second attachment side, the first and the second attachment sides of the first interspinous process spacing device having a substantially flat configuration; at least one additional interspinous process spacing device comprising a first attachment side and a second attachment side, the first and the second attachment sides of the at least one additional interspinous process spacing device having a bent configuration adapted to overlap a portion of a respective attachment side of the first interspinous process spacing device; and at least one insertion instrument adapted for retaining at least one of the first interspinous processing spacing devices or the at least one additional interspinous process spacing device and implanting the same.

The kit may include a first insertion instrument and a second insertion instrument, wherein the first insertion instrument is adapted for implanting at least one of the first interspinous process spacing devices or the at least one additional interspinous process spacing device in a first orientation, and the second insertion instrument is adapted for implanting at least one of the first interspinous processing spacing devices or the at least one additional interspinous process spacing device in a second orientation. Each insertion instrument may include a first arm and a second arm, wherein the second arm is removably and pivotally attachable to the first arm.

According to yet another embodiment, a method for implanting an interspinous process spacing device is provided.

According to yet another embodiment, a method for treating a spinal disorder including implanting one or more interspinous process spacing devices is provided.

According to yet another embodiment, a method for manufacturing an interspinous process spacing device is provided.

BRIEF DESCRIPTION OF THE DRAWINGS

The objects and advantages of the present invention will be better understood and more readily apparent when considered in conjunction with the following detailed description and accompanying drawings which illustrate, by way of example, embodiments of interspinous process spacing devices, and in which:

FIG. 2A is an isometric view of a second attachment side of an interspinous process spacing device, according to an example base plate embodiment. FIG. 2B is a top view of a second attachment side of an interspinous process spacing device, according to an example embodiment. FIG. 2C is a back view of a second attachment side of an interspinous process spacing device, according to an example embodiment. FIG. 2D is a side view of a second attachment side of an interspinous process spacing device, according to an example embodiment.

FIG. 4A is a top view of two interlinked interspinous process spacing devices. FIG. 4B is a top view of one secured interspinous process spacing base device and one unsecured interspinous process spacing link device. FIG. 4C is an isometeric view of one secured interspinous process spacing base device and one unsecured interspinous process spacing link device. FIG. 4D is a back (outside) view of a first attachment side of an interspinous process spacing device having a base plate fastened to a link plate device. FIG. 4E is a back view of a second attachment side of an interspinous process spacing device having a base plate fastened to a link plate device.

FIG. 14A is a side view of a first arm of a top down or universal surgical instrument for implanting and compressing/advancing two attachment sides of an interspinous process spacing device, according to an example embodiment. FIG. 14B is an alternative side view of a first arm of the example embodiment. FIG. 14C is an alternative side view of a first arm of the example embodiment.

FIG. 20A is a side view of a compressor tool for implanting an interspinous process spacing device, according to an example embodiment. FIG. 20B is an isometric view of a compressor tool for implanting an interspinous process spacing device, according to an example embodiment. FIG. 20C is an alternative side view of a compressor tool for implanting an interspinous process spacing device, according to an example embodiment.

DETAILED DESCRIPTION OF THE PREFERRED EMBODIMENTS

Figure 1:
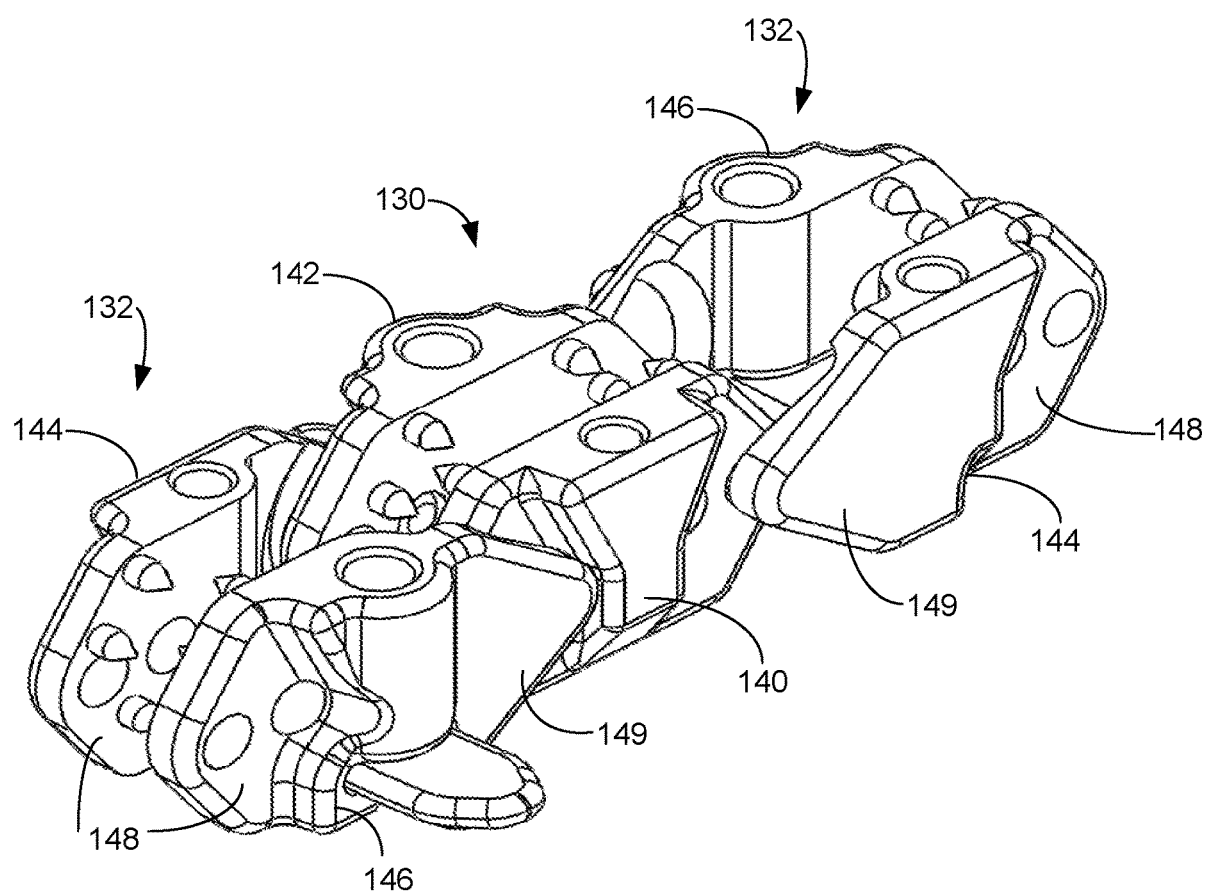
FIG. 1 is a profile view of three interspinous process spacing devices, according to an example embodiment.
Figure 2E:
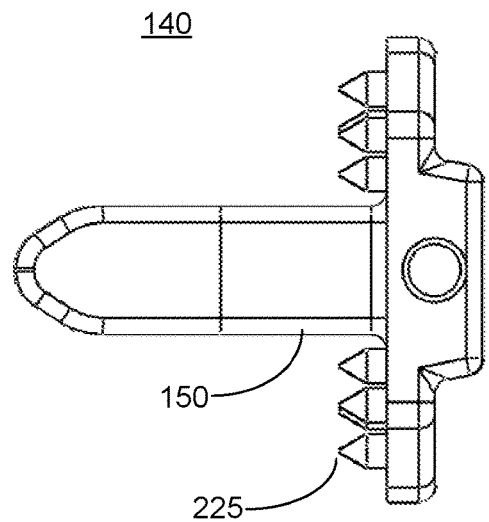
FIG. 2E is a top view a first attachment side of an interspinous process spacing device, according to an example embodiment.
Figure 2F:
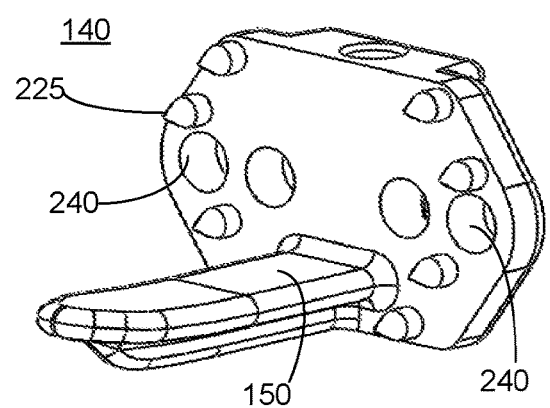
FIG. 2F is an isometric view of a first attachment side of an interspinous process spacing device, according to an example embodiment.
Figure 2G:
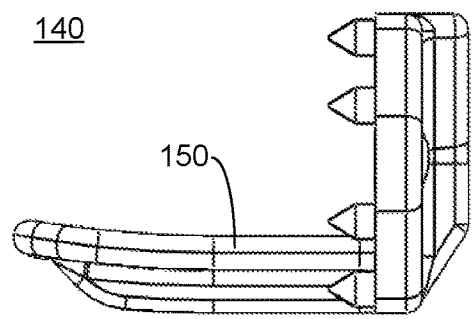
FIG. 2G is a side view of a first attachment side of an interspinous process spacing device, according to an example embodiment.
Figure 2H:
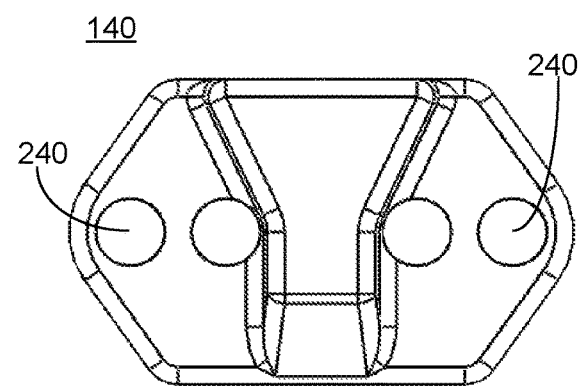
FIG. 2H is a back view of a first attachment side of an interspinous process spacing device, according to an example embodiment.
Figure 3A:
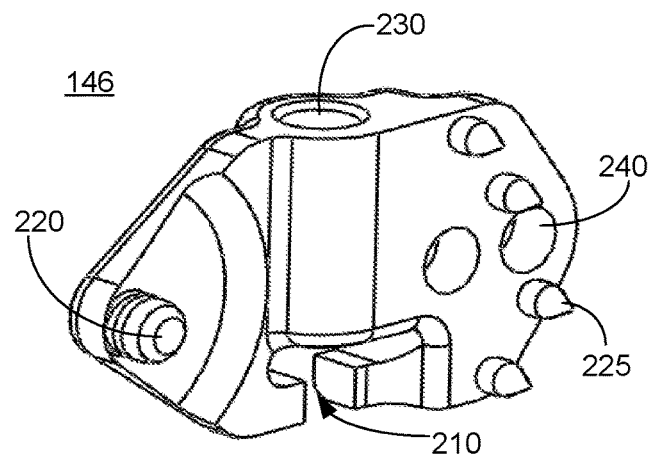
FIG. 3A is an isometric view of a second attachment side of an interspinous process spacing device, according to an example linker plate embodiment.
Figure 3B:
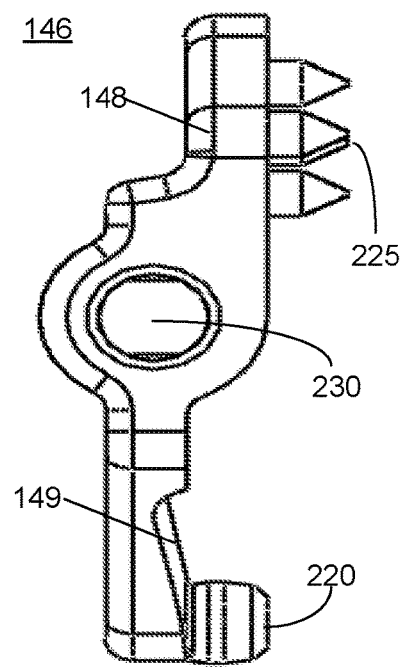
FIG. 3B is a top view of a second attachment side of an interspinous process spacing device, according to an example embodiment.
Figure 3C:
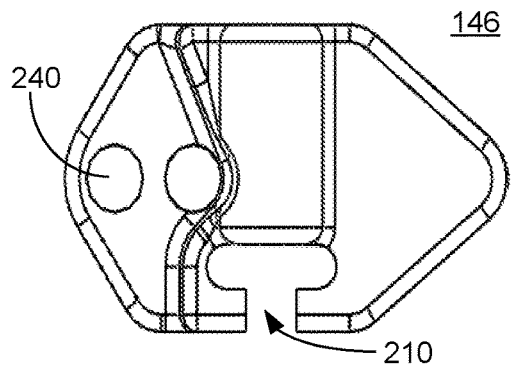
FIG. 3C is a back view of a second attachment side of an interspinous process spacing device, according to an example embodiment.
Figure 3D:
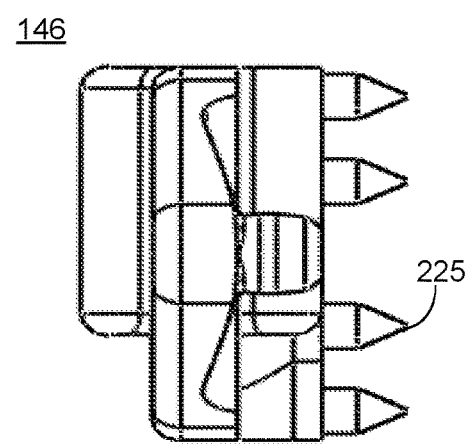
FIG. 3D is a side view of a second attachment side of an interspinous process spacing device, according to an example embodiment.
Figure 3E:
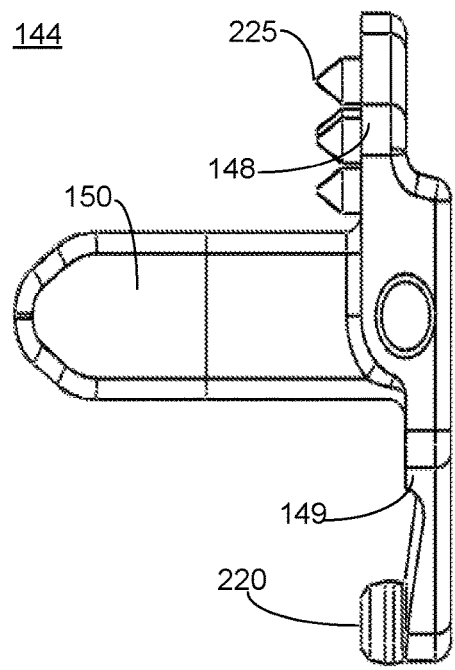
FIG. 3E is a top view a first attachment side of an interspinous process spacing device, according to an example embodiment.
Figure 3F:
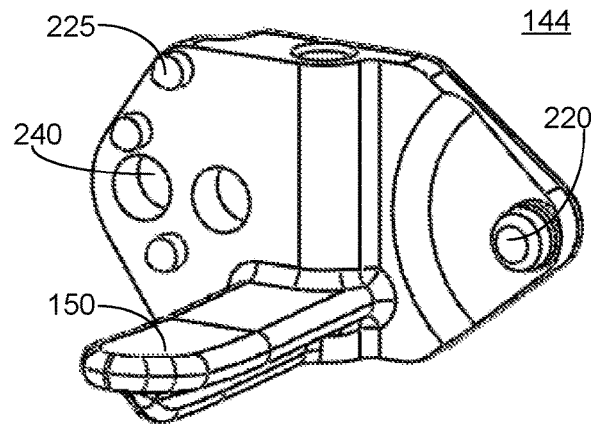
FIG. 3F is an isometric view of a first attachment side of an interspinous process spacing device, according to an example embodiment.
Figure 3G:
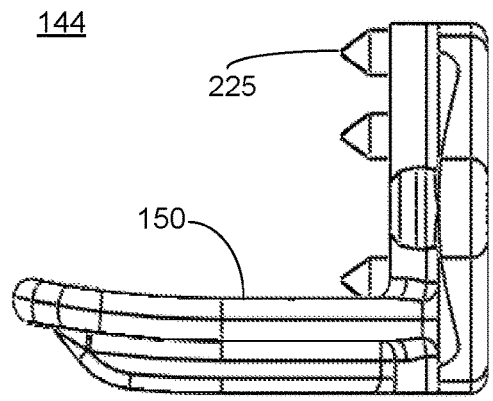
FIG. 3G is a side view of a first attachment side of an interspinous process spacing device, according to an example embodiment.
Figure 3H:
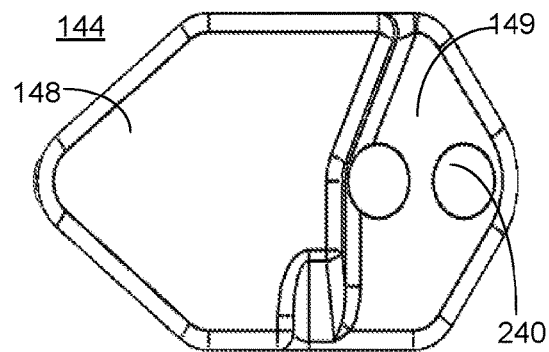
FIG. 3H is a back view of a first attachment side of an interspinous process spacing device, according to an example embodiment.

As required, detailed embodiments of the invention are disclosed herein. However, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the invention in virtually any appropriately detailed structure.

Embodiments of the invention provide interspinous process spacing devices and methods for their use and manufacture. As described above, an interspinous process spacing device provides a spacer inserted between posteriorly extending spinous processes of adjacent vertebrae to maintain minimum spacing between the spinous processes. Accordingly, a single interspinous process spacing device is designed to limit movement of only two adjacent vertebrae. According to certain embodiments described herein, an interspinous process spacing system is provided with at least two individual interspinous process spacing devices implantable in an integrated, overlapping configuration. This integrated and overlapping configuration improves the stability of the adjacent vertebrae since the two attachment sides are engaged with each other, thus increasing the surface area of each individual attachment side that can engage the surface of the respective spinous process, since the two attachment sides do not have to attach adjacent to each other, but overlapping such that one is attached to the top of the other. The invention provides that a single interspinous process spacing device of two attachment sides, also referred to as a pair of base plates, can be implanted alone having an integration mechanism, such as apertures therein, for future implantation of an overlapping second interspinous process spacing device of two attachment sides, also referred to as a pair of link plates.

According to one embodiment, a first interspinous process spacing device is implantable on two adjacent vertebrae by affixing to the spinous process of each vertebrae. A second interspinous process spacing device is implantable on the next adjacent vertebrae (e.g., in the superior or inferior direction) by affixing to the spinous process of the adjacent vertebrae and affixing to the adjacent end of the first interspinous process spacing device already implanted. According to one embodiment, to achieve this integrated configuration, the second (and succeeding) interspinous process spacing device has attachment sides in a bent configuration to overlap the attachment sides of the first interspinous process spacing device. The interspinous process spacing devices can include an integration mechanism, such as, but not limited to, a ball and socket arrangement or a pin and hole (aperture or slot) arrangement, or a pin and overlapping holes arrangement, or a hinge arrangement, or a bone engaging spike and hole arrangement for securely overlapping attachment sides of a first and second interspinous process spacing device and, in the case of a spiked integration mechanism, further engaging the spinous process. In various embodiments, the integration mechanism may allow for overlapping attachment sides of first and second interspinous process spacing devices without requiring a bent configuration of the attachment sides, as further described below.

Each of the interspinous process spacing devices includes a first attachment side and a second attachment side in an approximately parallel orientation relative to each other. Each of the attachment sides aligns and selectively engages a respective side of two adjacent spinous processes to retain the implant in position. Thus, the attachment sides are adjustable in a substantially perpendicular direction relative to their orientation (e.g., along the axis of the spacer tray extending between them) to permit closing and tightening them on the spinous process sandwiched therebetween. In one embodiment, the inner surfaces of each of the attachment sides include multiple fasteners (e.g., teeth, barbs, hooks, spikes, or any other gripping surface or other suitable attachment means) protruding therefrom, which interface with the surfaces of the spinous processes to facilitate attaching the attachment sides thereto. In one example, the fasteners can be positioned at or near the edges and/or corners of each attachment side to align with the spinous processes during implantation.

In one embodiment in which multiple interspinous process spacing devices are intended to be used to fasten to more than two adjacent vertebrae, the attachment sides of the first interspinous process spacing device have a substantially flat configuration, whereas the attachment sides of the second (and any subsequent) interspinous process spacing device are formed in a bent configuration, such that a portion of each attachment side is offset from the remaining portion of the attachment side to permit overlapping the first interspinous process spacing device during implantation. As such, the offset portion is set out a distance approximately equal to, or slightly larger or smaller than, the thickness of the attachment side. To improve securing the second interspinous process spacing device to the first, the outer surfaces of the attachment sides of the first interspinous process spacing device may include apertures (e.g., holes, slots, etc.) oriented to receive fasteners extending from the inner surfaces of the offset portion of the attachment sides of the second interspinous process spacing device where the two overlap. Inserting some of the fasteners of the second interspinous process spacing device into the first device increases the purchase and stability of the two devices together, improving the effectiveness of the implant. In other embodiments, however, other means for allowing an overlapping arrangement of multiple interspinous process spacing devices can be used.

In addition, according to various embodiments described herein, the interspinous process spacing devices include an improved spacer tray configured to permit increased access and provide an increased area for bone growth above the spacer tray and between the spinous processes after implant. Access to the tray space and maximized open space between the spinous processes after implant is beneficial when providing a bone growth promoting substance to fuse the spinous processes above the spacer tray. The amount and orientation of the bone material can have direct consequences on its ability to promote bone and other tissue in-growth, further strengthening the implant and its fixation to the vertebrae. By orienting the spacer tray such that it will be positioned proximate the vertebrae when implanted, bone and other tissue in-growth is improved by increasing the surface area, and the amount and proximity of the bone growth promoting substance to the vertebrae and other tissue. The spacer tray can vary in length, width and in rotatable position about an axis defined by its length.

As described, at least one attachment side of each interspinous process spacing device is configured to slide along the spacer tray to allow closing the attachment sides on the adjacent spinous processes. Each interspinous process spacing device further includes securing means to secure the attachment sides in position upon engaging the spinous processes. The securing means may vary according to different embodiments, which include, but are not limited to, worm drive mechanisms, gear and pinion mechanisms, ratchet and gear mechanisms (like a lock tie or cable tie), cam mechanisms, one or two spaced apart screws connecting the two attachment sides, any variation of the aforementioned mechanisms with only a single or multiple screw/gear/ratchet mechanisms, etc., one or more set screws, a separate clamping means combined with a set screw, or any combination thereof.

Embodiments that have at least two spaced apart securing mechanisms allow tightening each side of the interspinous process spacing device independently. As such, the attachment sides can be tightened using a "walking" approach by alternating between incremental actuations of each mechanism. Tightening each side of the interspinous process spacing device independently allows the attachment sides to close on the adjacent spinous processes in a more tight and secure configuration irrespective of varied thicknesses or shapes of the spinous processes. Otherwise, without providing independent variability when tightening each end of the attachment sides, the interspinous process spacing device may not as securely engage adjacent spinous processes having varied thicknesses. Moreover, the two spaced apart securing mechanisms may optionally avoid having to use a separate clamping and/or insertion instrument to secure the interspinous process spacing device to the spinous processes, which is required by prior devices to achieve tight fixation. However, in some embodiments described below, one may opt to use an additional insertion instrument, which may be used to provide the initial orientation and attachment or clamping of an interspinous process spacing device to the spinous processes, while the interspinous process spacing device and its integrated securing means may be used to achieve final fixation and secure engagement to the spinous processes. However, other securing mechanisms described herein that do not include two spaced apart mechanisms provide the additional advantages of a single device for securing and the unique application of mechanical securing components that tighten the two attachment sides, which simplifies the implantation procedure.

The present invention provides an interspinous process spacing device, comprising a first attachment side and a second attachment side, each attachment side comprising one or more slots formed therein and oriented proximate one end for receiving fasteners extending inwardly from a second interspinous process spacing device. The interspinous process spacing device further comprises a spacer tray positioned between the first attachment side and the second attachment side, the spacer tray extending from the first attachment side and slideably insertable through a spacer tray slot formed in the second attachment side, wherein the spacer tray is adapted to retain adjacent spinous processes in a spaced apart orientation. The interspinous process spacing device further comprises securing means for securing the second attachment side relative to the first attachment side, wherein, upon securing the second attachment side relative to the first attachment side by the securing means, the interspinous process spacing device is engaged with the adjacent spinous processes. In certain embodiments of the interspinous process spacing device, the one or more slots for receiving fasteners from a second interspinous process spacing device are oriented proximate each end of the first attachment side and the second attachment side. In certain embodiments of the interspinous process spacing device, the one or more bone fasteners extend inwardly on one end of the first attachment side and the second attachment side. In certain embodiments of the interspinous process spacing device, the one or more bone fasteners extend inwardly on each end of the first attachment side and the second attachment side.

In certain embodiments of the interspinous process spacing device, each attachment side has a central portion and two wing portions extending in opposite directions from the central portion, and the one or more bone fasteners and the one or more slots for receiving extension fasteners from a second interspinous process spacing device are located on at least one wing portion. In certain embodiments of the interspinous process spacing device, each wing portion has more than one slot for receiving extension fasteners from a second interspinous process spacing device. In certain embodiments of the interspinous process spacing device, one wing portion of the first and second attachment sides has one extension fastener extending inwardly for attaching to another interspinous process spacing device.

In certain embodiments of the interspinous process spacing device, the means for securing the second attachment side relative to the first attachment side is a bearing screw extending posteriorly through a central portion of second attachment side to the tray slot. In certain embodiments of the interspinous process spacing device, the tray slot engages the spacer tray with freedom of movement to permit at least 20 degrees of lateral rotation of the second attachment side relative to the first attachment side prior to engaging the securing means.

In certain embodiments of the interspinous process spacing device, the spacer tray comprises a T-shaped cross-section, and the tray slot in the second attachment side has a reciprocating T-shape. In certain embodiments of the interspinous process spacing device, the bottom of the T-shape is medially disposed from the first attachment side, and the cross-sectional shape tapers to a point on the spacer tray to facilitate insertion of the tray through the ligament and angled insertion of the tray through the tray slot in the second attachment side.

In certain embodiments of the interspinous process spacing device, the spacer tray has an arcuate longitudinal shape, such that the spacer tray extends in a posterior curvature to facilitate angled insertion through ligaments and into the tray slot. In certain embodiments, at least the end portion of the spacer tray extends in an arcuate shape corresponding to the arc created when the sides are attached to a pivoting insertion tool and are drawn together, as described in more detail below. In certain embodiments of the interspinous process spacing device, the spacer tray extends perpendicularly before the posterior curvature to facilitate angled insertion through the tray slot.

In certain embodiments of the interspinous process spacing device, the spacer tray comprises an arcuate cross-sectional shape such that upon implanting, the spacer tray is posteriorly open and accessible. In certain embodiments of the interspinous process spacing device, the spacer tray is adapted to retain bone growth promoting substance, wherein the bone growth promoting substance is packable after engaging the first attachment side and the second attachment side to adjacent spinous processes.

In certain embodiments of the interspinous process spacing device, the securing means for securing the second attachment side relative to the first attachment side is at least one set screw extending through the central portion from the posterior orientation to the tray slot to secure the second attachment side to the spacer tray in a substantially fixed position. In various embodiments, the securing means comprises at least one of: (a) at least one worm drive assembly; (b) at least one rack and pinion assembly; (c) at least one screw extending between and operably connecting the first attachment side and the second attachment side; (d) a geared rack and ratchet assembly; or (e) at least one set screw assembly.

In certain embodiments of the interspinous process spacing device, the securing means comprises at least two spaced apart securing mechanisms extending between and operably connecting the first attachment side and the second attachment side, wherein each of the at least two spaced apart securing mechanisms can be independently and incrementally actuated causing each end of the attachment sides to engage the respective spinous process independently.

In certain embodiments of the interspinous process spacing device, the first and second attachment side each have an insertion instrument receptacle posteriorily located on each attachment side. In certain embodiments of the interspinous process spacing device, the size, shape or indicia of the insertion instrument receptacle on the first attachment side is different from the size, shape or indicia of the implantation instrument receptacle on the second attachment side in order to facilitate connection to the correctly corresponding ends of the insertion instrument.

In certain embodiments, the interspinous process spacing device is a first interspinous process spacing device (or pair of base plates), and further comprising a second interspinous process spacing device (or pair of link plates) comprising a first offset attachment side and a second offset attachment side, wherein each offset attachment side comprises a substantially flat end and an offset end adapted to overlap over an adjacent portion of respective attachment sides of the first interspinous process spacing device and having fasteners extending inwardly therefrom receivable into the slots in each attachment side of the first interspinous process spacing device.

In certain embodiments of the interspinous process spacing device, the substantially flat end further comprises one or more bone fasteners extending inwardly and one or more slots formed therein for receiving fasteners extending inwardly from a third interspinous process spacing device. In certain embodiments of the interspinous process spacing device, the first attachment side and the second attachment side of the second interspinous process spacing device each have an integration means for integrating and attaching the offset end of the second interspinous process spacing device with a portion of the respective attachment side of the first interspinous process spacing device.

In certain embodiments of the interspinous process spacing device, the integration means comprise fasteners extending inwardly from the second interspinous process spacing device which pivotally engage the one or more slots formed in each attachment side of the first interspinous process spacing device, such that the second interspinous process spacing device can pivot through a 155 degree angle with respect to the first interspinous process spacing device. In certain embodiments of the interspinous process spacing device, the second interspinous process spacing device can pivot through a 120 degree angle with respect to the first interspinous process spacing device. In certain embodiments of the interspinous process spacing device, the second interspinous process spacing device can pivot posteriorly and anteriorly through substantially equal degrees with respect to the first interspinous process spacing device.

In certain embodiments of the interspinous process spacing device, the integration means comprises at least one of: (a) one or more fasteners extending from the inner surfaces of the offset end and receivable by the one or more apertures formed in the respective attachment side of the first interspinous process spacing device; (b) at least one pin extending from the inner surfaces of the offset end and receivable by the one or more apertures formed in the respective attachment side of the first interspinous process spacing device; (c) a domed surface extending from the inner surface of the offset end and receivable by a dome-shaped recess formed in the respective attachment side of the first interspinous process spacing device; (d) a textured surface formed on the inner surface of the offset end and mateable to a textured surface formed on the outer surface of the respective attachment side of the first interspinous process spacing device; or (e) a textured domed surface extending from the inner surface of the offset end and receivable by a complementarily-shaped textured recess formed in the respective attachment side of the first interspinous process spacing device.

In certain embodiments of the interspinous process spacing device, the offset ends of the second interspinous process spacing device are offset by a distance approximately equal to the thickness of the respective attachment side of the first interspinous process spacing device. In certain embodiments of the interspinous process spacing device, the first interspinous process spacing device is implantable at an inferior position relative to the second interspinous process spacing device. In certain embodiments of the interspinous process spacing device, the first interspinous process spacing device is implantable at a superior position relative to the second interspinous process spacing device.

In certain embodiments, the interspinous process spacing device is configured for implantation at the L5-S1 vertebrae and comprising a first angled attachment side and a second angled attachment side, wherein each angled attachment side comprises an angled end adapted to accommodate a sacrum. In certain embodiments, the first and second angled attachment sides are each selectively adjustable for optimizing the angle to fit the particular patient's sacrum anatomy and then securing the selected angle. The ends opposite the angled sacrum attachment ends can have bone fasteners extending from the inner surfaces thereof and one or more apertures therethrough, allowing the device to serve as a base plate for receiving fasteners on a second superiorly located spacing device. Alternatively, the ends opposite the angled sacrum attachment ends can be offset and each have a fastener (such as a bone fastening spike) extending from the inner surfaces thereof, allowing the device to serve as a link plate to be received within one or more apertures in a second superiorly located spacing device. Both embodiments permit rotational optimization of the relative angle between the first and second spacing devices to fit the patient's anatomy. In certain embodiments of the interspinous process spacing device, the angled end of each angled attachment side of the interspinous process spacing device further comprises one or more angled fasteners extending from the inner surface at an angle other than ninety degrees and adapted for engaging the sacrum.

In certain embodiments of the interspinous process spacing device, each attachment side has a central portion and two wing portions extending in opposite directions from the central portion superiorly and inferiorly, and the inferior wings each have the angled end adapted to accommodate a sacrum and have one or more bone fasteners extending inwardly therefrom, and the superior wings each have one or more slots formed therein for receiving extension fasteners from a second interspinous process spacing device.

In certain embodiments of the interspinous process spacing device, the superior wings each have one or more bone fasteners extending inwardly therefrom. In certain embodiments of the interspinous process spacing device, the superior wings each have an extension fastener extending inwardly for attaching to another interspinous process spacing device. In certain embodiments of the interspinous process spacing device, the bone fasteners on the inferior wings each comprise a bone screw or movable spike or an axially expandable spike to engage the bone disposed through the wing. In certain embodiments of the interspinous process spacing device, the bone fasteners on the inferior wings further comprise one or more stationary spikes extending inwardly therefrom at angle different than an angle at which the bone screw or movable spike is disposed through the wing.

In certain embodiments of the interspinous process spacing device, the superior wings each have more than one slot formed therein for receiving fasteners extending inwardly from a second interspinous process spacing device. In certain embodiments of the interspinous process spacing device, the superior wings permit a fastened second interspinous process spacing device to pivot up to a 155 degree or a 60 degree angle with respect to the interspinous process device for implantation on the sacrum at the L5-S1 vertebrae.

The present invention further provides an interspinous process spacing system, comprising a first interspinous process spacing device and a second interspinous process spacing device, wherein the first interspinous process spacing device comprises two substantially flat attachment sides and a first spacer tray positioned therebetween, wherein one of the two substantially flat attachment sides is slideably positionable over the spacer tray. In certain embodiments of the interspinous process spacing device, wherein the second interspinous process spacing device comprises two offset attachment sides and a second spacer tray positioned therebetween, each of the offset attachment sides comprises a substantially flat end and an offset end.

The invention provides in certain embodiments that after implantation of the first interspinous process spacing device on a first and a second adjacent spinous process, the offset ends of the two offset attachment sides of the second interspinous process spacing device at least partially overlap respective adjacent ends of the substantially flat attachment sides of the first interspinous process spacing device when implanting the second interspinous process spacing device on the second and a third spinous process adjacent to the second spinous process.

In certain embodiments of the interspinous process spacing device, each of the offset ends of the two offset attachment sides comprises an integration means for integrating and attaching the offset end of the second interspinous process spacing device with a portion of the respective attachment side of the first interspinous process spacing device when overlapping.

In certain embodiments of the interspinous process spacing device, the integration means comprise fasteners extending inwardly from the second interspinous process spacing device which pivotally engage the one or more slots formed in each attachment side of the first interspinous process spacing device, such that the second interspinous process spacing device can pivot through a 155 degree angle with respect to the first interspinous process spacing device.

In certain embodiments of the interspinous process spacing device, each of the substantially flat attachment sides and the offset attachment sides comprises one or more bone fasteners extending from the inner surface for engaging respective spinous processes when implanted. In certain embodiments of the interspinous process spacing device, the substantially flat end on each of the offset attachment sides of the second interspinous process spacing device comprises one or more slots formed in an outer surface for receiving one or more fasteners extending from an inner surface of a respective offset attachment side of a third interspinous process spacing device adapted to overlap the substantially flat ends of the second interspinous process spacing device.

In certain embodiments the invention provides an interspinous process spacing device kit comprising: a first interspinous process spacing device comprising a first attachment side and a second attachment side, the first and the second attachment sides of the first interspinous process spacing device having a substantially flat configuration; a second interspinous process spacing device comprising a first attachment side and a second attachment side, the first and the second attachment sides of the second interspinous process spacing device having an offset configuration adapted to overlap a portion of a respective attachment side of the first interspinous process spacing device; and at least one insertion instrument adapted for retaining at least one of the first interspinous processing spacing devices or the at least one additional interspinous process spacing device and implanting the same.

In certain embodiments of the interspinous process spacing device, each interspinous process spacing device further comprises a spacer tray positioned between the first attachment side and the second attachment side, the spacer tray having a width and length extending from the first attachment side and slideably insertable through a tray slot formed in the second attachment side, wherein the spacer tray is adapted to retain adjacent spinous processes in a spaced apart orientation, and wherein the kit further comprises a plurality of alternatively sized first and second interspinous process spacing devices having different spacer tray widths.

The present invention further provides a surgical instrument system for implanting an interspinous process spacing device, comprising a means for positioning a first arm and a second arm in alignment for securing the interspinous process spacing device onto spinal processes. In certain embodiments of the surgical instrument system for implanting an interspinous process spacing device, the proximal and distal ends are offset to provide an unobstructed view of the distal ends when holding the proximal ends. In certain embodiments, each arm permits an engaged attachment side of the interspinous process spacing device at least 5 degrees, or at least 10 degrees, and up to 30 degrees, of rotation about an axis defined by the engagement element on the distal end of the arm. In certain embodiments of the surgical instrument system for implanting an interspinous process spacing device, the engagement element comprises an engagement projection which releaseably engages an instrument receptacle on the attachment side of the interspinous process spacing device, a mount for movably holding the engagement projection, and an implant guide extending distally past the engagement projection which engages an outer surface of an engaged attachment side of the interspinous process spacing device.

In certain embodiments of the surgical instrument system for implanting an interspinous process spacing device, the engagement projection on the second arm provides access to a securing means on the second attachment side of the interspinous process spacing device to secure the second side to the first side. In certain embodiments, the engagement projection is a threaded screw which engages a reciprocal threaded instrument receptacle instrument on the attachment side of the interspinous process spacing device. In certain embodiments, the threaded screw on the second arm is cannulated to provide access therethrough to a securing means on the second attachment side of the interspinous process spacing device to secure the second side to the first side while the second side is engaged to the second arm.

In certain embodiments of the surgical instrument system for implanting an interspinous process spacing device, the size, shape or indicia of the insertion instrument receptacle on the first attachment side is different from the size, shape or indicia of the insertion instrument receptacle on the second attachment side to facilitate connection to the correctly corresponding ends of the insertion instrument.

In certain embodiments of the surgical instrument system for implanting an interspinous process spacing device, the proximal ends of the first and second arms are releasably connectable at more than one selected distance. In certain embodiments of the surgical instrument system for implanting an interspinous process spacing device, the central portions of the first and second arms are releasably and rotatably connectable.

In certain embodiments, the present invention provides a top-down surgical instrument system for implanting an interspinous process spacing device, comprising a first arm having a proximal end, an elongated central portion and distal end, wherein the distal end has an interspinous process spacing device engagement element for posteriorly engaging a first attachment side of the interspinous process spacing device having a spacer tray extending inwardly therefrom. Certain embodiments comprise a second arm having a proximal end, an elongated central portion and distal end, wherein the distal end has an interspinous process spacing device engagement element for posteriorly engaging a second attachment side of the interspinous process spacing device having a spacer tray slot therein for receiving the spacer tray. In such embodiments, the second arm is removably and pivotally attachable to the first arm about an axis for positioning the first arm and the second arm in alignment for securing the interspinous process spacing device onto spinal processes.

In certain embodiments of the surgical instrument system for implanting an interspinous process spacing device, the second arm further comprises a pivot member or pin located on the central portion and the first arm further comprises a pivot channel or slot with a proximally oriented opening and a distally oriented curved retaining edge, such when the pin is slideably engaged in the slot against the retaining edge the first and second arms are removeably and pivotally attached to form a hinge, wherein the hinge permits positioning the first arm and the second arm in alignment for securing the interspinous process spacing device onto spinal processes.

In certain embodiments of the surgical instrument system for implanting an interspinous process spacing device, when the first and second arms each have a respective first and second attachment side of the interspinous process spacing device engaged thereto, and the first and second arms are attached at the hinge, drawing the proximal ends of the arms together will align and insert the spacer tray into the spacer tray slot of the first and second attachment sides of the interspinous process spacing device for securing the interspinous process spacing device onto spinal processes.

In certain embodiments of the surgical instrument system for implanting an interspinous process spacing device, the first arm further comprises a releasable locking mechanism for selectively securing the pin of the second arm into the slot of the first arm. In certain embodiments, the releasable locking mechanism is a leaf spring on the central portion of the first arm in blocking communication with the slot, such that the pin on the second arm can deflect the leaf spring during insertion into the slot and remain therein when the leaf spring returns to blocking communication to maintain the pin against the retaining edge on the first arm, and wherein the leaf spring can be manually disengaged from blocking communication with the slot to release the pin and separate the first and second arms.

In certain embodiments of the surgical instrument system for implanting an interspinous process spacing device, the surgical instrument comprises means for mechanically actuating the insertion instrument to close and open the first arm and the second arm for tightening the second attachment side relative to the first attachment side. In certain embodiments, the means for mechanically actuating is a ratchet bar pivotally mounted to the proximal end of the second arm and selectively engageable to the proximal end of the first arm, wherein the ratchet bar has a plurality of teeth on the proximal surface thereof which engage a corresponding flange on the proximal end of the first arm.

In certain embodiments of the surgical instrument system for implanting an interspinous process spacing device, the ratchet bar has one or more indicators of predetermined length corresponding to space between the mounted sides of the interspinous process spacing device. In certain embodiments, the ratchet bar further comprises a threaded track and a nut riding thereon outside the proximal end of the first arm for mechanically forcing the proximal ends of the arms together.

The present invention further provides a surgical instrument system for implanting an interspinous process spacing device, comprising a first arm having a proximal end, an elongated central portion and distal end, wherein the distal end has an interspinous process spacing device engagement element for posteriorly engaging a first attachment side of the interspinous process spacing device having a spacer tray extending inwardly therefrom. Such an embodiment also comprises a second arm having a proximal end, an elongated central portion and distal end, wherein the distal end has an interspinous process spacing device engagement element for posteriorly engaging a second attachment side of the interspinous process spacing device having a spacer tray slot therein for receiving the spacer tray. This embodiment can further be used with a compressor tool for positioning the first arm and the second arm in alignment for securing the interspinous process spacing device onto spinal processes.

In certain embodiments of the surgical instrument system for implanting an interspinous process spacing device, the compressor tool has a proximal handle end a central portion and a distal pair of opposing tangs moveable throughout a range between an open position and a compression position. In certain embodiments, the distal end of each arm comprises compressor tool guide channels and compression point indentations therein for receiving the compressor tool tangs. The compression points permit delivery of substantially equal amounts of pressure across each attachment side of the plate, allowing less invasive surgical implantation with a single compressor tool than would be required with multiple compression points and multiple compression tools. In certain embodiments, the tangs have distal compressor tips extending inwardly for engagement within the corresponding guide channels and compression point indentations on the arms, wherein the compression tool can rotate about an axis defined by the compressor tips so as to provide a user with a range of approach angles and approach from either side of the implantation tool and compress the arms to secure the aligned interspinous process spacing device onto spinal processes.

In certain embodiments of the surgical instrument system for implanting an interspinous process spacing device, the proximal end of one arm further comprises a retaining latch disposable on the distal end of the other arm to retain the arms in position relative to each other and in alignment for securing the interspinous process spacing device onto spinal processes.

In certain embodiments of the surgical instrument system for implanting an interspinous process spacing device, the surgical instrument comprises means for mechanically actuating the insertion instrument to close and open the first arm and the second arm for tightening the second attachment side relative to the first attachment side. In certain embodiments, the means for mechanically actuating is a ratchet bar pivotally mounted to the proximal end of the second arm and selectively engageable to the proximal end of the first arm, wherein the ratchet bar has a plurality of teeth on the proximal surface thereof which engage a corresponding flange on the proximal end of the first arm. In certain embodiments, the ratchet bar has one or more indicators of predetermined length corresponding to space between the mounted sides of the interspinous process spacing device. In certain embodiments, the ratchet bar further comprises a threaded track and a nut riding thereon outside the proximal end of the first arm for mechanically forcing the proximal ends of the arms together.

The present invention also provides a surgical instrument for selecting an interspinous process spacing device. In certain embodiments, the selection instrument comprises a first arm having a proximal end, an elongated central portion and distal end, wherein the distal end has a first interspinous process spacing measurement wing extending therefrom comprising a first spinous process stop element and a perpendicular wing template, and a second arm having a proximal end, an elongated central portion and distal end, wherein the distal end has a second interspinous process spacing measurement wing extending therefrom comprising a second spinous process stop element and a perpendicular wing template. In certain embodiments of the surgical instrument, the first and second arms are pivotally attached about an axis for positioning the first and second interspinous process spacing measurement wings to measure space between adjacent spinal processes. The instrument also allows for selection of an adjacent base plate or link plate superior or inferior to the existing implanted plate.

In certain embodiments of the surgical instrument, the measurement device can further comprise first and second wing templates adapted to overlap respective first and second adjacent spinal processes to determine space available on each spinous process for engaging an interspinous process implant. In certain embodiments, the instrument determines the space available for implantation of either a base plate device or an overlapping link plate device. In certain embodiments, the instrument can be adapted such that the proximal end of the first or second arm has a measuring element attached thereto with indicia to register length to the proximal end of the other arm, wherein said length corresponds to space between adjacent spinal processes as measured by the first and second spinous process stop elements. In certain embodiments of the surgical instrument, drawing the proximal ends of the arms together separates the wings to measure space between adjacent spinal processes. In one embodiment, the first or second wing template, or both, comprises a fastener template extending therefrom adapted to engage with a slot on an attachment side of an interspinous process spacing device previously implanted to determine space and orientation available for overlapping engagement of a link plate onto a base plate.

Example embodiments of interspinous process spacing devices are further described with reference to the FIGS. 1-12. Extending posteriorly from each vertebra are spinous processes. Laminae connect the spinous processes to respective transverse processes. Facet joints between the processes of adjacent vertebrae guide articulation of the vertebrae. Interspinous process spacing devices as described herein may be implanted between adjacent spinous processes of any of the cervical, thoracic, and/or lumbar vertebrae.

As shown in FIG. 1 are three engaged interspinous process spacing devices—a first base plate type interspinous process spacing device 130, a second link plate type interspinous process spacing device 132 overlapping the superior end of the first interspinous process spacing device 130, and a third link plate type interspinous process spacing device 134 overlapping the inferior end of the first interspinous process spacing device 130. The first interspinous process spacing device 130 includes a first attachment side 140 and a second attachment side 142, engaging either side of the adjacent spinous processes. Similarly, the second and third interspinous process spacing devices 132, 134 include a first attachment side 144 and a second attachment side 146. According to this embodiment, the attachment sides 144, 146 of the second interspinous process spacing device have an offset configuration to permit overlap with the first interspinous process spacing device 130. Thus, each of the first and second attachment sides 144, 146 of the second and third interspinous process spacing devices 132, 134 has a substantially flat end 148 and an offset end 149, with the offset being approximately the anticipated thickness of the first or second attachment side 140, 142 of the first interspinous process spacing device 130 (or a slight variation thereof), which is described and illustrated in more detail with reference to FIGS. 2-4.

According to various embodiments, the size and dimension of the first and the second attachment sides 140, 142, 144, 146 may vary according to the intended use of the interspinous process spacing devices 130, 132 which may vary based at least in part on the intended implant location on the spine, the patient size, the treatment, and the like. For example, attachment sides may vary in length and/or height to accommodate the varying sizes of spinous processes. Moreover, as described below with reference to FIGS. 5A-5C and 7A-7E, attachment side geometry may be adapted for implanting at specific locations of a spine that require different configurations, such as at the L5-S1 vertebrae.

Figure 6A:
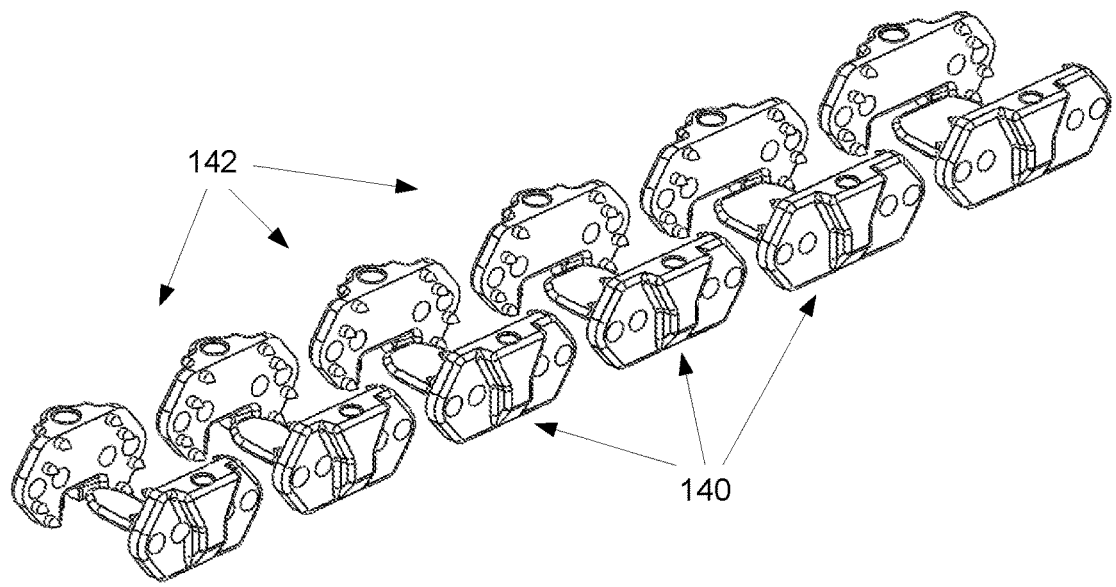
FIG. 6A is an isometric view of a set of a base plate interspinous process spacing devices having a gradient of spacer tray widths, according to an example embodiment.
Figure 6B:
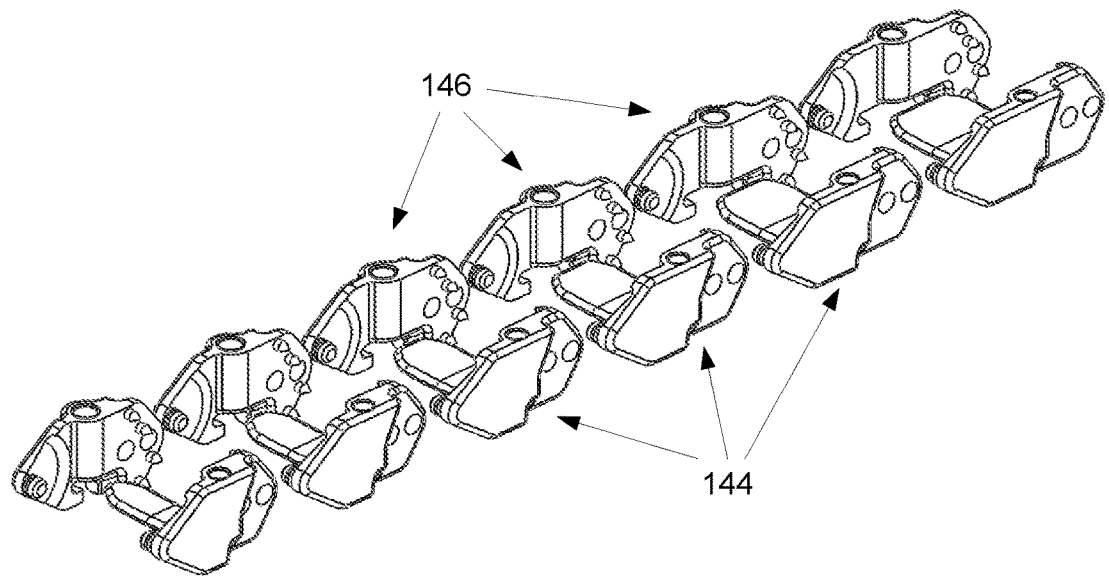
FIG. 6B is an isometric view of a set of link plate interspinous process spacing devices having a gradient of spacer tray widths, according to an example embodiment.

Similarly, spacer tray dimensions, as described below, may also vary in size, such as to accommodate varying patient and/or implant location anatomy. In one example, the spacer tray may have a substantially smaller width than is illustrated in FIG. 1, which may facilitate insertion through the ligaments existing between the spinous processes. Kits including interspinous process spacing devices with a range of spacer tray widths to select from are provided, such as shown in FIG. 6A-6B. In certain embodiments, the spacer tray widths can be provided in increments ranging from less than or 8 mm, 10 mm, 12 mm, 14 mm, 16 mm, to 18 mm, or more, such as shown in FIGS. 6A-6B. Example spacer tray lengths can be 10 mm to 30 mm, or 23.4 mm. In another example, an interspinous process spacing device may not include a spacer tray. A spacer tray selection instrument is also provided and is described in more detail below with reference to FIGS. 21A and 21B.

In certain example embodiments, the width of the wings on a base and link plate, such as shown in FIGS. 2-3 can be 3 mm, the width of the central portion of the first attachment side can be 6 mm, and the width of the central portion of the second attachment side can be 8.5 mm. An exemplary height for the base plate and link plate attachment sides is 18 mm.

In certain example embodiments, the length of the wings on either side of the spacer tray can be 10.5 mm for a first interspinous process device base plate and 12.5 mm for a second interspinous process device link plate. Therefore, for an example device with a 8 mm spacer tray width, the total plate length for a base plate would be 29 mm, and for a link plate would be 31 mm.

Each of the interspinous process spacing devices 130, 132 may include a spacer tray 150 extending between attachment sides 140, 142 and 144, 146, respectively. The spacer tray 150 is configured with surfaces to abut the spinous processes to maintain the spaced apart relationship of the spinous processes. According to various embodiments, as illustrated in FIGS. 1-12, the spacer tray 150 may have a substantially open configuration that is accessible from the posterior direction, which serves to maximize the surface area for bone growth promoting substances. Access from the posterior direction allows the surgeon to insert the bone growth promoting substance (or any other material to facilitate bone in-growth, structural support, and/or healing) after implanting the interspinous process spacing devices. Otherwise, without posterior access, the bone growth promoting substance must be inserted prior to implantation, which likely will not result in the most effective placement and/or quantity of bone growth promoting substance. In contrast to conventional interspinous spacers, which typically have a circular cross-section and occupy a substantial area between adjacent spinous processes, the spacer tray 150 described herein has a reduced cross-sectional profile and a tapered width on the leading front edge, which eases insertion between the ligaments occupying the space between adjacent spinous processes. The conventional devices often require significant retraction and/or cutting of the ligaments to implant a device because the larger, circular cross-section of the components existing between the sides cannot easily be inserted between the ligaments, increasing the difficulty, risk, and healing time of the implant procedure.

Accordingly, the spacer tray 150 described herein can be inserted between the ligaments without cutting due to its reduced, tapered, or flattened profile compared to the larger, circular cross-sections of other devices. However, in other embodiments, the spacer tray 150 may be configured in a variety of shapes and sizes to accommodate anatomical variation among patients and intended treatment and space correction, and to accommodate the positioning of a securing mechanism, as further described below. The spacer tray 150 may further optionally include apertures through the spacer tray 150, which act to facilitate bone and tissue in-growth by maximizing the available surface area from the adjacent spinous processes and cause further fusion thereof. These and other features and variations thereof are discussed in more detail with reference to the following FIGS. 2-12.

Moreover, according to another embodiment, the spacer tray 150 may have a minimized width to increase the ease of insertion and to occupy less space between adjacent spinous processes. In fact, in one embodiment a spacer tray may not be included at all, and alignment, connection, and stability between the two attachment sides 140, 142 may be accomplished by way of the securing means, such as those described with reference to FIGS. 8 and 10. In this embodiment, the securing means may further serve to absorb impact from, and to limit movement of, one or more of the adjacent spinous processes, which otherwise would be achieved by a spacer tray.

FIGS. 2-7 show details of interspinous process spacing devices according to one embodiment, such as the first interspinous process spacing device 130 (as illustrated in FIG. 1). FIGS. 6-9 show example spacer tray 150 configurations, according to various example embodiments. The first attachment side 140 includes a spacer tray 150 extending in a substantially perpendicular direction from the first attachment side 140. The spacer tray 150 shown is configured to have a substantially arcuate cross-sectional shape, permitting access to the tray after implanting the interspinous process spacing device 130. However, the spacer tray may have any cross-sectional shape, such as, but not limited to, flat, angled, a partial square, a partial hexagon, a partial octagon, a T-shape, a cross shape, and the like, such as, but not limited to, those illustrated by example in FIGS. 1-12. The dimensions of the spacer tray 150 can depend upon the desired level of movement and/or size of the desired space to be retained between the two adjacent spinous processes. The spacer tray 150 may further optionally include chambers formed through the tray, which may be oriented to provide additional clearance of the spacer tray 150 from posteriorly facing bone surfaces (e.g., spinous processes, facet joints, etc.). Accordingly, a spacer tray 150 acts to maintain a minimum distance between adjacent spinous processes to move the vertebrae apart and relieve pressure on nerve tissue and/or facet joints.

The cross-sectional shape of the spacer tray 150 can facilitate insertion into the tray slot 210. For example, as shown in FIGS. 2-7, the T-shaped cross-section, with the bottom of the T extending medially or downward into the spine provides a supporting lift for the tip of the spacer tray off of the vertebrae and into the tray slot. Similarly, the tapering cross-section of the tip of the spacer tray into a rounded point facilitates insertion into the slot, as well as facilitating insertion through the ligaments existing between the spinous processes. Finally, the arcuate longitudinal cross-section facilitates insertion when both sides are engaged with an insertion tool and being drawn together in an arc, as described below.

Figure 9A:
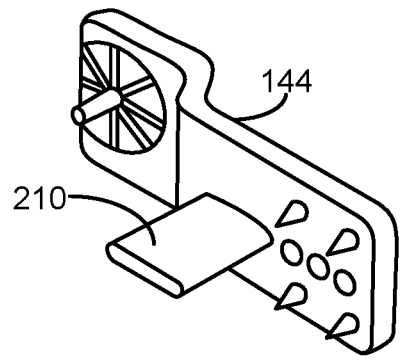
FIG. 9A is an isometric view of a first attachment side of an interspinous process spacing device link plate with an alternative spacer tray, according to an example embodiment.
Figure 9B:
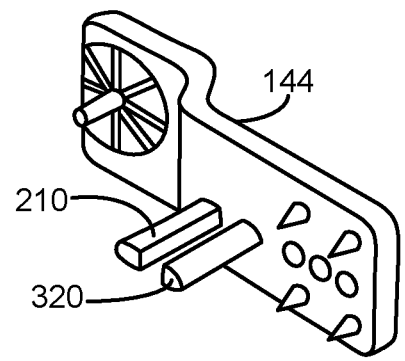
FIG. 9B is an exploded isometric view of a first attachment side of an interspinous process spacing device link plate with an alternative spacer tray, according to an example embodiment.
Figure 9C:
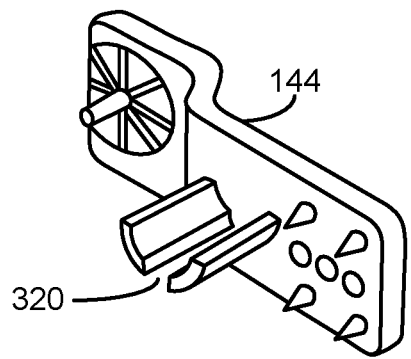
FIG. 9C is an exploded isometric view of a first attachment side of an interspinous process spacing device link plate with an alternative spacer tray, according to an example embodiment.
Figure 9D:
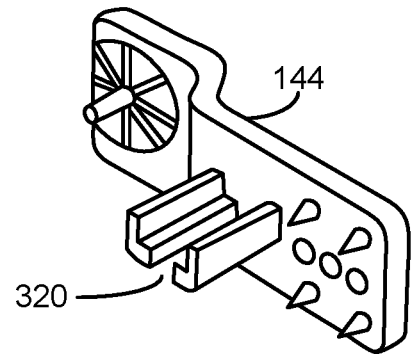
FIG. 9D is an isometric view of a first attachment side of an interspinous process spacing device link plate with an alternative spacer tray, according to an example embodiment.

Moreover, the spacer tray 150 is shaped to permit access from the posterior direction, which increases the ease with which bone growth promoting substance is placed above the spacer tray 150 and proximate the vertebrae, while also increasing the available spinous process surface area. In some embodiments, bone growth promoting substance can be inserted in or near other areas of the interspinous process spacing device. Also as illustrated in FIGS. 9B-9D, the spacer tray 150 can optionally include tray apertures 320 or other openings extending through the spacer tray 150 to further facilitate tissue and/or bone in-growth. Any number of tray apertures 320 may be included in any size, shape, or configuration. As used herein, bone growth promoting substance may include, but is not limited to, bone paste, bone chips, bone strips, structural bone grafts, platelet-derived growth factors, bone marrow aspirate, stem cells, bone growth proteins, bone growth peptides, bone attachment proteins, bone attachment peptides, hydroxylapatite, calcium phosphate, and/or other suitable bone growth promoting substances.

The second attachment side 142 includes a tray slot 210 having a similar shape as the spacer tray 150 to permit the spacer tray 150 to slide therethrough. Accordingly, the second attachment side 142 is slideably adjustable along the axis of the spacer tray 150 so the second attachment side 142 can move toward the first attachment side 140 when tightening to allow the attachment sides 140, 142 to be positioned along either side of, and secured to, the spinous processes. It is appreciated that in other embodiments, the spacer tray may extend from the second attachment side and slideably pass through the first attachment side, and that the orientation relative to the patient's spine may vary from that described and illustrated herein.

According to one embodiment, as is shown in more detail with reference to FIG. 4 and FIG. 6 (a simplified perspective view of an interspinous process spacing device), the tray slot 210 is sized slightly larger than the cross-section area of the spacer tray 150 to provide loose fitting of the second attachment side 142 over the spacer tray 150, permitting at least slight angular movement of the second attachment side 142 relative to the first attachment side 140, but providing enough constraint so as to retain the approximate orientation of the second attachment side 142 relative to the spacer tray 150. As a result of this slight angular variation allowed, opposite ends of the attachment sides can be tightened independently and can adapt to adjacent spinous processes having varied thicknesses (e.g., permitting the attachment sides to close tighter or narrower on one end relative to the other, such as if one spinous process is smaller or narrower than the other). The size of the tray slot 210 relative to the spacer tray 150 may vary according to the desired level of angular variation of the second attachment side 142 relative to the first attachment side 140. In other embodiments, however, the tray slot 210 may form a tight fit around the spacer tray 150 to prevent significant angular variation or other movement of the second attachment side 142 relative to the spacer tray 150. The fit between the tray slot 210 and the spacer tray 150 further serves to absorb torque or any other force applied by the spacer tray 150 against the second attachment side 142, providing increased stability of the attachment sides 140, 142 relative to each other and against the patient's spinous processes when implanted.

In certain embodiments of the interspinous process spacing device, the tray slot engages the spacer tray with freedom of movement to permit at least 20 degrees of lateral rotation of the second attachment side relative to the first attachment side prior to engaging the securing means. However, in other embodiments, the tray slot 210 may form a more secure fit with the spacer tray 150, preventing significant angular movement therein. For example, in embodiments in which the securing mechanism utilizes a gearing mechanism, a tighter fit may serve to prevent cross-threading or poor meshing of the gearing mechanisms.

Also illustrated in FIGS. 2-7 are fasteners 220 extending from the inner surfaces of each of the attachment sides 140, 142. The fasteners 220 improve the ability of the attachment sides 140, 142 to engage the spinous processes and/or serve as an integration means to engage the exterior surface of the adjacent interspinous process spacing device, such as is illustrated in and described with reference to FIGS. 5A-5C. In certain embodiments of the interspinous process spacing device, the integration means comprise fasteners extending inwardly from the second interspinous process spacing device which pivotally engage the one or more slots formed in each attachment side of the first interspinous process spacing device, such that the second interspinous process spacing device can pivot through a 155 degree angle with respect to the first interspinous process spacing device. In certain embodiments of the interspinous process spacing device, the second interspinous process spacing device can pivot through a 60 degree angle with respect to the first interspinous process spacing device. In certain embodiments of the interspinous process spacing device, such as illustrated in FIGS. 5A-5B, where multiple apertures are provided for the fastener, and where multiple apertures partially overlap as illustrated in FIG. 5C, the second interspinous process spacing device can pivot through a range of angles with respect to the first interspinous process spacing device. It is understood that the device can be configured for pivotal rotation of the first interspinous process spacing device relative to the second interspinous process spacing device through any range of degrees desired including for example 180, 170, 160, 155, 150, 140, 130, 120, 110, 100, 90, 80, 70, 60, 50, 40, 30, 20, 10, 5 and 0 degrees. In certain embodiments of the interspinous process spacing device, the second interspinous process spacing device can pivot posteriorly and anteriorly through substantially equal or unequal degrees in each direction with respect to the first interspinous process spacing device.

The fasteners 220 illustrated in FIGS. 2-7 are shown as teeth or barbs, but any other fastening or other securing mechanism may be used, including, but not limited to, pins, hooks, wires, spikes, straps, clamps, sutures, adhesives, or any other suitable fastening mechanism. Moreover, according to various embodiments, the fasteners 220 may be interchangeable with other types of fastening mechanisms and/or may be adjustable to accommodate varying anatomy among patients. In addition to, or in lieu of, the fasteners 220 shown in FIGS. 2-7, other integration means may be provided that facilitate the integration of and securement between two adjacent interspinous process spacing devices when implanted in an overlapping configuration.

In the embodiments shown in FIGS. 1-7, the fasteners 220 are projecting inward from second link plates 144,146 of the second interspinous process spacing device toward slots 315 in base plates 140,142 of the first interspinous process spacing device to pivotally engage the two devices together prior to further securing with securing means 230 which is in this embodiment a set or bearing screw. Bone fastening members 225 are shown on the inner surfaces of the plates. In certain embodiments, the bone fastening members alternately extend from each opposing plate to different points on the spinous process to minimize the potential for fracture by bearing directly on opposing sides of the bone. Examples of these and other integration members are illustrated in and described with reference to FIGS. 1-12.

Example securing means 230 are particularly illustrated by FIG. 4 with set screw extending through the central portion of the second attachment side 142 onto the spacer tray 150 in the tray slot 210. Various additional example embodiments illustrated and described in more detail with reference to FIG. 8. The securing means 230 illustrated in FIG. 8 includes two spaced apart screws 310 extending between the attachment sides 140, 142 and oriented substantially along the same axis as the spacer tray 150. In the embodiment illustrated in FIG. 8, the screws 310 extend through the second attachment side 142 through apertures 312 and are received by the complementary threaded collars 314 extending from the inner surface of the first attachment side 140. However, it is appreciated that the screws 310 may instead pass through the first attachment side 140 and be received by collars on the second attachment side 142 in other embodiments. According to one embodiment, the threaded collars 314 extend a given distance from the inner surface of the first attachment side 140 so as to permit receiving the respective screws 310 while the attachment sides 140, 142 are still sufficiently separated, and to reduce the length of the screws 310. The distance the threaded collars 314 extend may vary, but can be determined to extend the maximum distance without interfering with the vertebrae, other components of the interspinous process spacing device, and/or access to spacer tray 150 to provide bone growth promoting substance therein. Similarly, the orientation of the securing means 230 is chosen to avoid interfering with the vertebrae (e.g., the spinous process) during implantation, while also providing maximum securing and purchase strength of the attachment sides 140, 142 to the spinous process. In another example, one or more screws 310 can be positioned between the space of a spacer tray 150 formed from multiple members and creating a space therein.

Spaced apart screws (or other securing means, as described in more detail below) permit independently adjusting opposite ends of the attachment sides 140, 142 and thus independently securing opposite ends of the attachment sides 140, 142 to the respective spinous process. For example, during tightening, the superior screw can be incrementally tightened, then the inferior screw can be incrementally tightened, and so forth until each end of the attachment sides 140, 142 is secured to the respective spinous process. This method allows tightening the interspinous process spacing device by "walking" opposite ends, and thus accounting for varied thicknesses of adjacent spinous processes. Additional embodiments including spaced apart screws or similar spaced apart securing means are described with reference to FIGS. 8A-8D.

Moreover, some example securing means described herein may generally avoid having to use a separate clamping and/or insertion instrument. By tightening the screws 310, the attachment sides 140, 142 close on the spinous processes without any additional clamping or tightening force. However, other securing means described herein can be implanted using an insertion instrument to facilitate retaining desired positioning of the interspinous process spacing device and/or to tighten the attachment sides 140, 142 against the spinous processes. In certain embodiments, the insertion instrument can also aid in aligning and engaging the two attachment sides of the device without requiring removal of the spinous process ligament. For example, the device embodiments described may be used to initially insert and position an interspinous process spacing device, while the securing means of the interspinous process spacing device may be used to achieve final fixation to the spinous processes. Though, in other embodiments, a clamping and/or insertion instrument may have an integrated tightening means (e.g., geared, ratchet, lever, etc.) that facilitates securing an interspinous process spacing device to the spine by tightening the clamping instrument, while the securing means of the interspinous process spacing device serve to secure and retain the device in tightened configuration.

Figure 10:
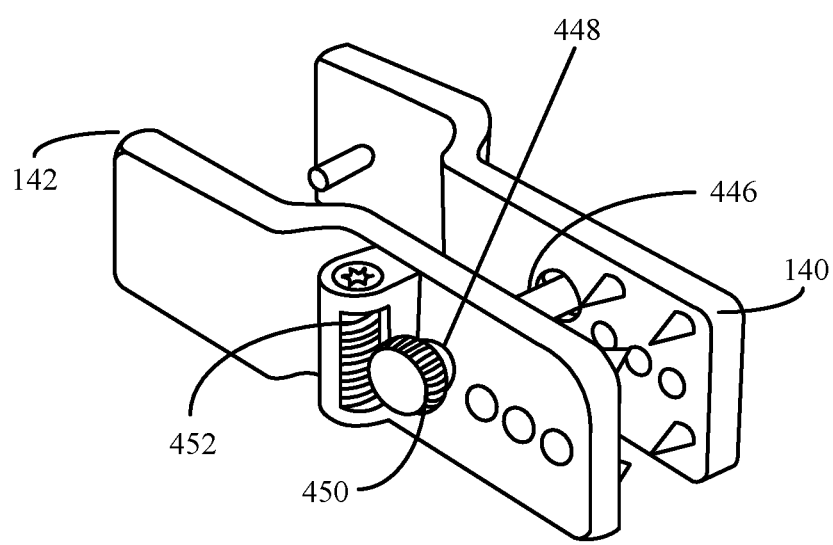
FIG. 10 is an isometric view of an alternative interspinous process spacing device, according to an example embodiment.

Additional securing means embodiments are illustrated in FIG. 8 and FIG. 10. FIG. 8B illustrates the securing means as described, incorporating two spaced apart screws 310 passing through apertures 312 in the second attachment side 142 and threadably received by collars 314 in the first attachment side 140. In this embodiment, the screws 310 are positioned posterior from the spacer tray 150 and substantially within the diameter of the spacer tray 150, to avoid interference with the vertebrae upon implant. However, any other locations may be used as desired. In addition, according to other embodiments, more than two screws can be used, or only one screw can be used.

Figure 8A:
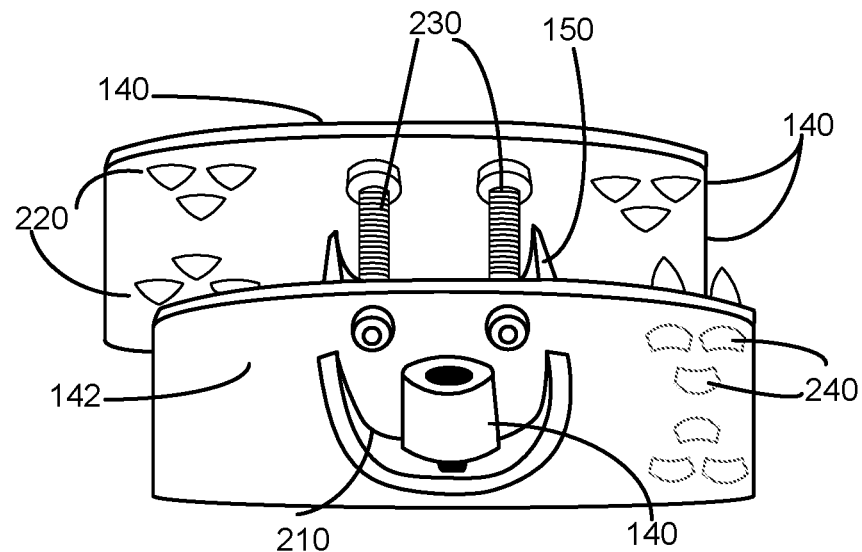
FIG. 8A is an isometric view of an interspinous process spacing device, according to an example embodiment.
Figure 8B:
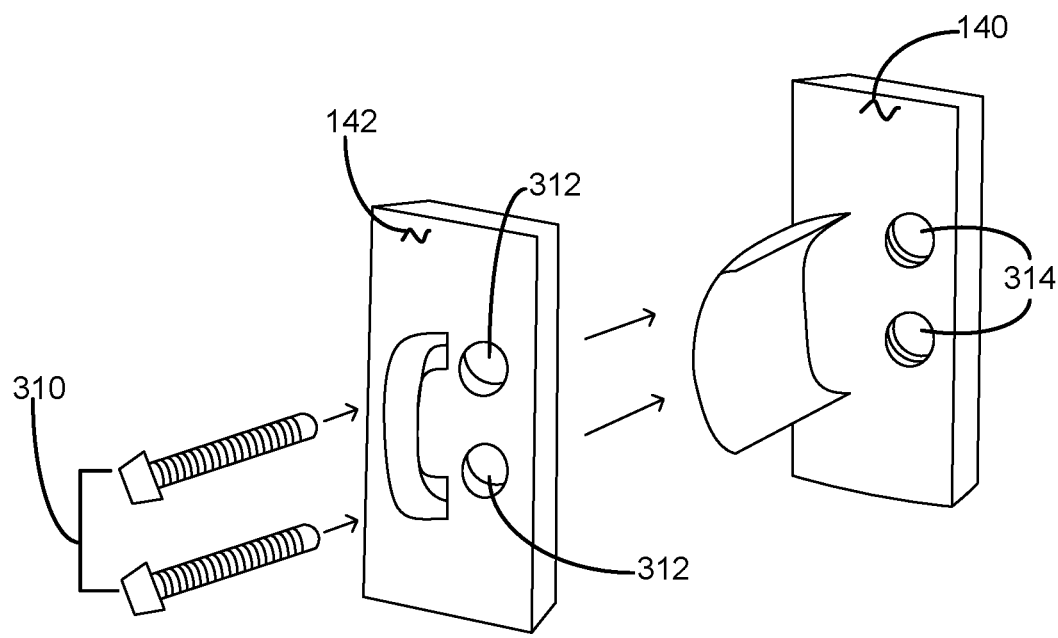
FIG. 8B is an exploded isometric view of an interspinous process spacing device, according to an example embodiment.
Figure 8C:
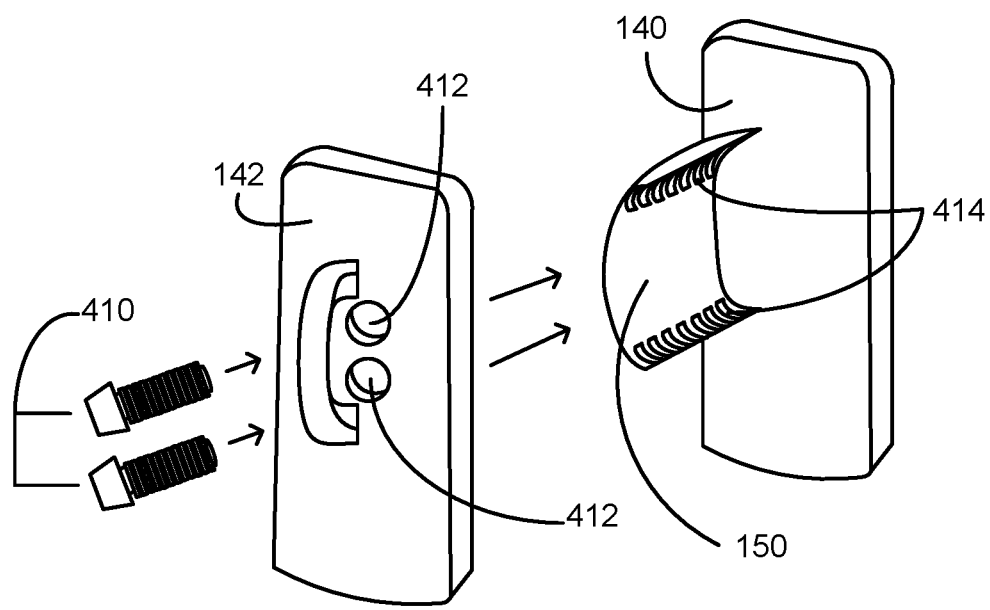
FIG. 8C is an exploded isometric view of an interspinous process spacing device, according to an example embodiment.

FIG. 8C illustrates another embodiment of a securing means used to tighten the opposing attachment sides 140, 142 on adjacent spinous processes. In this embodiment, two spaced apart worm drive mechanisms include two screws 410 (i.e., the worms) passing through two apertures 412 in the second attachment side 142 and operably engaging worm gearing 414. The worm drive mechanisms are adapted to provide movement along the axis of the spacer tray 150 as a result of the rotational forces applied to screws 410 that are transferred to the adapted worm gearing 414. In this embodiment, instead of a traditional worm gear, a portion of the inner surfaces are toothed complementary to the screws 410. Thus, when the screws 410 operably engage the teeth of the worm gearing 414 on the surface of the spacer tray 150, the screws' 410 threading passes along the worm gearing and causes the second attachment side 142 to move along the spacer tray 150. It is appreciated that, in other embodiments, the worm gearing 414 may be on any other surface of the spacer tray 150, or worm gearing separate from the spacer tray 150 may be provided. For example, in one embodiment, one or more screws (e.g., the worms) may rotatably extend through the inner surface of the first attachment side 140 and extend through apertures in the second attachment side 142. In this configuration, which is essentially reversed from the above-described worm drive mechanism, the worm screw extending along the axis of the spacer tray 150 is turned against a worm gear rotatably affixed to one of the attachment sides 140, 142, causing the second attachment side 142 to move along the screws. Again, in any of these embodiments, two spaced apart worm drive mechanisms permit the independent tightening, and thus the "walking" effect when closing the attachment sides 140, 142 on the spinous processes.

Figure 8D:
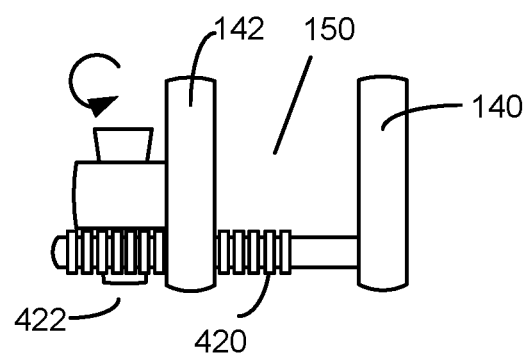
FIG. 8D is a side view of an interspinous process spacing device, according to an example embodiment.

FIG. 8D illustrates a side view of another embodiment of a securing means used to tighten opposing attachment sides 140, 142 onto adjacent spinous processes. According to this embodiment, two spur gear mechanisms include gearing teeth 420 formed on the inner or outer surfaces of the spacer tray 150, much like that described with reference to FIG. 8C, and a shaft and gear 422 rotatably affixed to the outer surface of the second attachment side 142 that meshes with the gearing teeth 420 of the spacer tray. This embodiment behaves similar to a rack and pinion, whereby the gearing teeth 420 serve as a rack and the shaft and gear 422 serve as the pinion. Accordingly, turning each of the shaft and gears 422 causes the gears to operably mesh with the gearing teeth 420 and close the second attachment side 142 toward the first attachment side 140. It is appreciated that, in one embodiment of a spur gear mechanism (or any other securing means embodiments described herein), the shaft and gears can include a one-way or reverse lock-out mechanism to only permit rotation or movement in one direction—that which results in tightening the attachment sides together, but restricts movement in the opposite direction. In some embodiments, the one-way or reverse lock-out mechanisms may be selectively actuated, such that an operator may release them (e.g., to reposition the device, to remove the device, etc.).

According to another embodiment, a mechanism configured in a manner similar to a rack and pinion is used. Instead of the gearing being integrated with a spacer tray, this embodiment includes a separate geared rack extending from the first attachment side 140 and slideably positioned within an aperture formed in the second attachment side 142. The aperture can be sized to permit the geared rack to slide within the aperture. Also integrated or adapted with the second attachment side 142 is a shaft and gear that meshes with the geared rack. This embodiment behaves similar to a rack and pinion, whereby the shaft and gear serve as the pinion for the geared rack, advancing the second attachment side 142 along the geared rack when the shaft and gear is turned, rotated, or otherwise actuated. Any one-way or reverse lock-out mechanism to permit rotation or movement in only one direction optionally can be incorporated in the securing means embodiment. In one embodiment, the gearing on both the geared rack 440 and the shaft and gear are complementarily angled with respect to each other, which serves to hold the position of the shaft end gear against the geared rack when tightened and resists backing out or otherwise loosening by the attachment sides 140, 142 when secured in place.

In one embodiment the fit of the geared rack within the aperture is a relatively tight fit to reduce angular movement of the second attachment side 142 relative to the geared rack, which may serve to reduce the potential of cross-threading or otherwise preventing meshing of the shaft end gear with the geared rack. In other embodiments, however, the fit may be looser, allowing at least partial angular movement of the second attachment side 142 relative to the geared rack. A looser fit may be used to allow the attachment sides 140, 142 to be positioned at an angle (i.e., not exactly parallel to each other) to account for differences in the width of adjacent spinous processes.

FIG. 10 illustrates another embodiment of a securing means used to tighten the opposing attachment sides 140, 142 on adjacent spinous processes. In this embodiment, a worm drive mechanism is used, similar to that described with reference to FIG. 8C. The worm drive mechanism according to this embodiment includes a threaded shaft 446 extending from the first attachment side 140 and passing through an aperture 448 in a second attachment side 142. According to one embodiment, the threaded shaft 446 can be configured like a threaded bolt integrated with, and extending from, the interior surface of the first attachment side 140. The threaded shaft 446 can be fixed to the first attachment side 140 (either integrated or bolted thereto). A worm gear nut 450 is threadably received by the threaded shaft 446 from the outside of the attachment side 142, holding the second attachment side 142 on the threaded shaft 446. The worm gear nut 450 includes teeth or gearing on its exterior surface which operably meshes with a screw 452 (or other threaded shaft operable for turning by an operator). The screw 452 acts as a worm, causing the worm gear nut 450 to rotate around the threaded shaft 446, which in turn causes the worm gear nut 450 to tighten or loosen on the threaded shaft 446. Accordingly, by rotating the screw 452, such as by using a screwdriver or other instrument received by a head of the screw 452, the worm gear nut 450 can be tightened over the threaded shaft 446, causing the second attachment side 142 to tighten toward the first attachment side 140 over the threaded shaft 446 and a spacer tray (not shown to simplify this illustration).

In one embodiment, the fit of the threaded shaft 446 within the aperture 448 is a relatively tight fit to reduce angular movement of the second attachment side 142 relative to the threaded shaft 446, which may serve to reduce the potential of cross-threading or otherwise interfering with the meshing of the screw 452 with the worm gear nut 450. In other embodiments, however, the fit may be looser, allowing at least partial angular movement of the second attachment side 142 relative to the geared member, such as may be used to allow the attachment sides 140, 142 to be positioned at an angle (i.e., not exactly parallel to each other) to account for differences in the width of adjacent spinous processes. Although FIG. 10 shows a particular orientation and placement of the threaded shaft 446 and the screw 452, any other orientation and/or configuration may be used.

In yet another embodiment of a securing means used to tighten the opposing attachment sides 140, 142 on adjacent spinous processes. In this embodiment, a worm drive mechanism is also used, similar to that described with reference to FIG. 10. However, according to this embodiment, the threaded member extending between the first attachment side 140 and the second attachment side 142 is configured differently. In this embodiment, the threaded member includes a fixed worm gear head positioned on the end of the threaded member extending through the aperture in the second attachment side 142. The fixed worm gear head is in a fixed relationship relative to the threaded member, and which does not thread or otherwise turn independent of the threaded member. The threaded member of this embodiment is further configured to be received by and threaded into a threaded receiver, as is shown in the top view cross-sectional illustration. A screw operably meshes with the fixed worm gear head, and is configured in the same or similar manner as is described with reference to FIG. 10. Accordingly, when turning the screw, the fixed worm gear head causes the threaded member to thread into or out of the threaded receiver of the first attachment side 140, which in turn causes the first attachment side 140 to tighten toward the second attachment side 142.

According to one embodiment, the threaded member has an at least partially tapered end (e.g., configured as a screw), which threads into and out of the threaded receiver. In one embodiment, a threaded member with a tapered end can self tap the threaded receiver; though, in other embodiments, the threaded receiver has complementary threads already formed therein. In other embodiments, the threaded member has a substantially straight shaft with a substantially constant diameter at or near its tip (e.g., configured as a bolt). As described above, the fit of the threaded member within the aperture may be a tight or loose fit.

FIGS. 11A-11D illustrate yet another embodiment of a securing means used to tighten the opposing attachment sides 140, 142 on adjacent spinous processes. This embodiment includes a worm gear configuration, similar to those described with reference to FIG. 10. According to this embodiment, however, the threaded member 451 extending between the first attachment side 140 and the second attachment side 142 is configured differently. In this embodiment, the threaded member 451 also includes a fixed worm gear head 457 (which may also be referred to as a "gear" or "worm gear" fixed on the end of the threaded member 451 extending through an aperture in the second attachment side 142 and operably meshing with the screw 452.

Figure 11A:
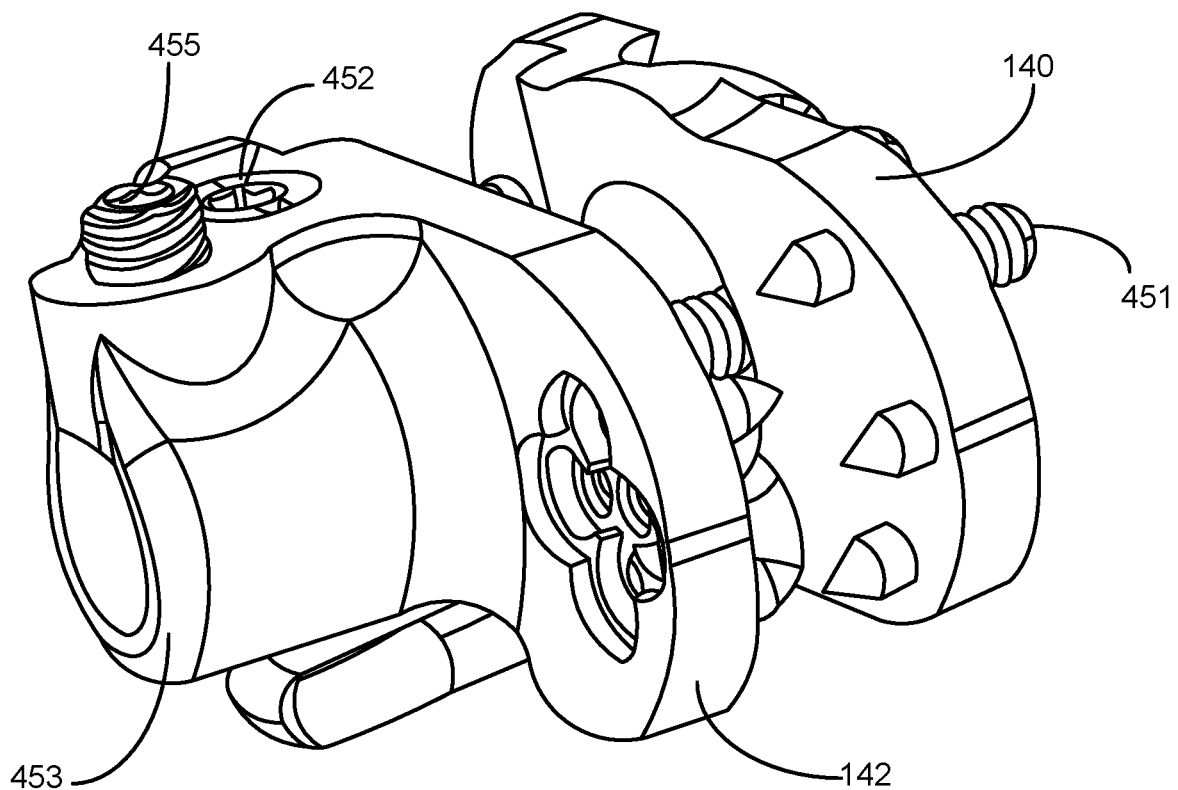
FIG. 11A is an isometric view of an alternative interspinous process spacing device, according to an example embodiment.
Figure 11B:
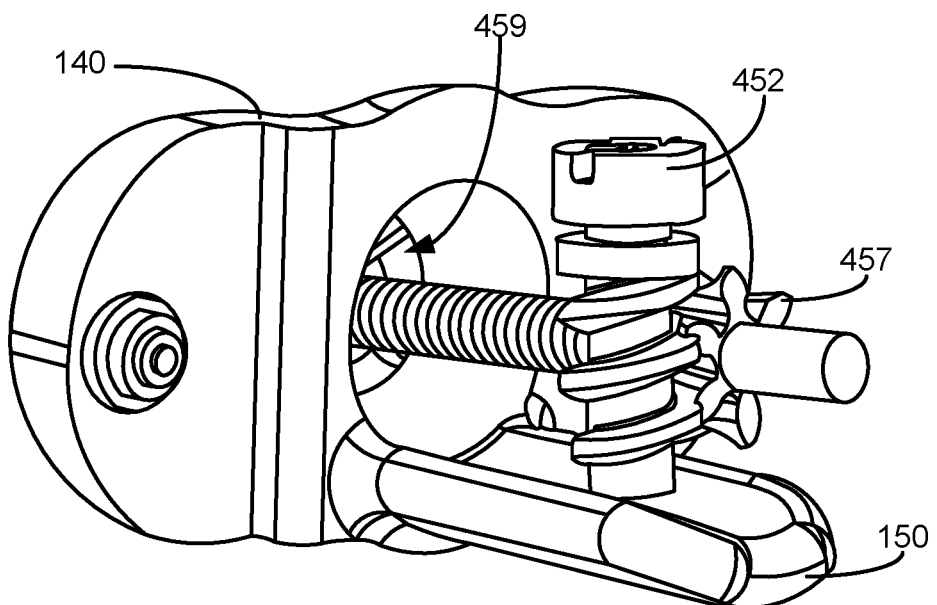
FIG. 11B is an isometric view of the first attachment side of the alternative interspinous process spacing device integrating an alternative worm-gear advancement mechanism for the first and second attachment sides, according to an example embodiment.
Figure 11C:
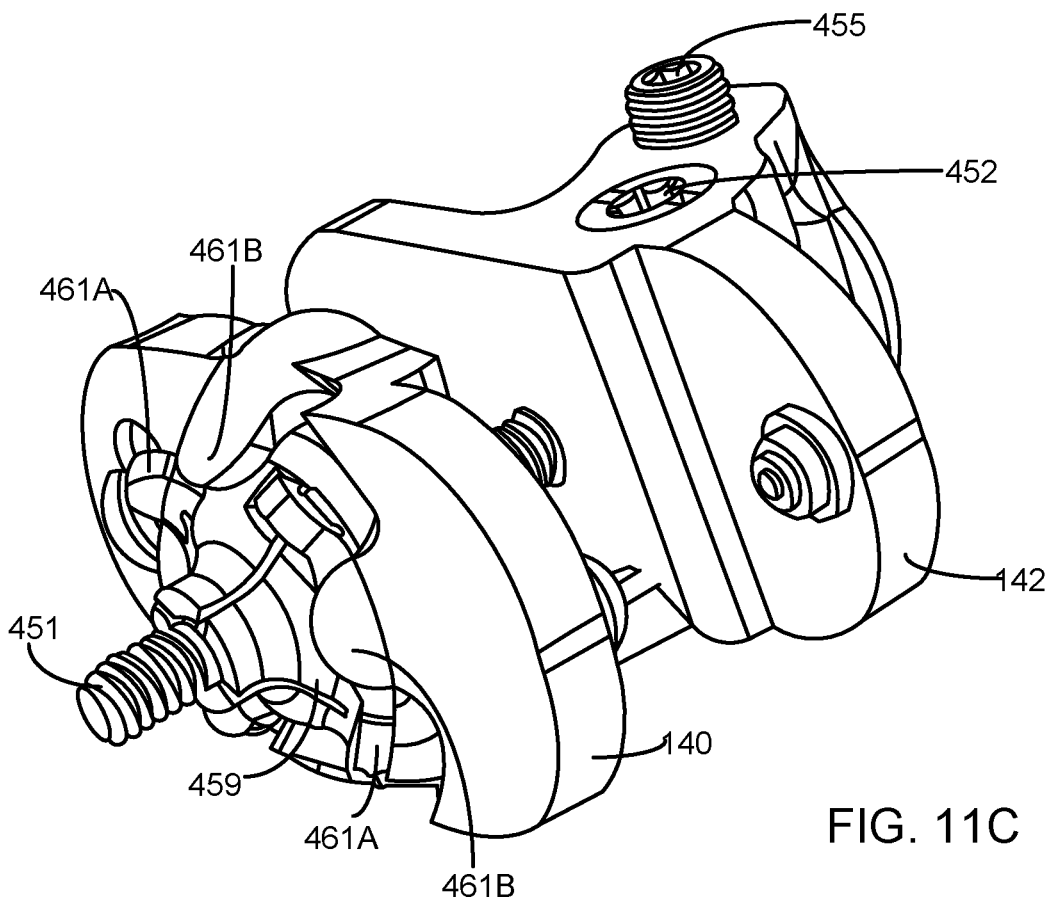
FIG. 11C is an isometric view of the alternative interspinous process spacing device, according to an example embodiment.

However, the threaded member 451 of this embodiment is further configured to be received by and threaded into a floating receiving member 459 retained on the exterior surface of the first attachment side 140, as is shown in more detail in FIG. 11C. The floating receiving member 459 includes a threaded orifice having threads complementary to the threads on the surface of the threaded member 451. The floating receiving member 459 is retained on the exterior surface of the first attachment side 140 by one or more pivotable retention means 461, such as, but not limited to, retaining tabs, flanges, hooks, or other members adapted to retain the floating receiving member 459 while still allowing pivoting, rocking, translational, and/or angular movement relative to the attachment side 140. As illustrated in FIG. 11C, the pivotable retention means 461 according to this embodiment includes flanges or tabs 461a extending from the floating receiving member 459 and cooperating flanges or tabs 461b extending from the first attachment side 140, overlapping the floating receiving member 459, and loosely fitting between the flanges or tabs 461a, thus retaining the floating receiving member 459 in place. According to this embodiment, the flanges or tabs 461a, 461b prevent rotation of the floating receiving member 459 while threading it over the threaded member 451, but still allow at least limited pivoting, rocking, and the like due to the loose fitment of, and play existing between, corresponding flanges or tabs 461a, 461b. The floating receiving member 459 thus allows the first attachment side 140 to be angled relative to the threaded member 451 (or an axis existing between the two attachment sides 140, 142) so the attachment sides are not required to be implanted in parallel orientation relative to each other. Moreover, according to one embodiment, the floating receiving member 459 can include one or more slits formed at least partially along the length of the threaded portion, as shown in FIG. 11C, for example, which allows spreading the threaded portion for quick insertion of the threaded member 451 therein and subsequently pressing the threaded portion thereby engaging the threads. In one embodiment having one or more slits, a quick release mechanism may be included that spreads the spacing between the slits and disengages the floating receiving member 459 from the threaded member 451. In yet another embodiment, a floating receiving member 459 can include a threaded portion that is split and further includes a locking screw or other similar feature that will allow fast insertion and quick release of the device.

The securing means includes a screw 452 that operably meshes with the fixed worm gear head 457, such that, when turning the screw 452, the fixed worm gear head 457 causes the threaded member 451 to thread into or out of the floating receiving member 459, which in turn causes the first attachment side 140 to tighten toward the second attachment side 142.

As shown in FIG. 11A, the securing means according to this embodiment optionally includes a casing 453 that at least partially (or entirely, as illustrated) encases the end of the threaded member 451 and the fixed worm gear head 457 extending from the surface of the second attachment side 142 and providing access to the screw 452. The casing 453 can protect the surrounding tissue from irritation or injury that may be caused by the components protruding from the interspinous process spacing device. It is further appreciated that a casing similar to that illustrated in FIG. 11A may be included with any of the other embodiments described herein, such as in a similar manner to at least partially cover components protruding therefrom (e.g., extending from the first and/or the second attachment sides). FIG. 11A also shows at least one set screw 455 threadably extending through the casing 453 for engaging the threaded member 451 upon implantation (not shown for simplicity in FIG. 11B). In other embodiments, a set screw may not be included, but other securing mechanisms may be used to prevent rotation or movement of the threaded member 451 and the second attachment side 142 relative to each other after implant.

Figure 11D:
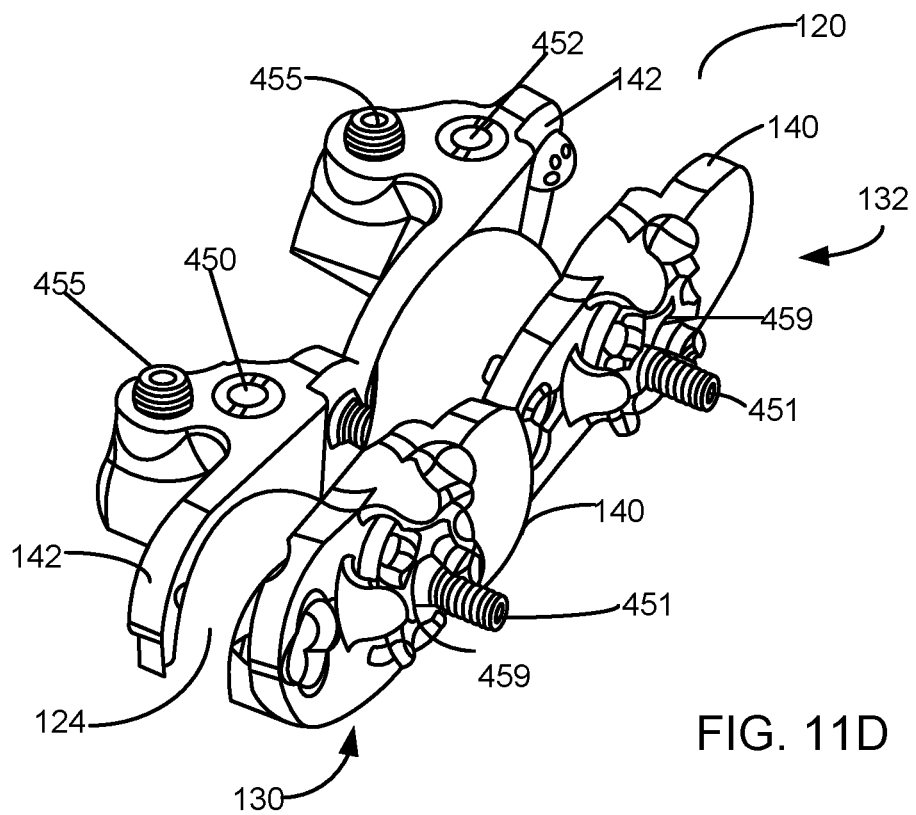
FIG. 11D is an isometric view of the alternative interspinous process spacing device implanted onto a spine, according to an example embodiment.

FIG. 11D illustrates two interspinous process spacing devices 130, 132 implanted with adjacent spinous processes 120, 122, 124. Although there is no overlap shown between the attachment sides of the two interspinous process spacing devices, it is appreciated that, in various embodiments, the attachment sides may overlap as further described herein.

Figure 12A:
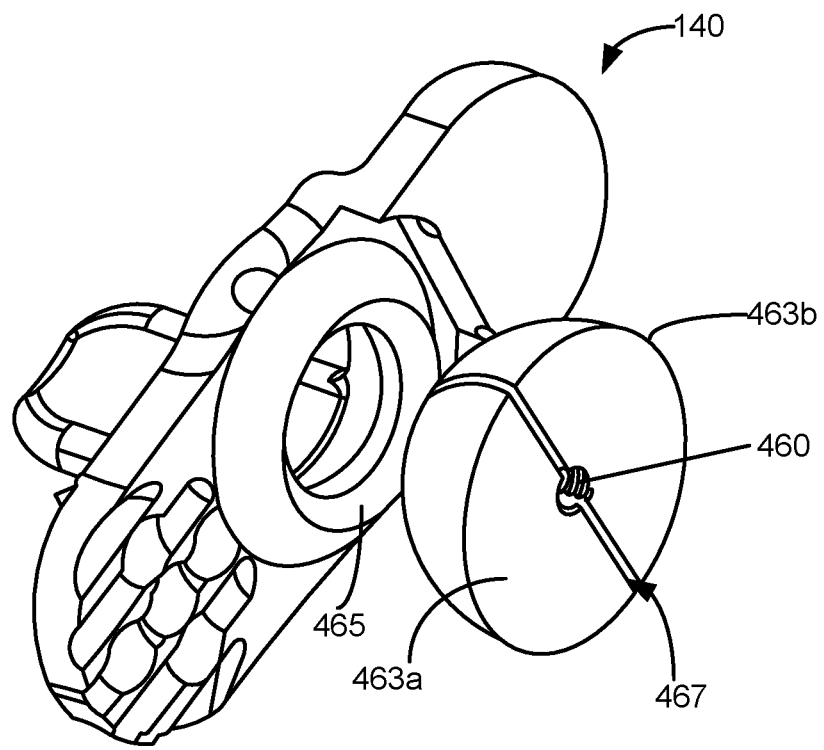
FIG. 12A is an isometric outside view of the first attachment side of the alternative interspinous process spacing device, according to an example embodiment.
Figure 12B:
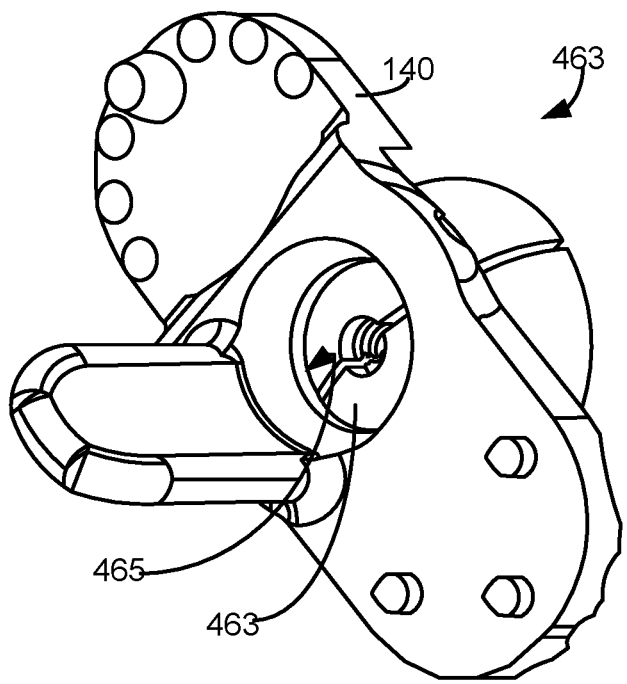
FIG. 12B is an isometric inside view of the first attachment side of the alternative interspinous process spacing device, according to an example embodiment.

FIGS. 12A-12B illustrate a different configuration of a nut, which may be used to threadably receive a threaded member, like the threaded member 451 described with reference to FIGS. 11A-11D, according to one embodiment. The hemispherical nut 463 may be formed to have a hemispherical shape (or other shape having an at least partially spherical or domed shape at its apex) for rotatably and pivotally fitting within a concave portion 465 of a first attachment side 140 of an interspinous process spacing device. Although not illustrated in FIGS. 12A-12B, in one embodiment, the first attachment side 140 may further include means for retaining the hemispherical nut with the first attachment side, particularly during implantation, which may include, but is not limited to, one or more clips, flanges, tabs, cages, straps, bands, springs, screws, and the like. For example, according to one embodiment, the first attachment side 140 may further include one or more flanges or tabs similar to the flanges or tabs 461b described with reference to FIG. 11C, which extend from the first attachment side to at least partially overlap the hemispherical nut 463, without unduly constraining its motion. Similarly, the hemispherical nut 463 may also contain one or more tabs or one or more detents adapted to cooperate with the retaining means extending from the first attachment side 140, which will prevent the hemispherical nut 463 from rotating when threading a threaded member therethrough, but still allow pivoting and rotation of the hemispherical nut 463.

Figure 4A:
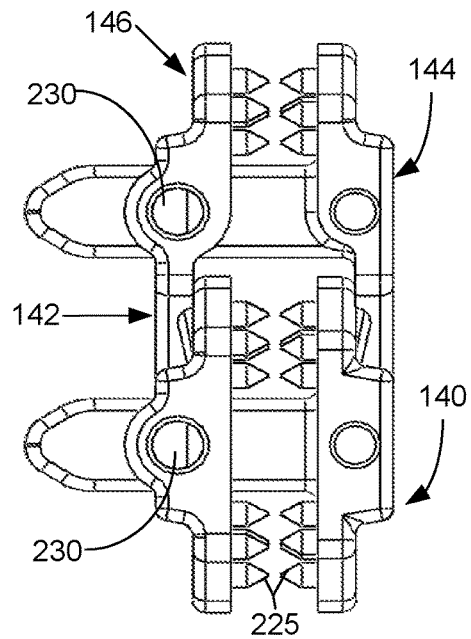
FIGS. 4A-4E are views of securing means integrated with interspinous process spacing devices, according to example base plate and overlapping link plate embodiments.
Figure 4B:
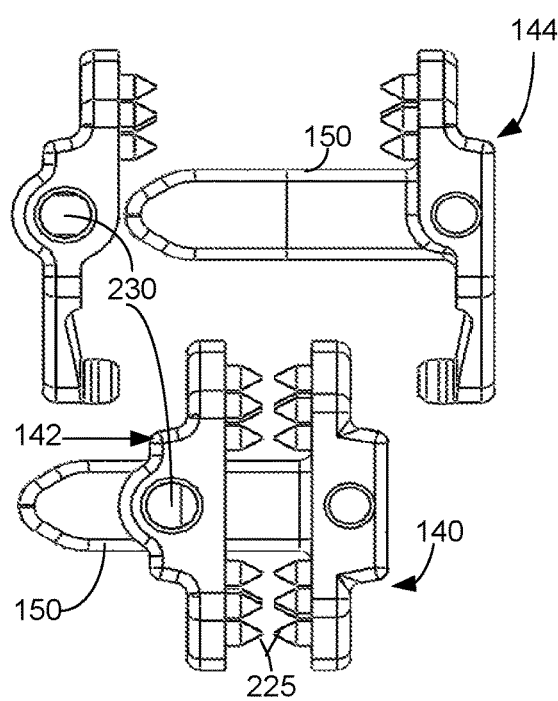
Figure 4C:
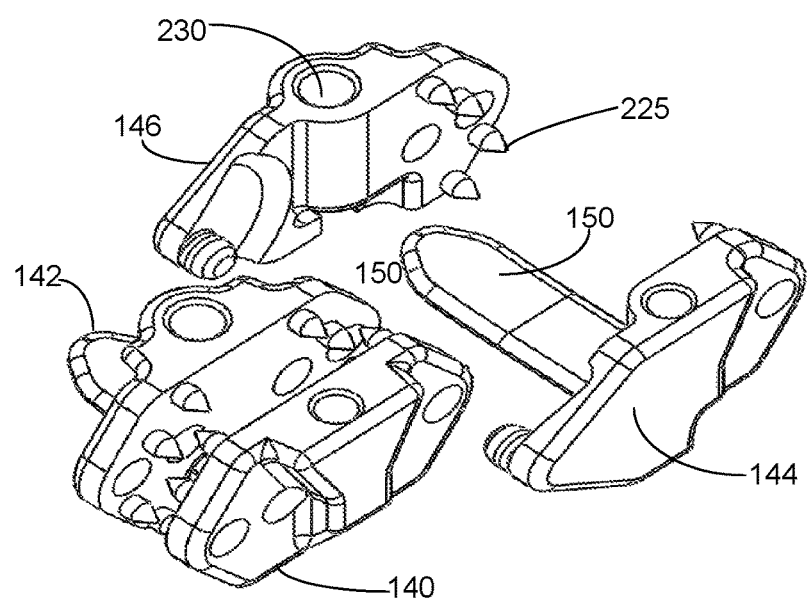
Figure 4D:
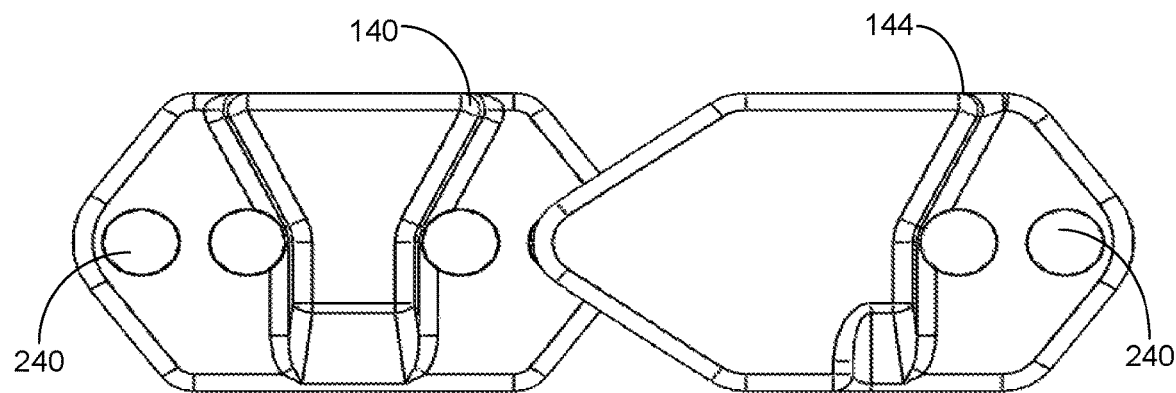
Figure 4E:
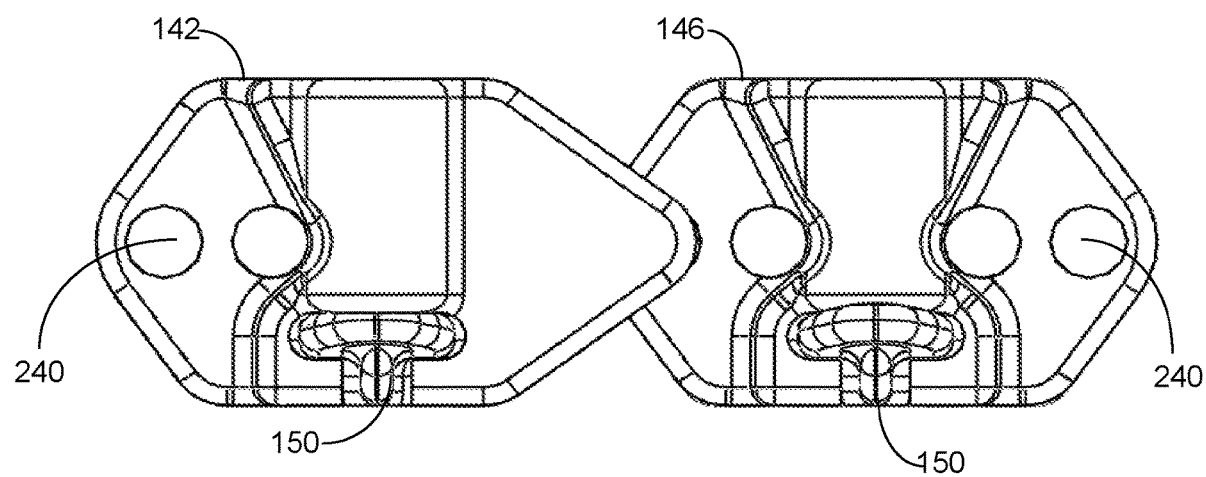
Figure 5A:
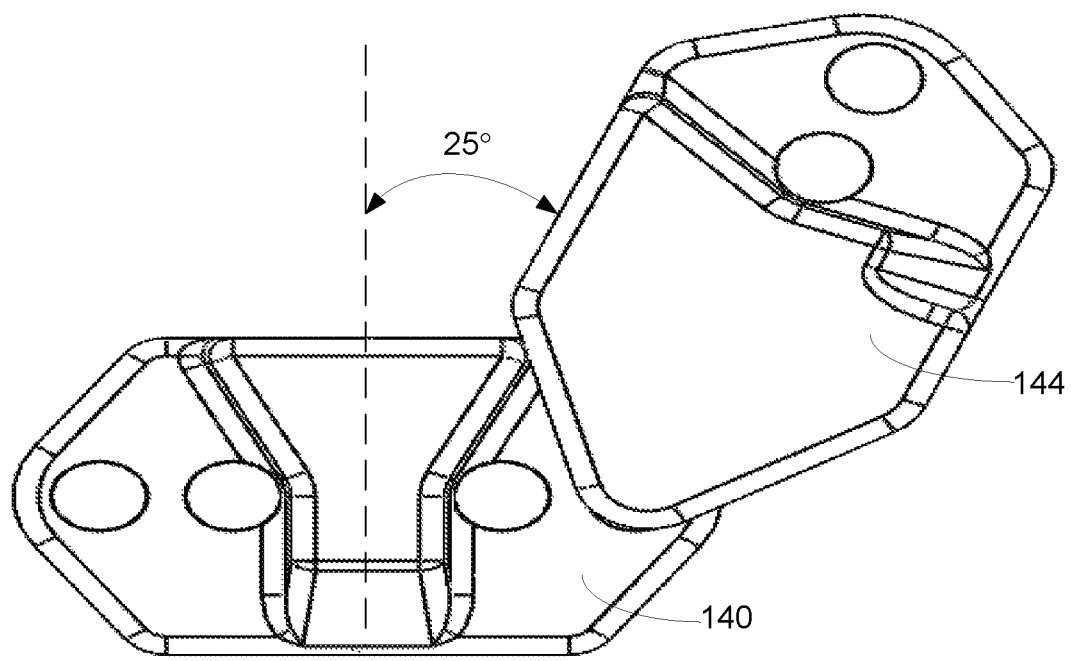
FIG. 5A is a back view of a first attachment side of an interspinous process spacing device having a base plate fastened to a link plate device showing maximum rotational range when connected to a first aperture, according to an example embodiment.
Figure 5B:
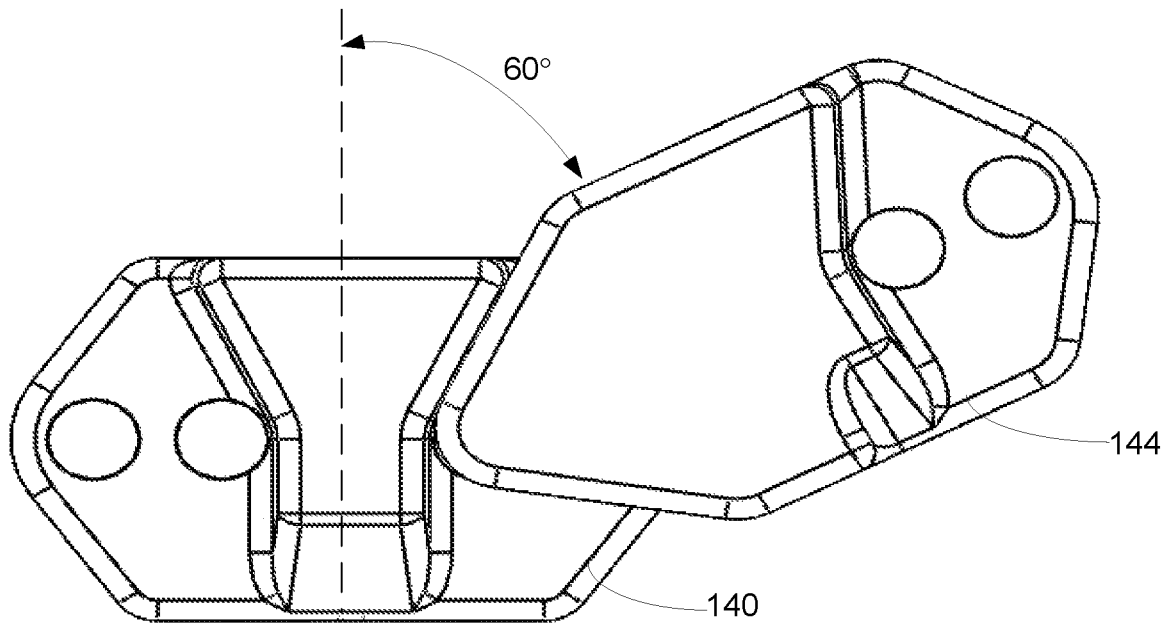
FIG. 5B is a back view of a first attachment side of an interspinous process spacing device having a base plate fastened to a link plate device showing maximum rotational range when connected to a second aperture, according to an example embodiment.
Figure 5C:
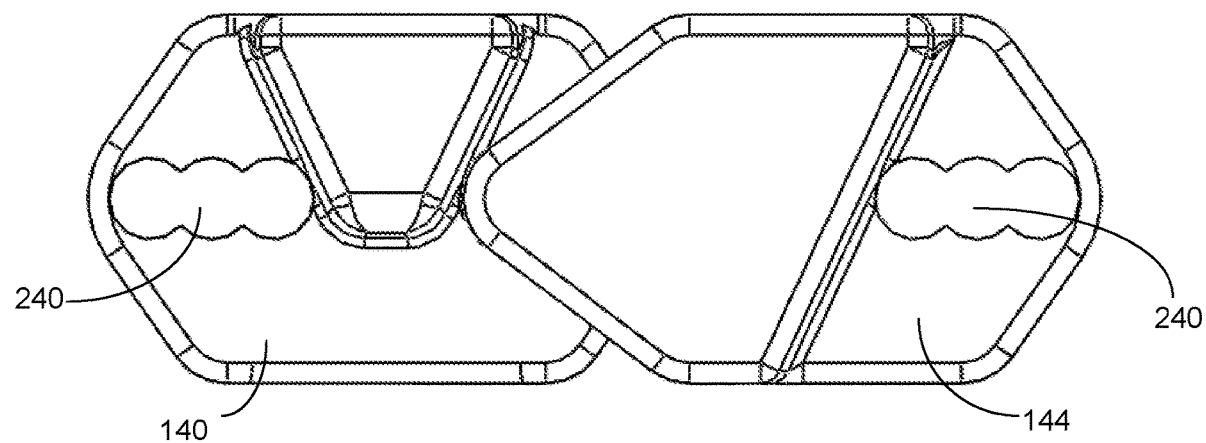
FIG. 5C is a back view of a first attachment side of an interspinous process spacing device having a base plate with multiple overlapping apertures in an inch-worm formation, for receiving a fastener of another link plate device, according to an example embodiment.

As shown in FIG. 12A, in one embodiment, the hemispherical nut 463 may have one or more slits 467 formed at least partially through its body. The one or more slits 467 permit the hemispherical nut 463 to expand for rapid insertion of a threaded member and subsequent collapsing on the threaded member to engage and secure with complementary threads 469 formed through the hemispherical nut 463. In one embodiment, the one or more slits 467 may be formed so as to extend only partially through the body of the hemispherical nut 463, and may stop before reaching the exterior facing surface of the hemispherical nut 463. Additional inward biasing or tightening members, such as, but not limited to, one or more bands, springs, screws, and the like, may optionally be included to bias or force the slits 467 together and around the threaded member. In another embodiment, as shown in FIG. 12A, the hemispherical nut 463 may be formed from at least two portions 463a, 463b (e.g., two equal halves), which are connected at or near the exterior facing end of the hemispherical nut 463. Any means may be used to connect the two (or more) portions 463a, 463b of the hemispherical nut 463, such as, but not limited to, one or more screws, bolts, welding, tacking, clamps, bands, pins, flanges, tabs, springs, and the like. In one embodiment, one or more spring members may be contained between the two portions 463a, 463b such that the spring member biases the portions in a more separated or open position and will be compressed to a more closed position to engage the threads 469 with a threaded member when the hemispherical nut 463 is pushed into the concave portion 465 of the attachment side. FIG. 4B illustrates the first attachment side 140 from the interior side, showing the fitment of the hemispherical nut 463 within the concave portion 465. In one embodiment, such as is shown by example in FIGS. 4M and 4R, the receiving side of the hemispherical nut 463 at or near the apex is at least partially concave to guide and direct the threaded member into the receiving threads of the hemispherical nut. In another embodiment, a quick release mechanism may further optionally be included, which will act to separate the hemispherical nut 463 to allow for unimpeded or minimally impeded removal of the threaded member from the hemispherical nut 463.

Figure 12C:
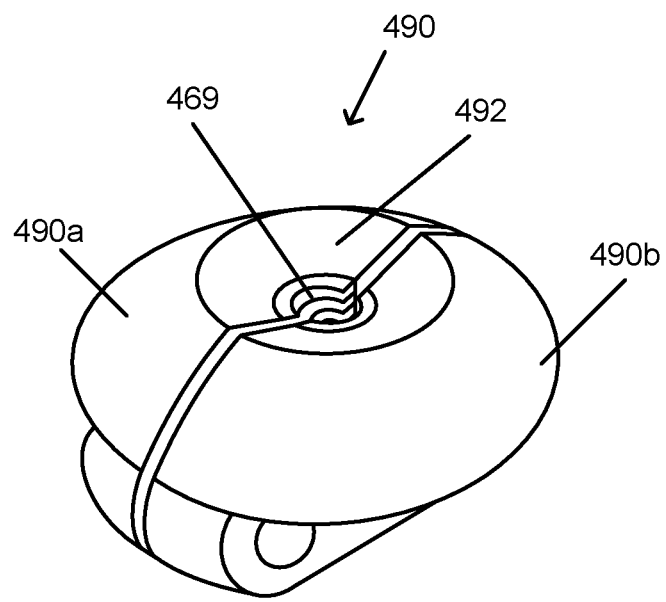
FIG. 12C is an isometric view of a floating receiving member of the alternative interspinous process spacing device, according to an example embodiment.
Figure 12D:
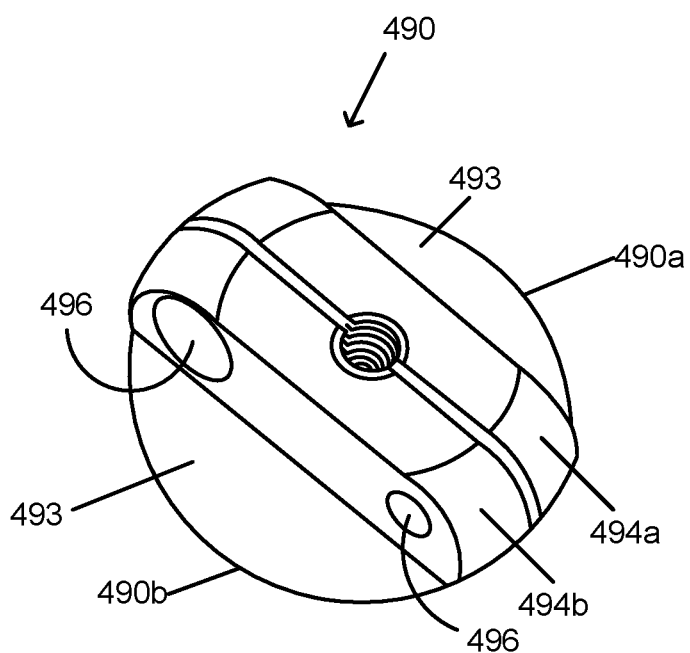
FIG. 12D is an isometric view of a floating receiving member of the alternative interspinous process spacing device, according to an example embodiment.

FIGS. 12C-12I illustrate yet another embodiment of a floating receiving member configured as a hemispherical nut formed from two separate halves. In this embodiment, as shown in FIG. 12C, a hemispherical nut 490 includes a first half 490a and a second half 490b. According to this embodiment, the hemispherical nut 490 includes a concave portion 492 formed at its apex, which serves to guide and direct the threaded member into the receiving threads 469 of the hemispherical nut 490. FIG. 12D illustrates the exterior facing side of the hemispherical nut 490 and means for retaining the two halves 490a, 490b together. According to this embodiment, two opposing sides are recessed, creating recessed portions 493 and first and second ridges 494a, 494b through which a combination of screws and springs are inserted to hold the two halves 490a, 490b together. Moreover, the recessed portions 493 provide a surface against which retaining tabs or other retaining means are placed to retain the hemispherical nut with the first attachment side, as further described with reference to FIG. 12I.

Figure 12E:
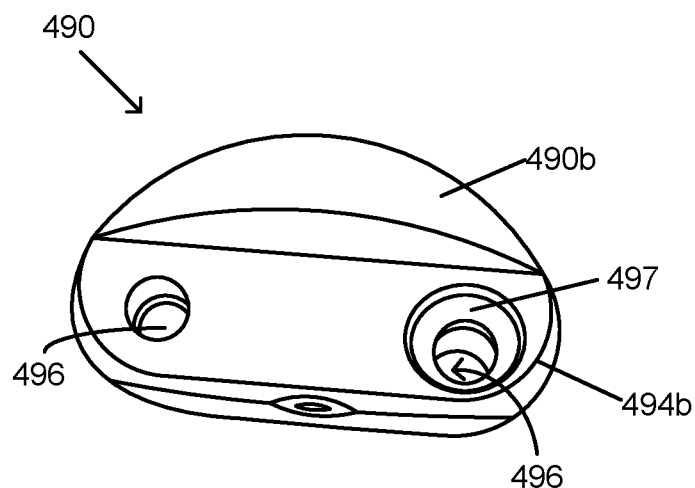
FIG. 12E is an isometric view of a floating receiving member of the alternative interspinous process spacing device, according to an example embodiment.
Figure 12F:
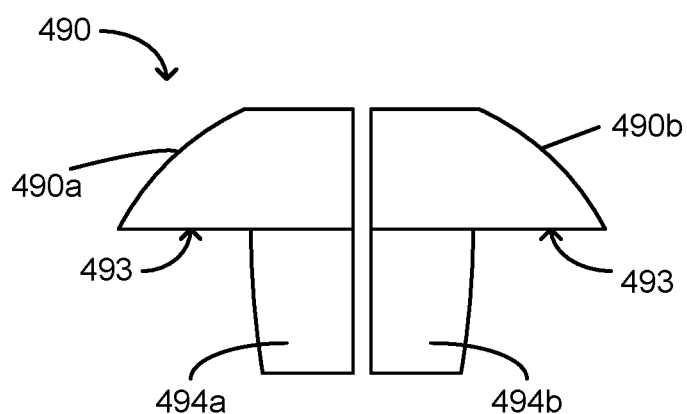
FIG. 12F is a side view of a floating receiving member of the alternative interspinous process spacing device, according to an example embodiment.

FIG. 12E illustrates a side view of the hemispherical nut 490 according to this embodiment. As shown by this side view, the second ridge 494b includes a pair (or any number) of aligned apertures 496 extending through the ridges 494a, 494b. In one embodiment, each ridge 494a, 494b further includes an additional recessed lip 497 formed with one of the apertures 496 for receiving and retaining a spring that creates an inward biasing force for retaining the two halves 490a, 490b together. In this embodiment, only a single recessed lip 497 is formed on each ridge 494a, 494b such that one aperture 496 has a recessed lip 497 formed on the first ridge 494a, and the other aperture 496 has a recessed lip 497 formed on the second ridge 494b and with the opposite. This allows for springs to be inserted on opposite sides of the ridges 494a, 494b and through different apertures, as shown in FIG. 12I. FIG. 12F illustrates a side profile view of the hemispherical nut 490, showing the slit formed between the two halves and the profile of the hemispherical shape and the ridges 494.

Figure 12G:
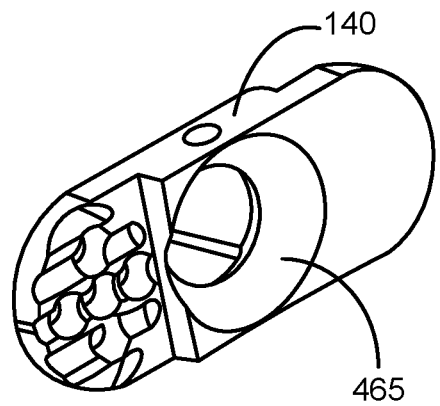
FIG. 12G is an isometric view of the interface of a floating receiving member integrating with the first attachment side of the alternative interspinous process spacing device, according to an example embodiment.
Figure 12H:
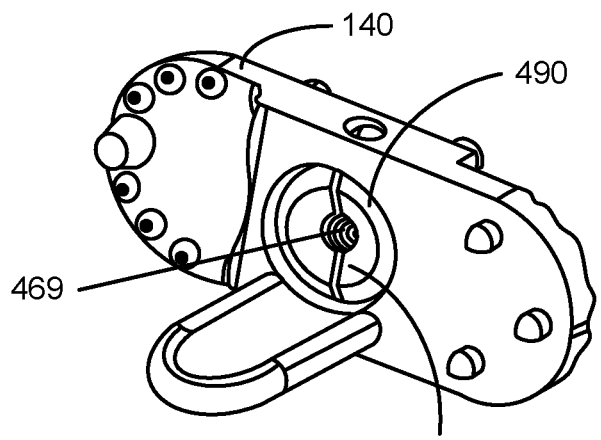
FIG. 12H is an inner isometric view of the interface of a floating receiving member integrating with the first attachment side of the alternative interspinous process spacing device, according to an example embodiment.
Figure 12I:
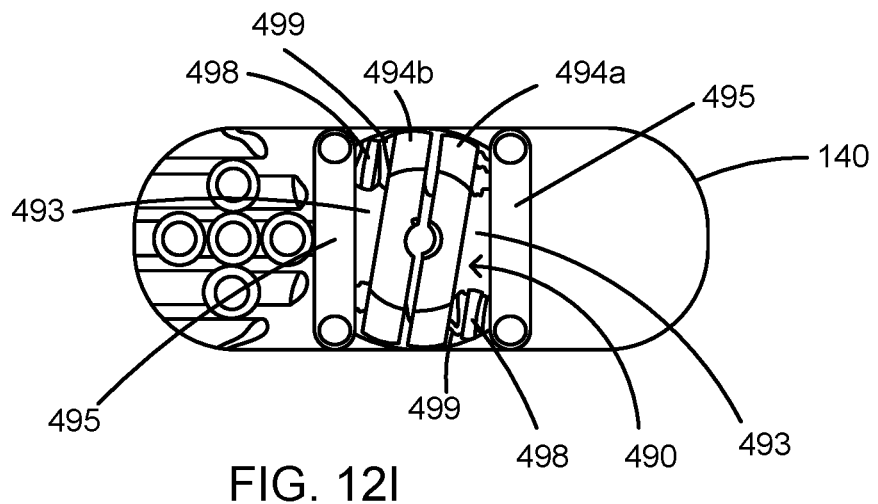
FIG. 12I is an outside rear view of the interface of a floating receiving member integrating with the first attachment side of the alternative interspinous process spacing device, according to an example embodiment.

FIGS. 12G-12I illustrate a first attachment side 140 and the interoperability of the hemispherical nut 490 therewith, according to one embodiment. FIG. 12G shows the exterior-facing surface of the first attachment side 140, which includes a concave portion 465. The concave portion 465 allows the hemispherical nut 490 to be pivotally and rotatably housed therein, allowing for independent movement of the two attachment sides when implanted to account for different spinous process size and anatomy. FIG. 12H shows the interior facing side of the first attachment side 140 with the hemispherical nut 490 contained within the concave portion of the first attachment side 140. As described above and as is shown in FIG. 12H, the hemispherical nut 490 itself can further include a concave portion 492 that facilitates guiding a threaded member centrally into the threads 469 of the hemispherical nut 490.

FIG. 12I illustrates the exterior-facing surface of the first attachment side 140 having the hemispherical nut 490 retained therein. According to this embodiment, the first attachment side includes one or more retaining members 495 for retaining the hemispherical nut 490 within the concave portion 465 of the first attachment side 140, such as, but not limited to, tabs, arms, flanges, bands, screws, and the like. In this embodiment, the retaining members 495 include two arms attached to the attachment side 140 and extending over the recessed portions 493 of each half of the hemispherical nut 490. The retaining members 495 may be removably attached to the first attachment side 140, such as via one or more screws and the like, or may be permanently affixed or integrated with the first attachment side 140, such as if the hemispherical nut 490 and the first attachment side 140 were manufactured together, or if the hemispherical nut 490 is pressure fitted within the retaining members 495. Moreover, in one embodiment, the retaining members 495 are not secured against the recessed portions 493, but instead provide a loose fit of the hemispherical nut 490 within the attachment side 140 to allow rotating and pivoting.

FIG. 12I also illustrates screws 498 and springs 499 inserted through the apertures 496 of the ridges 494a, 494b. As is shown as one example configuration, the first ridge 494a includes one spring 499 fit within the recessed lip 497 and retained by a screw 498 extending through the set of apertures and both ridges 494a, 494b. The second ridge 494b similarly includes one spring fit within the recessed lip 497 and retained by a screw 498 extending through the other set of apertures and through both ridges 494a, 494b. According to this configuration, each screw 498 is inserted in opposite directions through the ridges 494a, 494b, retaining a spring 499 on opposite sides of the hemispherical nut 490. However, other screw 498 and spring 499 configurations may be provided, or in some embodiments, a spring may not be included.

It is appreciated that, according to other embodiments, any of the features described with reference to FIGS. 12B-12I may be included in any other embodiment described herein, and any other feature described herein may be included with the embodiments of FIGS. 12B-12I. For example, a quick release mechanism may be included, other floating receiving member configurations may be used, and the like.

Figure 12J:
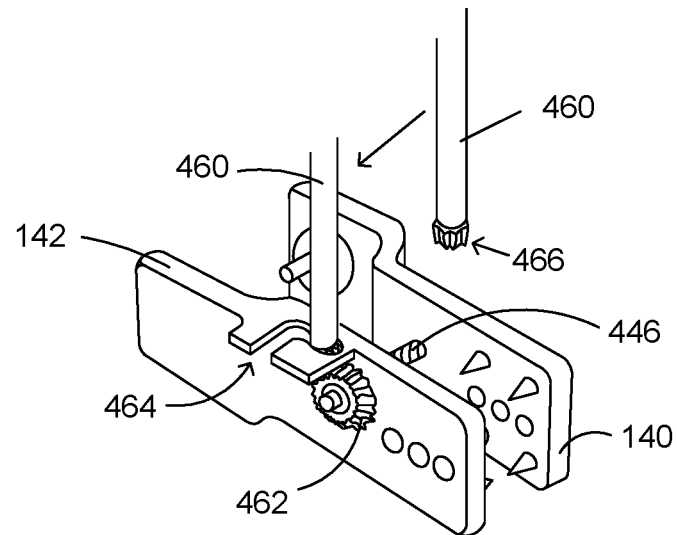
FIG. 12J is an isometric view of an alternative interspinous process spacing device, according to an example embodiment.

FIG. 12J illustrates yet another embodiment of a securing means used to tighten the opposing attachment sides 140, 142 on adjacent spinous processes. This embodiment is configured similar to the embodiment illustrated in and described with reference to FIG. 10; although, instead of an integrated shaft and gear to drive the nut, a removable instrument 460 is used to engage and rotate a geared nut 462 threaded over an end of the threaded shaft 446. Because the instrument 460 is removable and not integrated with the interspinous process spacing device, an additional positioning track 464 is integrated with the second attachment side. The positioning track 464 guides the instrument 460 to align its geared tip 466 with the teeth extending from the surface of the geared nut 462. Although the positioning track 464 is illustrated as being configured in an L shape, any other track configuration may be used. For example, in another embodiment, the positioning track 464 may be configured as a hole aligned to cause the geared tip 466 to mesh with the geared nut. Moreover, in one embodiment, the positioning track 464 may be formed with thick side walls to facilitate maintaining alignment of the instrument 460 within the positioning track and in a vertical (or other desirable) orientation by providing increased surface area to guide the instrument 460. Accordingly, operably meshing the geared tip 466 of the instrument 460 with the geared nut 462 and turning the instrument causes the geared nut 462 to thread on and off of the threaded shaft 446, moving the second attachment side 142 toward the first attachment side.

As described above, the fit of the threaded shaft 446 within the aperture of the second attachment side 142 may be a tight or loose fit. In addition, although FIG. 12J shows a particular orientation of the threaded shaft 446 and the positioning track 464, any other orientation and/or configuration may be used.

Figure 12K:
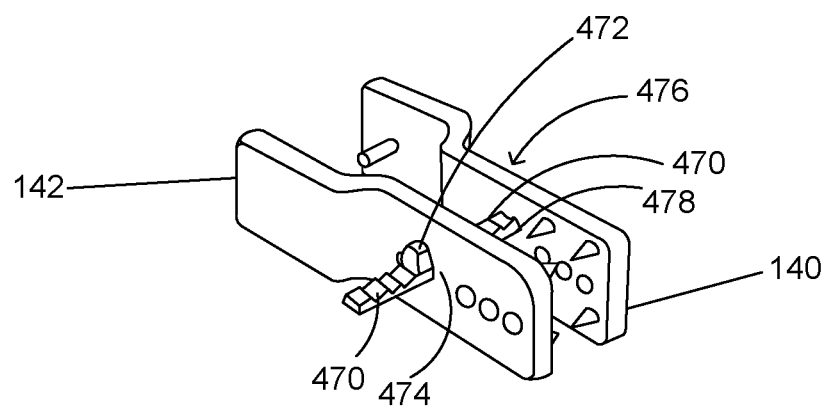
FIG. 12K is an isometric view of an alternative interspinous process spacing device integrating an alternative advancement mechanism for the first and second attachment sides, according to an example embodiment.

FIG. 12K illustrates yet another embodiment of a securing means used to tighten the opposing attachment sides 140, 142 on adjacent spinous processes. According to this embodiment, a geared rack 470 and a ratchet member 472 operate in a manner similar to known cable tie mechanisms. In this embodiment, the geared rack 470 extends from the first attachment side 140 through an aperture 474 formed through the second attachment side 142. The second attachment side 142 includes a ratchet member 472 formed on at least one of its surfaces (shown on the outward-facing surface, but may be on the inward surface in other embodiments). The ratchet member 472 operably engages with the teeth on the geared rack 470 and permits movement in one direction—the direction toward the opposing attachment side 140. The operation of the ratchet member 472, however, restricts movement in the opposite direction (e.g., loosening of the attachment sides 140, 142). In one embodiment, a release mechanism may be included to selectively allow movement in the opposite direction. Accordingly, by tightening the second attachment side 142 toward the first attachment side 140, the ratchet member 472 secures the position of the two sides relative to each other. In one embodiment, a separate insertion instrument (e.g., pliers-type device) is used to achieve enough mechanical advantage to tighten the attachment sides 140, 142 on the spinous processes. An example of such a clamping device is illustrated in and described with reference to FIGS. 13-20 below.

According to one embodiment, the geared rack 470 may be slideably positioned through both an aperture 478 formed in the first attachment side 140 and the aperture 474 of the second attachment side 142, having a head 476 on one end which will abut the outer surface of the first attachment side 140. In one embodiment, the head 476 is domed on the side that will abut the attachment side (i.e., adjacent to the shaft), which permits the geared rack 470 to rotate at least partially within the aperture 478 and allow the two attachment sides 140, 142 to vary in their angular orientation relative to each other and relative to the geared rack 470. In one embodiment, the aperture 478 of the first attachment side 140 is also beveled or bored to accommodate the domed shape of the geared rack 470. Moreover, in one embodiment, the aperture 474 formed in the second attachment side 142 can form a relatively tight fit with the geared rack 470 to provide secure engagement of the ratchet member 472 against the geared rack 470. An aperture 474 creating a tight fit causes the second attachment side 142 to have a substantially constant angular relationship with the geared rack 470 (e.g., perpendicular); however, a looser fit between the head 476 and the aperture 478 in the first attachment side 140 still allows relative angular variation between the two attachment sides (e.g., to accommodate different thicknesses of adjacent spinous processes).

In addition, although FIG. 12K shows a particular orientation of the geared rack 470 and the ratchet member 472, any other orientation and/or configuration may be used.

Figure 12L:
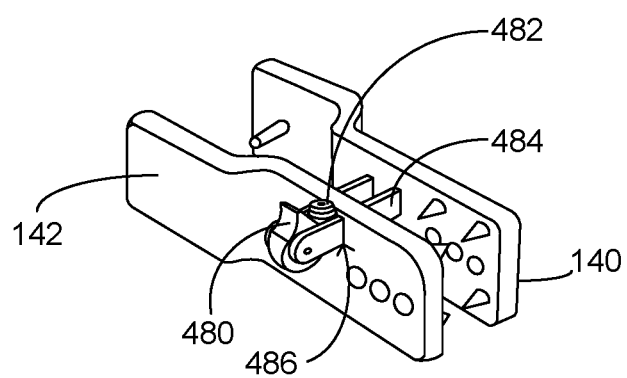
FIG. 12L is an isometric view of an alternative interspinous process spacing device integrating an alternative advancement mechanism for the first and second attachment sides, according to an example embodiment.
Figure 13A:
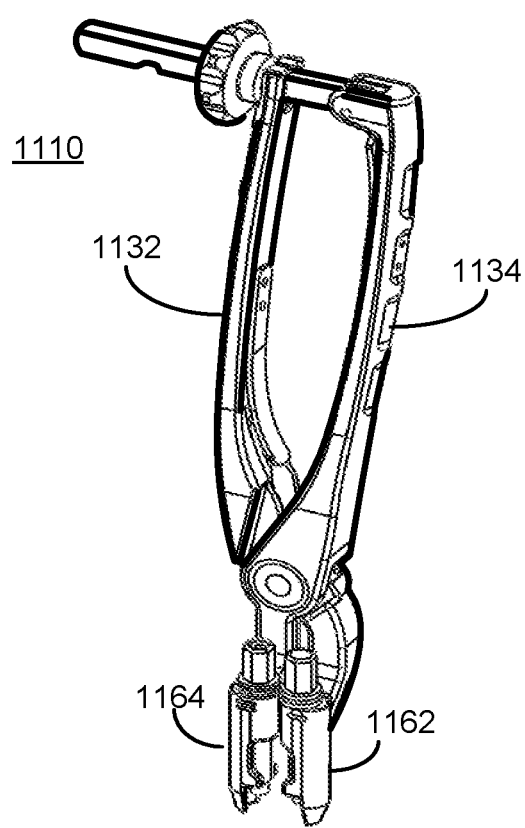
FIG. 13A is an isometric view of a top down or universal surgical instrument for implanting and compressing/advancing two attachment sides of an interspinous process spacing device, according to an example embodiment.
Figure 13B:
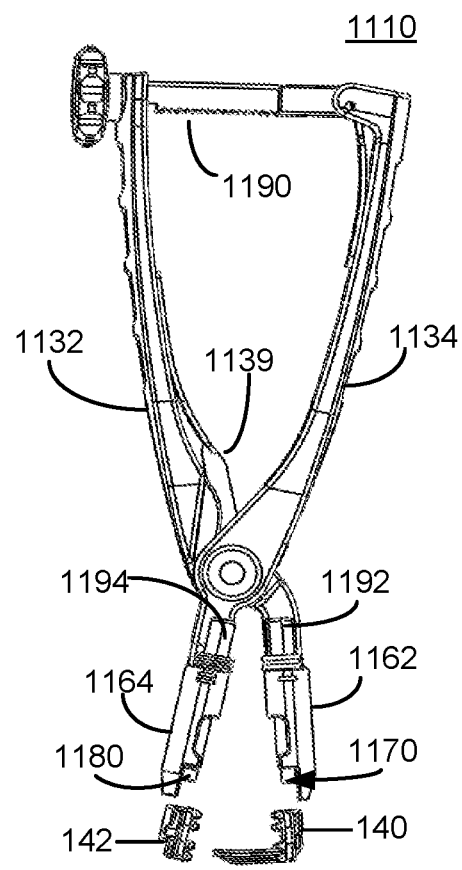
FIG. 13B is a side view of a universal surgical instrument for implanting and compressing/advancing two attachment sides of an interspinous process spacing device, according to an example embodiment.
Figure 13C:
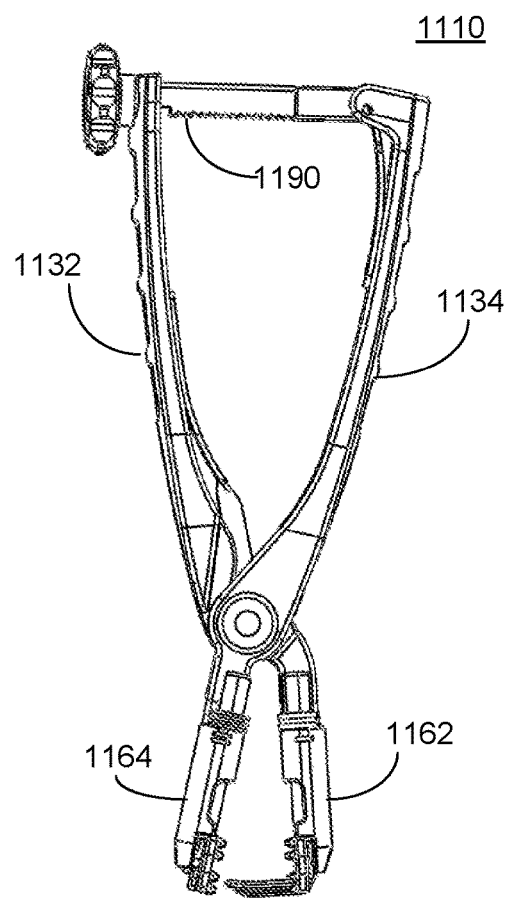
FIG. 13C is a side view of a universal surgical instrument for implanting and compressing/advancing two attachment sides of an interspinous process spacing device, according to an example embodiment.
Figure 13D:
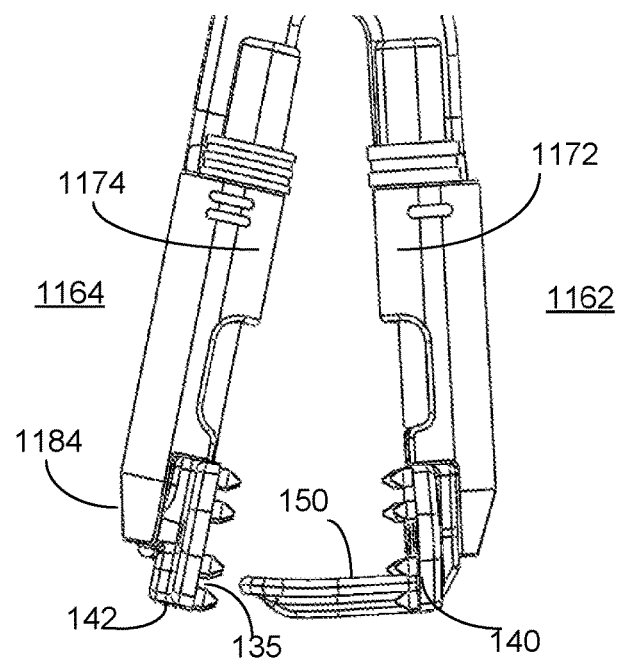
FIG. 13D is a detailed side view of a universal surgical instrument for implanting and compressing/advancing two attachment sides of an interspinous process spacing device, according to an example embodiment.
Figure 14D:
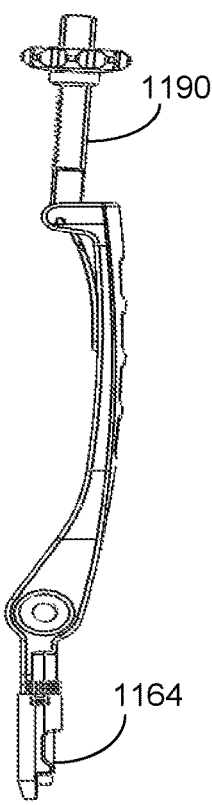
FIG. 14D is a side view of a second arm of the example embodiment.
Figure 14E:
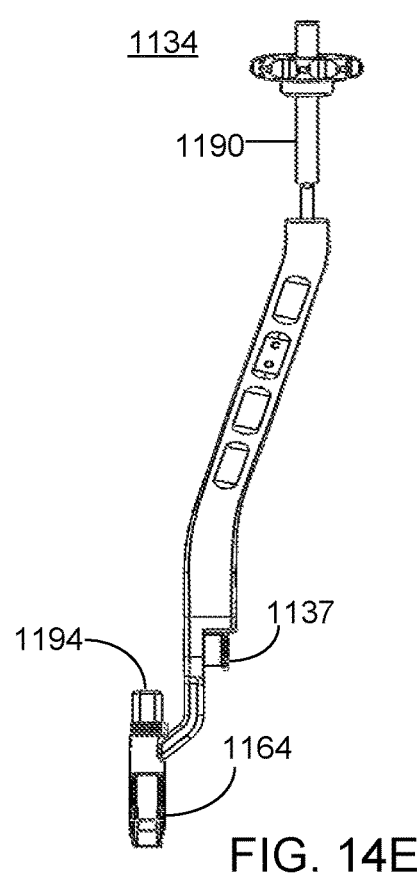
FIG. 14E is an alternative side view of a second arm of the example embodiment.
Figure 14F:
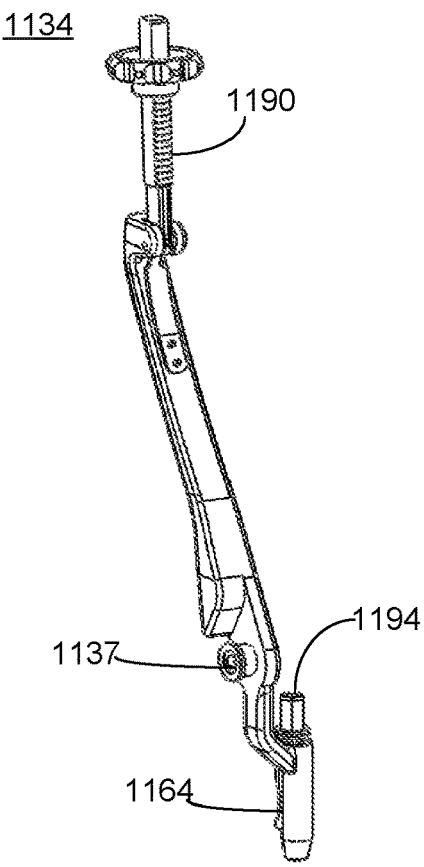
FIG. 14F is an alternative side view of a second arm of the example embodiment.
Figure 15A:
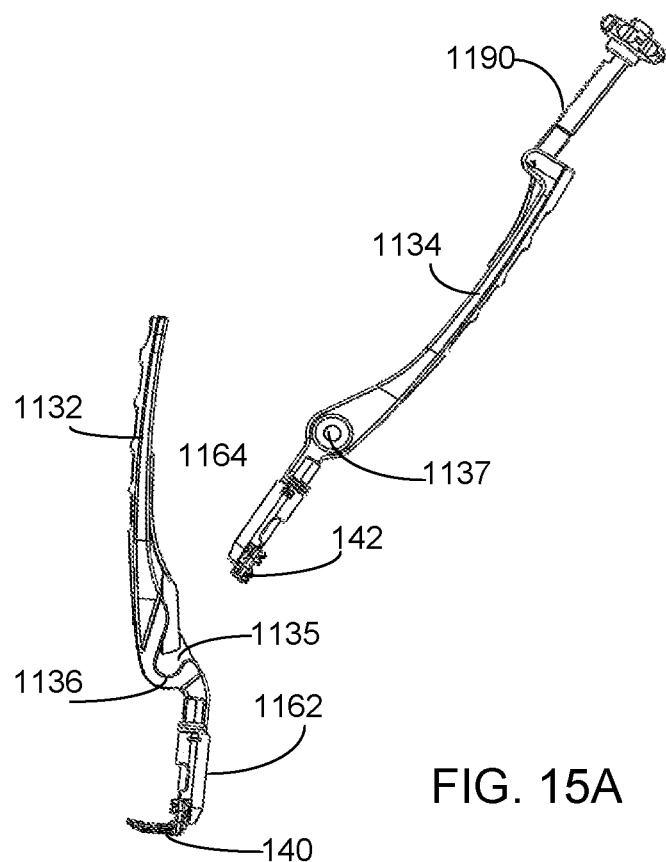
FIG. 15A is a side view of a separate first and second arm of a top down or universal surgical instrument for implanting and compressing/advancing two attachment sides of an interspinous process spacing device, according to an example embodiment.
Figure 15B:
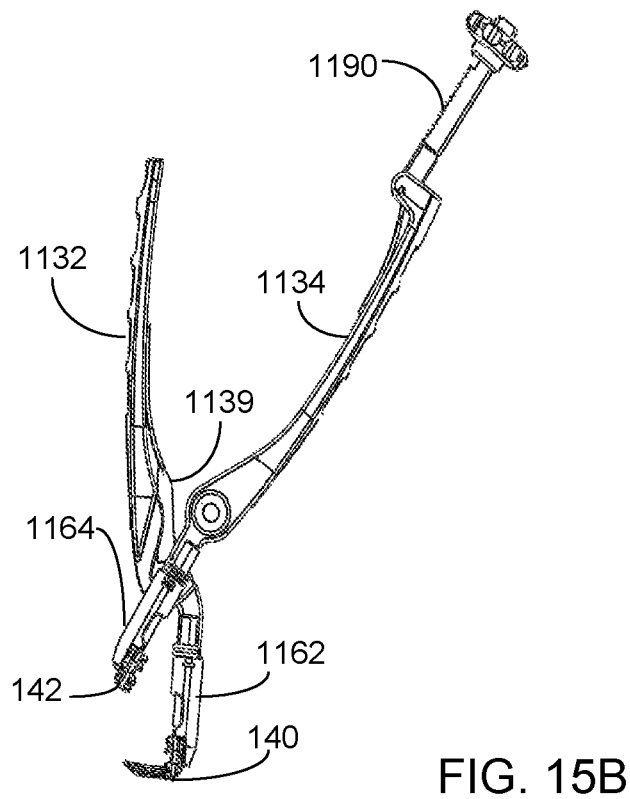
FIG. 15B is a side view of a further advanced (almost engaged) first and second arm of a top down surgical instrument for implanting and compressing/advancing two attachment sides of an interspinous process spacing device, according to an example embodiment.
Figure 16A:
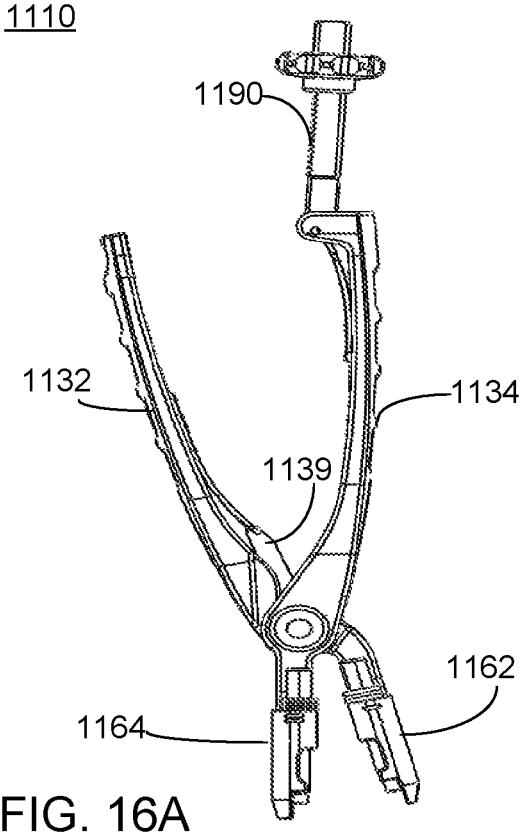
FIG. 16A is a side view of a top down or universal surgical instrument for implanting and compressing/advancing two attachment sides of an interspinous process spacing device showing an unengaged mechanical actuation means, according to an example embodiment.
Figure 16B:
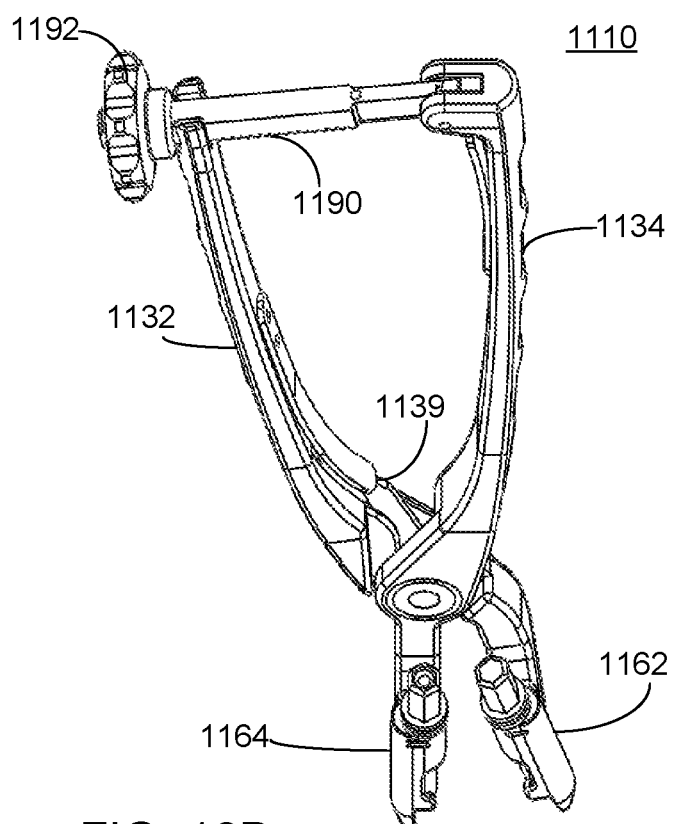
FIG. 16B is a side view of a top down surgical instrument for implanting and compressing/advancing two attachment sides of an interspinous process spacing device showing an engaged mechanical actuation means, according to an example embodiment.
Figure 16C:
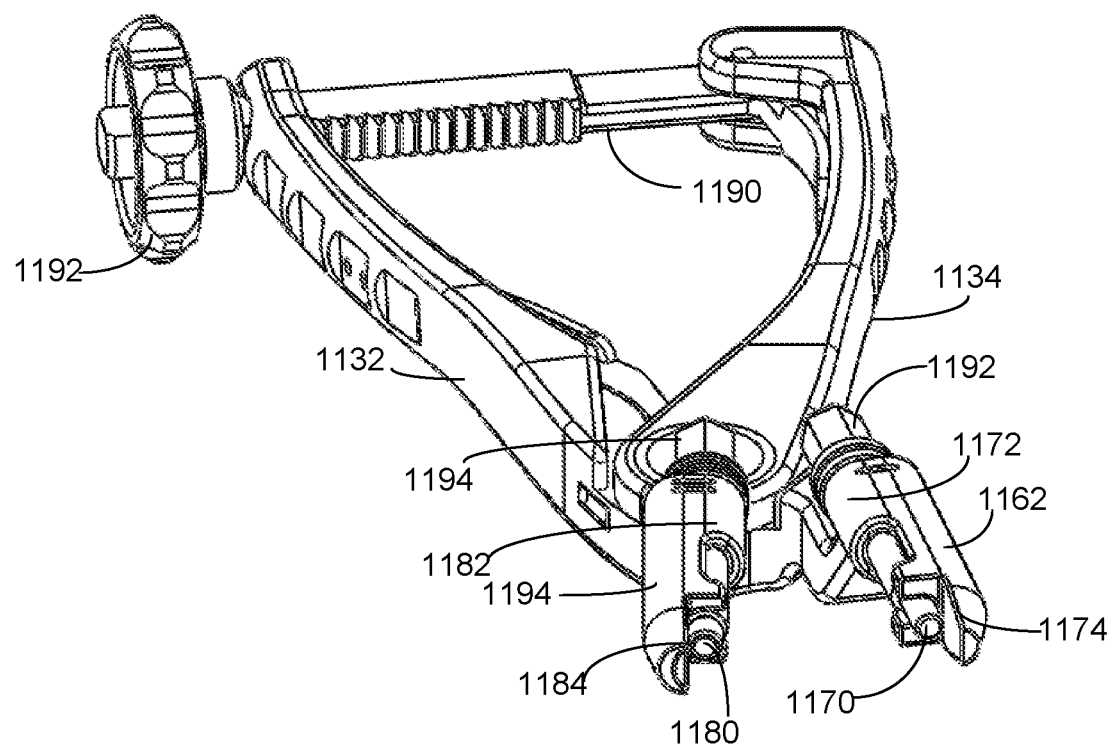
FIG. 16C is an isometric view of a top down surgical instrument for implanting and compressing/advancing two attachment sides of an interspinous process spacing device showing the mechanical actuation means, according to an example embodiment.
Figure 17A:
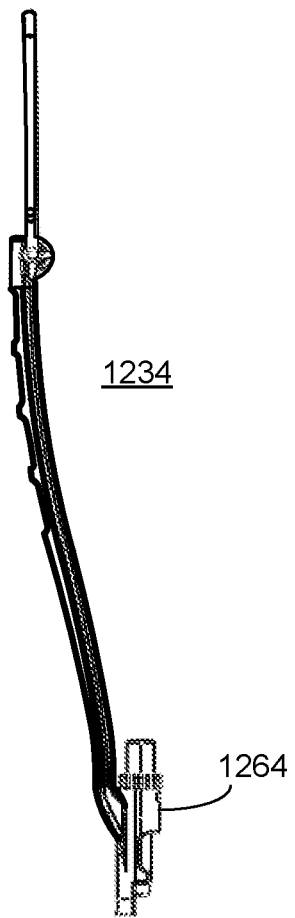
FIG. 17A is a side view of a second inserter arm of a surgical instrument for implanting an interspinous process spacing device, according to an example embodiment.
Figure 17B:
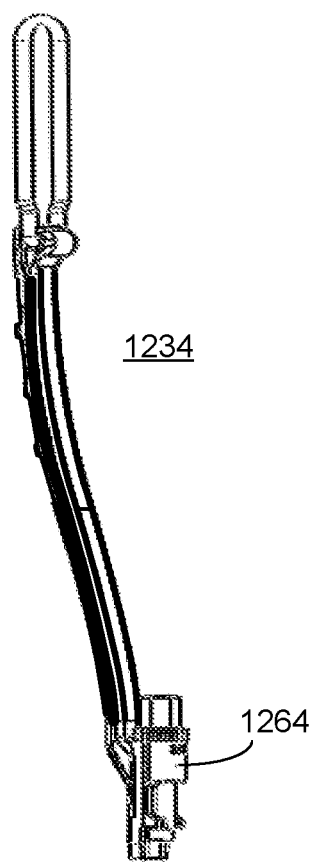
FIG. 17B is an alternative side view of the second inserter arm of the example embodiment.
Figure 17C:
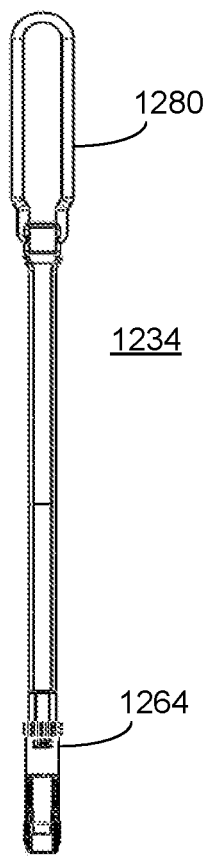
FIG. 17C is an alternative side view of the second inserter arm of the example embodiment.
Figure 17D:
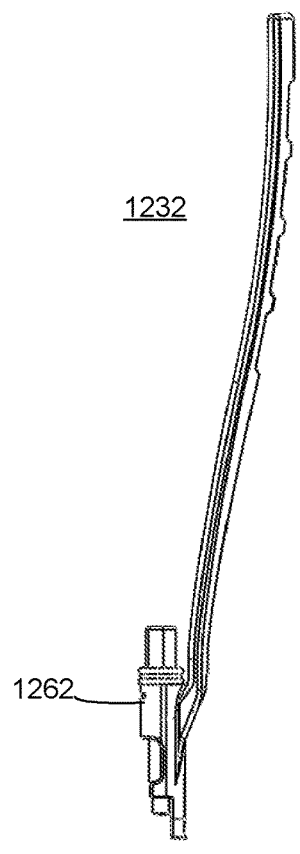
FIG. 17D is a side view of the first arm of the example embodiment.
Figure 17E:
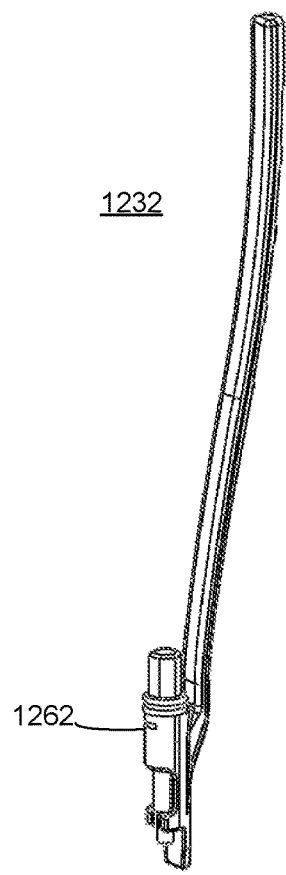
FIG. 17E is an alternative side view of a first arm of the example embodiment.
Figure 17F:
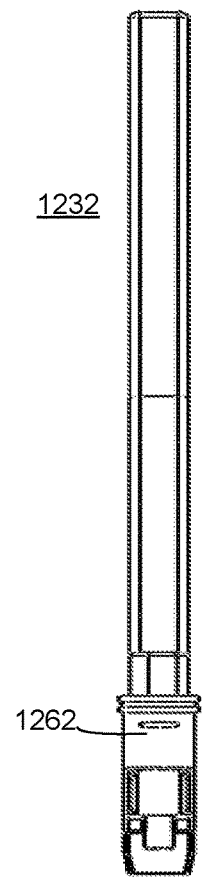
FIG. 17F is an alternative side view of a first arm of the example embodiment.
Figure 18A:
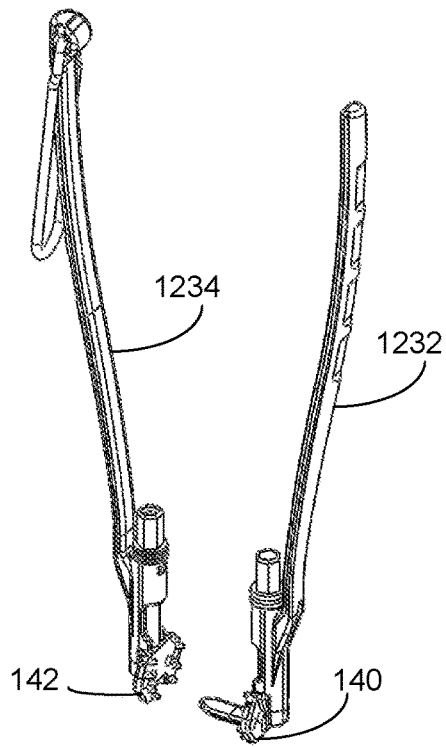
FIG. 18A is an isometric view of a first and second inserter arm of a surgical instrument for implanting an interspinous process spacing device, according to an example embodiment.
Figure 18B:
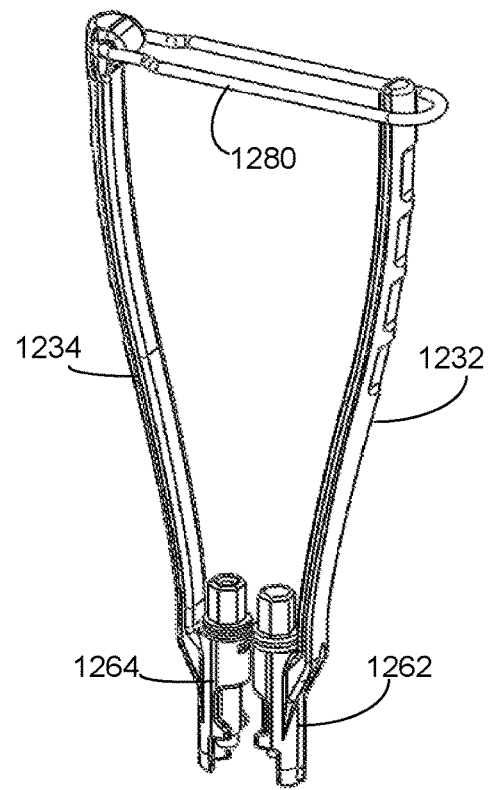
FIG. 18B is a view of the retained first and second inserter arms of the example embodiment.
Figure 18C:
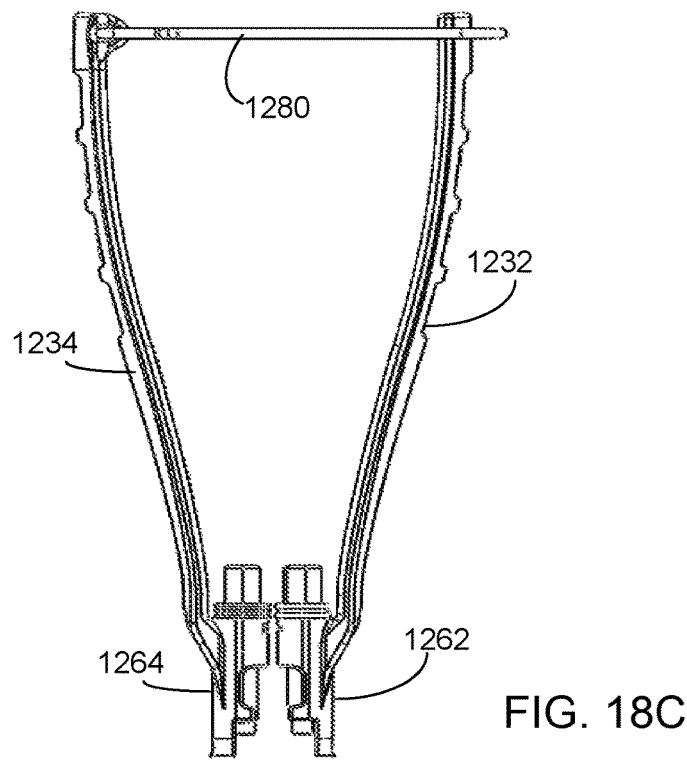
FIG. 18C is a side view of the retained first and second inserter arms of the example embodiment.
Figure 19A:
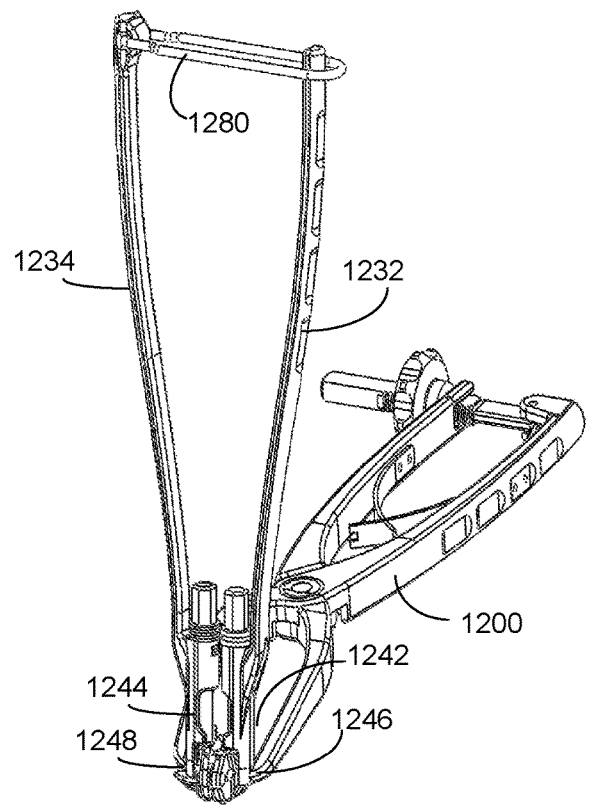
FIG. 19A is an isometric view of a compressor tool positioning first and second inserter arms of a surgical instrument for implanting an interspinous process spacing device, according to an example embodiment.
Figure 19B:
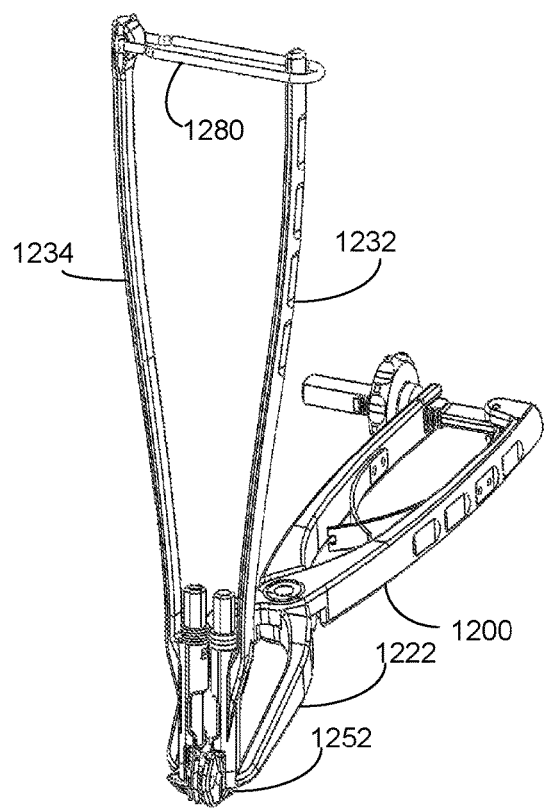
FIG. 19B is an isometric view of a compressor tool positioning first and second inserter arms of a surgical instrument for implanting an interspinous process spacing device, according to an example embodiment.

FIG. 12L illustrates yet another embodiment of a securing means used to tighten the opposing attachment sides 140, 142 on adjacent spinous processes. According to this embodiment, a geared cam 480 is actuated by a shaft and gear 482 operably meshed with the geared cam 480 to cause the lobe of the cam to exert a force against a second attachment side 142, in turn causing it to move toward the first attachment side 140. According to this embodiment, a track 484 (which may be a spacer tray or a separate track) extends from the first attachment side 140 and through an aperture 486 in the second attachment side 142. The geared cam 480 is pivotally fixed to the track 484 via an axle running through the cam 480. Thus, when the shaft and gear 482 is turned, the cam 480 rotates about the axle and the lobe of the cam 480 moves toward or away from the outer surface of the second attachment side 142, causing the second attachment side 142 to move along the track 484 toward or away from the first attachment side 140.

As described above, the fit of the track 484 (and/or spacer tray) within the aperture of the second attachment side 142 may be a tight or loose fit. In addition, although FIG. 12L shows a particular orientation of the geared cam 480, the threaded member track 484, and the shaft and gear 482, any other orientation and/or configuration may be used.

Although not illustrated in every figure, any of those securing means illustrated may further include one or more set screws, securing the second attachment side 142 (or whichever attachment side slides over the spacer tray 150) to the spacer tray 150 or the geared rack, threaded member, threaded bolt, track, etc. when tightened to fix the relative location of the two attachment sides 140, 142. A set screw assembly can extend from the outer surface of the second attachment side 142 and through which a set screw is threaded to exert pressure on, and thus to secure the attachment side 142 to, the spacer tray 150. In other embodiments, more than one set screw assembly can be employed. Moreover, the orientation of the set screw assembly can vary.

In addition, although the embodiments illustrated show the securing means oriented as generally extending from the first attachment side 140 and through the second attachment side 142, it is appreciated that in other embodiments the opposite configuration can be provided, in which the securing means extends from the second attachment side 142 and through an aperture formed through the first attachment side 140.

FIGS. 13-20 illustrate embodiments of a separate insertion instrument (implant inserter) 1110 that is optionally used to exert a clamping pressure on each of the attachment sides 140, 142 when securing the interspinous process spacing device in place against the spinous processes. In one embodiment, the attachment sides 140, 142 may include apertures or indentations shaped and positioned to receive the working ends of the insertion instrument 1110, such that the insertion instrument 1110 may grasp the attachment sides 140, 142, and operable to facilitate aligning and maintaining the insertion instrument 1110 in position. Accordingly, once the two attachment sides 140, 142 are clamped in a closed configuration, the securing means 1120 (e.g., any of those illustrated in and described with reference to FIGS. 1-12 and, optionally or alternatively, a set screw) is operated to secure the second attachment side 142 in place relative to the spacer tray 150 and the first attachment side 140. It is appreciated that any insertion instrument 1110 suitable for applying a clamping force on opposite attachment sides may be used.

For example, FIGS. 13-16 illustrate another embodiment of an insertion instrument 1130 having a different configuration. According to this embodiment, a second arm 1134 is removably attached to a first arm 1132 of the insertion instrument 1130. Thus, during implantation, the first arm, which retains one of the first or the second attachment sides 140, 142, is used to place the one side of the device against the spinous processes via an approximate lateral insertion angle, after which the second arm 1134, which retains the other attachment side, is attached to the first arm and pivots to place the other attachment side against the opposite side of the respective spinous processes, also laterally from the opposite side. Thus, an insertion instrument 1130 according to this embodiment reduces the size of the incision by allowing positioning one attachment side first using a separated first arm 1132. Otherwise, if the two arms 1132, 1134 are attached prior to implant, the insertion instrument 1130 has to open almost twice as wide to permit inserting both attachment sides laterally while the spinous ligament is still intact.

FIGS. 13-16 show an example surgical instrument system for implanting an interspinous process spacing device, having a first arm 1132 having a proximal end, an elongated central portion and distal end. The distal end has an interspinous process spacing device engagement element 1162 for posteriorly engaging a spacer plate or first attachment side 140 of the interspinous process spacing device having a spacer tray 150 extending inwardly therefrom. The surgical instrument system has a second arm 1132 having a proximal end, an elongated central portion and distal end, wherein the distal end has an interspinous process spacing device engagement element 1164 for posteriorly engaging a locking plate or second attachment side 1142 of the interspinous process spacing device having a spacer tray slot 135 therein for receiving the spacer tray 150.

The surgical instrument system has a means for positioning the first arm 1132 and the second arm 1134 in alignment for securing the interspinous process spacing device onto spinal processes. As discussed in more detail below, the means for positioning the first arm 1132 and the second arm 1134 in alignment can be along any portion of the arms 1132, 1134, including at a hinge in the central portion or by a connecting member at the proximal portion, such as a latch or ratchet. As can be seen in this embodiment, the proximal and distal ends of the arms 1132, 1134 are offset to provide an unobstructed view of the distal ends when a surgeon is holding the proximal ends.

In the illustrated embodiment of the surgical instrument system for implanting an interspinous process spacing device, each arm 1132, 1134 has an interspinous process spacing device engagement element 1162, 1164 which has an engagement projection 1170, 1180 which releaseably engages an instrument receptacle on the attachment side 140, 142 respectively, of the interspinous process spacing device, a mount 1172, 1182 for movably holding the engagement projection, and an implant guide 1174, 1184 extending distally which engages the outer surface of the attachment sides of the interspinous process spacing device.

As shown in FIGS. 13-16, the engagement projections 1170, 1180 are threaded screws which rotatably ride in the mount 1172, 1182 for engagement with the separate attachment sides 140, 142 of the interspinous process spacing device. The threaded projections are controlled by thumbscrews 192, 194, which can also be remotely operated by a ratchet or other rotatable tool.

In the illustrated embodiment, each arm 1132, 1134 permits at least one of an engaged attachment side 140, 142 of the interspinous process spacing device at least 5 degrees, or at least 10 degrees, and up to 30 degrees, of rotation about an axis defined by the engagement element 1174, 1184 on the distal end of the arm 1132, 1134. This permitted wobble of each or both of the attachment sides allows for implanting the device onto spinous processes with varying shapes and contours prior to securing the desired relative orientation by engaging the securing means 320 (e.g., a set screw) onto the spacer tray 150.

In the illustrated embodiment, the engagement projection 1180 on the second arm 1134 provides access to the securing means on the second attachment side 142 of the interspinous process spacing device to secure the second side 142 to the first side 142. In the embodiment shown, the engagement projection 1180 includes a threaded screw which engages a reciprocal threaded instrument receptacle on the attachment side 142 of the interspinous process spacing device. However, the threaded screw on the second arm 1134 is cannulated to provide access therethrough to the securing means on the second attachment side 142 of the interspinous process spacing device to secure the second side 142 to the first side 140 while the second side 142 is engaged to the second arm 1134. The cannulation permits a surgeon to use a separate securing instrument extending through the engagement element 1164 to secure the implantable device onto a spinous process.

In certain embodiments of the surgical instrument system for implanting an interspinous process spacing device, the size, shape or indicia on each of the insertion instrument receptacle on the first attachment side is different from the size, shape or indicia of the insertion instrument receptacle on the second attachment side. In a coordinated manner, the size, shape or indicia on the device engagement element 1162 corresponds to that of the first attachment side 140, and is different from the size, shape or indicia on the device engagement element 1164 which corresponds to that of the second attachment side 142. As shown the engagement element 1162 has a single laser etch mark to match the second attachment side 142, and the engagement element 1164 has a double laser etch mark to match the first attachment side 140.

In the illustrated embodiment, the proximal ends of the first and second arms 1132, 1134 are releasably connectable at more than one selected distance. In particular, the central portions of the first and second arms 1132, 1134 are releasably and rotatably connectable. In such embodiments, the second arm 1134 is removably and pivotally attachable to the first arm 1132 about an axis for positioning the first arm 1132 and the second arm 1134 in alignment for securing the interspinous process spacing device onto spinal processes.

As shown, the second arm 1134 further comprises a pivot member or pin 1137 located on the central portion, and the first arm 1134 further comprises a pivot channel or slot 1135 with a proximally oriented opening and a distally oriented curved retaining edge 1136, such when the pin 1137 is slideably engaged in the slot 1135 against the retaining edge 1136 the first and second arms 1132, 1134 are removeably and pivotally attached to form a hinge, wherein the hinge permits positioning the first arm 1132 and the second arm 1134 in alignment for securing the interspinous process spacing device onto spinal processes.

In use, when the first and second arms 1132, 1134 each have a respective first and second attachment side 140, 142 of the interspinous process spacing device engaged thereto, and the first and second arms 1132, 1134 are attached at the hinge, drawing the proximal ends of the arms together will align and insert the spacer tray 150 into the spacer tray slot 210 of the first and second attachment sides 140, 142 of the interspinous process spacing device, for securing the interspinous process spacing device onto spinal processes.

As shown in FIGS. 13-16, the first arm 1132 further comprises a releasable locking mechanism for selectively securing the pin 1137 of the second arm 1164 into the slot 1135 of the first arm 1132. In certain embodiments, the releasable locking mechanism is a leaf spring 1139 on the central portion of the first arm 1132 in blocking communication with the slot 1135, such that the pin 1137 on the second arm 1164 can deflect the leaf spring 1139 during insertion into the slot 1135 and remain therein when the leaf spring 1139 returns to blocking communication to maintain the pin 1137 against the retaining edge 1136 on the first arm 1132, and wherein the leaf spring 1139 can be manually disengaged from blocking communication with the slot 1135 to release the pin 1137 and separate the first and second arms 1132, 1134.

As illustrated, the surgical instrument system for implanting an interspinous process spacing device has a means for mechanically actuating the insertion instrument to close and open the first arm 1132 and the second arm 1134 for tightening the second attachment side 142 relative to the first attachment side 140. In certain embodiments, the means for mechanically actuating is a ratchet bar 1190 pivotally mounted to the proximal end of the second arm 1134 and selectively engageable to the proximal end of the first arm 1132, wherein the ratchet bar 1190 has a plurality of teeth 1195 on the proximal surface thereof which engage a corresponding flange 1296 on the proximal end of the first arm 1132. The ratchet bar 1190 has a threaded track and a nut 1192 riding thereon outside the proximal end of the first arm for mechanically forcing the proximal ends of the arms 1132, 1134 together.

According to the embodiment of FIGS. 13-16, the first arm 1132 may include a pivot channel 1135 which is at least partially open to receive and retain a pivoting member 1137 extending from the second arm 1134. Although an angled pivot channel 1135 is illustrated, the pivot channel 1135 may be embodied in any number of other various shapes, configurations, and/or dimensions that allow removably attaching and securing the second arm 1134 to the first arm 1132 and that allow the two to pivot relative to each other. To attach the second arm 1134 to the first arm 1132 after one attachment side has been inserted into the patient, the pivoting member 1137 of the second arm 1134 is inserted into and guided through the pivot channel 1135 and rests at the distal end of the pivot channel 1135 where it is secured but allowed to pivot (e.g., similar to separable shears). Therefore, only the second arm 1134 is pivoted toward the first arm 1132 to insert the other attachment side, while the first arm 1132 remains stationary.

With reference to FIGS. 17-20, the present invention further provides an embodiment of a surgical instrument system for implanting an interspinous process spacing device, comprising a first arm 1232 having a proximal end, an elongated central portion and distal end, wherein the distal end has an interspinous process spacing device engagement element 1262 for posteriorly engaging a spacer plate or first attachment side 140 of the interspinous process spacing device having a spacer tray 150 extending inwardly therefrom. Such an embodiment also has a second arm 1234 having a proximal end, an elongated central portion and distal end, wherein the distal end has an interspinous process spacing device engagement element 1264 for posteriorly engaging a locking plate or second attachment side 142 of the interspinous process spacing device having a spacer tray slot 210 therein for receiving the spacer tray 150. This embodiment further includes a compressor tool 1200 for positioning the first arm 1232 and the second arm 1234 in alignment for securing the interspinous process spacing device onto spinal processes.

As illustrated, the compressor tool 1200 has a proximal handle end a central portion and a distal pair of opposing tangs 1222, 1224 moveable throughout a range between an open position and a compression position. In certain embodiments, the distal end of each arm 1232, 1234 comprises compressor tool guide channels 1242, 1244 and compression point indentations 1246, 1248 therein for receiving the compressor tool tangs 1222, 1224. In certain embodiments, the tangs 1222, 1224 have distal compressor tips 1252, 1254 extending inwardly for engagement within the corresponding guide channels 1242, 1244 and compression point indentations 1246, 1248 on the arms 1232, 1234, wherein the compression tool 1200 can rotate about an axis defined by the compressor tips 1252, 1254 so as to provide a user with a range of approach angles for compressing the arms 1232, 1234 to secure the aligned interspinous process spacing device onto spinal processes.

In the illustrated embodiment of the surgical instrument system for implanting an interspinous process spacing device, the proximal end of the second arm 1234 further comprises a retaining latch 1280 disposable on the distal end of the first arm 1232 to retain the arms in position relative to each other and in alignment for securing the interspinous process spacing device onto spinal processes. The latch 1280 can have a series of corresponding indentations for engagement on the first arm 1232.

In certain embodiments, the surgical instrument system for implanting an interspinous process spacing device has a means for mechanically actuating the insertion instrument to close and open the first arm 1232 and the second arm 1234 for tightening the second attachment side 142 relative to the first attachment side 140. As shown, the means for mechanically actuating is a ratchet bar 1290 pivotally mounted to the proximal end of the second arm 1234 and selectively engageable to the proximal end of the first arm 1232, wherein the ratchet bar 1290 has a plurality of teeth 1295 on the proximal surface thereof which engage a corresponding flange 1296 on the proximal end of the first arm 1232. The ratchet bar 1290 has a threaded track and a nut 1292 riding thereon outside the proximal end of the first arm 1232 for mechanically forcing the proximal ends of the arms 1232, 1234 together.

The insertion instrument can further include a flattened surface at or near the pivot point of the instrument. The flattened surface is adapted for striking with a mallet or tamp during insertion of the device to seat each attachment side. It is appreciated that, while the flattened surface can be integrated with the first arm of the insertion instrument, in other embodiments, a flattened surface may be integrated with another portion of the insertion instrument; however, it may be desirable to orient the flattened surface substantially above the device when implanted.

Moreover, according to alternative embodiments, the insertion instrument can further include one or more channels or partial channels (e.g., C- or U-shaped channels, etc.) formed in at least one of the arms through or alongside of which a tightening instrument (e.g., a screwdriver) can be inserted to operate the securing means. For example, according to one embodiment, the first arm includes a channel running at least partially along the length of the first arm. The orientation of the channel directs the tightening instrument through the channel to align with the securing means. For example, if the securing means includes a screw or other rotating mechanism, the insertion instrument can be configured such that when aligned with and attached to the interspinous process spacing device, the first channel aligns with the head of the screw or other rotating mechanism. In other embodiments, one or more additional channels may be formed in an arm of the insertion instrument, such that the additional channel or channels align with a set screw used to fix the position of the second attachment side relative to the first attachment side. In yet another embodiment, a rotating channel, which may be formed as a sleeve that rotates around the axis of the first arm, and indexed to stop at the desired orientations, is used to align with both the securing means and the set screw. In other embodiments, a single channel may be used to align a tightening instrument by re-positioning the arm of the insertion instrument to achieve the desired alignment.

As shown in FIGS. 13-16, the distal portion of each of the arms 1132, 1134 of the insertion instrument 1130 further includes a retaining means 1162, 1164, respectively, for grasping or otherwise retaining the respective attachment side during implantation. In one embodiment, the retaining means on the first arm 1132 includes a first peg having a non-circular cross-sectional shape, such that it is insertable into a correspondingly shaped orifice formed in the respective attachment side (e.g., the second attachment side 142) and provides a friction fit for retaining the attachment side to the first arm 1132. The non-circular shape prevents the attachment side from rotating on the first arm 1132 during implantation. In this embodiment, the retaining means on the second arm 1134 may include a second peg or pin having a circular cross-sectional shape, which is also insertable into a correspondingly shaped orifice formed in the respective attachment side (e.g., the first attachment side 140). Thus, during implantation, while the second attachment side 142 is in a fixed orientation when retained by the insertion instrument 1130, the first attachment side 140 can rotate, which allows for easier alignment of the spacer tray extending from the first attachment side 140 into the slot of the second attachment side 142 and alignment of the securing means (e.g., threaded member) extending from the second attachment side into the receiving means (e.g., floating nut or hemispherical nut) of the first attachment side. In some embodiments, the floating, rotating, and/or pivoting behavior of the receiving means (e.g., floating nut or hemispherical nut) and the advantageously shaped interior surfaces (e.g., a concave shape, etc.) improve the ability to align the spacer tray and/or securing means while bringing the two sides together. It is appreciated that any other means for retaining attachment sides by the insertion instrument 1130 may be included, such as, but not limited to, one or more clips, brackets, clamps, releasable straps, and the like. For example, in another embodiment, the distal ends of each arm 1132, 1134 may be formed in a C-shaped or bracket-shaped clamp, within which a respective attachment side is retained.

It is appreciated that the insertion instrument configurations described herein are provided for illustrative purposes, and that any other configuration and any other orientation relative to the interspinous process spacing device may be used. For example, according to one embodiment, tightening or clamping means similar to any of the securing means described, or any variation thereof, may be integrated with an insertion instrument and between the two arms. In this embodiment, after positioning an interspinous process spacing device to a patient's spinous processes, the tightening or clamping means may be used to tighten the device and secure it to the spinous processes, while other securing means on the device (e.g., those described, or simpler means, such as a set screw, ratchet, pin, screw, etc.) can be used to retain the device in its secured position. It is appreciated that, in some embodiments, clamping or tightening means integrated with a clamping instrument may differ from those described, and may include one or more screws, one or more ratchets, one or more levers, one or more geared mechanisms, and the like.

In addition, it may be advantageous to provide two different insertion instruments, one configured for an interspinous process spacing device being implanted in one orientation and the other configured for an interspinous process spacing device being implanted in the opposite orientation. According to some embodiments, as described herein, at least one arm of an insertion instrument may include features specifically designed to interface with a particular attachment side (e.g., the first retaining means 1162 configured specifically for retaining the second attachment side 142 and the second retaining means 1164 configured for retaining the first attachment side 140, or the channel 1140 oriented to align with the worm gear screw of the securing means, etc.). Thus, without reconfiguring the orientation of these features and without changing the orientation of the handles, a physician would have to change sides of the patient when implanting devices having opposite orientations, which is very impractical and highly undesirable. For example, the screw driving the worm gear in the first and second interspinous process spacing devices are on one side, while the screw of the third interspinous process spacing device is on the opposite side. Accordingly, to prevent the physician from having to switch patient sides during implantation, a second insertion instrument can be formed as essentially the mirror image of the insertion instrument illustrated and described, such that the handles would be operated from approximately the same angle, but the features of the insertion instrument operably align with the device as designed.

However, in another embodiment, a universal insertion instrument may be provided, such that the retaining means extending from the distal ends of each arm of the instrument is configured to have substantially the same shape and orientation. Thus, the retaining means will integrate with either attachment side of an interspinous process spacing device, regardless of the device's orientation. For example, one way to achieve this universal fitment of the insertion instrument is with two pins extending from the distal ends of each attachment arm, the pins being configured the same on each arm. The first attachment side (e.g., the side that does not include the securing means, such as with a floating nut or other receiving member) can be configured with a complementary orifice for receiving one of the two pins while the other pin does not engage or interfere with the first attachment side. The second attachment side, however, can be configured with two complementary orifices such that the two pins are insertable into the two orifices. When installing the second attachment side, both pins are inserted therein, and when installing the first attachment side, only one pin is inserted while the other pin hangs free of the first attachment side. Thus, the operator need not switch between insertion instruments depending upon the orientation of the interspinous process spacing device being implanted.

Figure 21A:
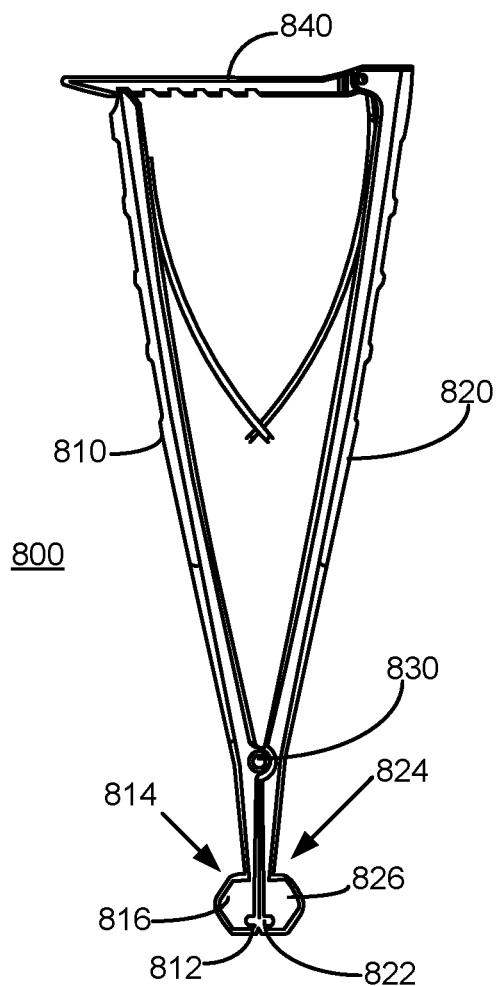
FIG. 21A is a side view of an interspinous process space measurement instrument, according to an example embodiment.
Figure 21B:
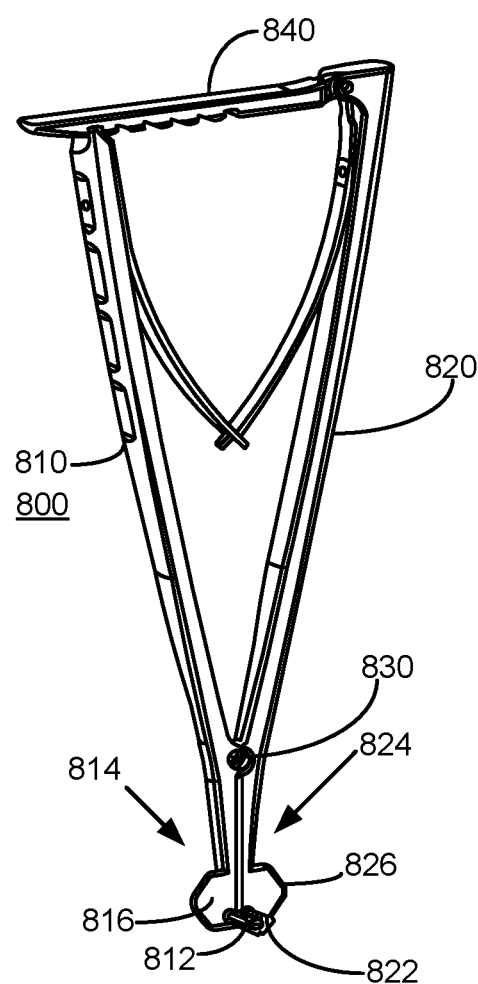
FIG. 21B is an isometric view of an interspinous process space measurement instrument, according to an example embodiment.

The present invention also provides a surgical instrument for selecting an interspinous process spacing device, as exemplified in FIGS. 21A-21B. The selection instrument 800 comprises a first arm 810 having a proximal end, an elongated central portion and distal end, wherein the distal end has a first interspinous process spacing measurement wing 814 extending therefrom comprising a first spinous process stop element 812 and a perpendicularly extending wing template 816, a second arm 820 having a proximal end, an elongated central portion and distal end, wherein the distal end has a second interspinous process spacing measurement wing 824 extending therefrom comprising a second spinous process stop element 822 and a perpendicular wing template 826. The first and second arms 810, 820 are pivotally attached about an axis 830 for positioning the first and second interspinous process spacing measurement wings 814, 824 to measure space between adjacent spinal processes.

The measurement device 800 can further comprise first and second wing templates 816, 826 adapted to overlap respective first and second adjacent spinal processes to determine space available on each spinous process for engaging an interspinous process implant. The instrument shown is adapted such that the proximal end of the second arm 820 has a measuring element 840 attached thereto with indicia to register length to the proximal end of the first arm 810, wherein said length corresponds to space between adjacent spinal processes as measured by the first and second spinous process stop elements 812, 822. Therefore, drawing the proximal ends of the arms 810, 820 together separates the wings 814, 824 to measure space between adjacent spinal processes. In one embodiment, the first or second wing template, or both, comprises a fastener template extending therefrom adapted to engage with a slot on an attachment side of an interspinous process spacing device previously implanted to determine space and orientation available for overlapping engagement of a link plate onto a base plate.

FIG. 1 illustrates further detail of a top perspective view of embodiments of interspinous process spacing devices implanted in an overlapping fashion. FIG. 1 shows a first interspinous process spacing device 130 having substantially flat attachment sides 140, 142, which is illustrated in FIG. 1 as being the one inferiorly located device, such as any of the interspinous process spacing devices illustrated in and described with reference to FIGS. 2-12. In addition, according to some embodiments of the invention, a second (and subsequent) interspinous process spacing device 132 is implanted on adjacent spinous processes, which includes attachment sides 144, 146 having a bent configuration. According to one embodiment, the bent configuration is created by having a substantially flat end 148, which, when implanted, will lie along approximately the same plane as the entire attachment side of the adjacent inferior interspinous process spacing device (e.g., the attachment sides 140, 142 of the first interspinous process spacing device 130 per FIG. 1), and an offset end 149, which will overlap the adjacent end of the inferior (or superior, though not illustrated in this manner) interspinous process spacing device. The offset of the offset end 149 can be approximately equal to, or slightly larger or smaller than, the thickness of the anticipated adjacent attachment side (e.g., the thickness of an attachment side 140, 142 of the first interspinous process spacing device 130).

Accordingly, at least one end of each attachment sides 140, 142 of the first interspinous process spacing device 130 and the offset end 149 of the second interspinous process spacing device 132 includes an integration means for integrating an offset end 149 of the second interspinous process spacing device 132 with a respective attachment side of the first interspinous process spacing device. The embodiment includes an integration means having one or more apertures 240 formed in the outer surface to receive at least a portion of fasteners 220 extending from the inner surfaces of the offset ends 149 of the respective attachment sides 144, 146. The fasteners 220 of the offset ends extending through the apertures 240 can be interlocking posts or be extended sharpened bone fasteners, such as spikes, for engaging a spinous process through the aperture. The apertures 240 permit the attachment sides 144, 146 of the second interspinous process spacing device 132 to integrate and interlock with the attachment sides 140, 142 of the first interspinous process spacing device 130.

According to one embodiment, the number of apertures 240 in the first interspinous process spacing device 130 equals the number of fasteners 220 extending from the second interspinous process spacing device 132. However, in other embodiments, there may be more apertures 240 than fasteners 220 to allow for selective adjustment of the relative orientation of the two interspinous process spacing devices 130, 132 by selecting from multiple positions created by the various aperture locations 240. Apertures may be provided in an overlapping or inch worm pattern for finer adjustments of spacing and angles between each pair of spacing plates. Moreover, in one embodiment, the apertures 240 and corresponding fasteners 220 may have a turning/locking configuration, such that the fasteners 220 can selectively lock (e.g., by turning, snapping, etc.) within the apertures 240 when in position. In addition, the apertures 240 may be sized and shaped larger than the diameter of the corresponding fasteners 220, to permit adjusting the position and orientation of the second interspinous process spacing device 132 relative to the already secured first interspinous process spacing device 130. In other embodiments, however, the apertures 240 may be any configuration. Moreover, in one embodiment, slots may not be provided, and the offset ends 149 of the attachment sides 144, 146 may not include fasteners, but instead may include a rough surface, or other suitable means to secure the two attachment sides. Although only a first and a second interspinous process spacing devices 130, 132, in other embodiments additional interspinous process spacing devices may be added to the second interspinous process spacing device 132 in a similar manner to connect additional spinous processes. Each subsequent interspinous process spacing device would be configured similar to the second interspinous process spacing device 132, including offset ends 149 to overlap with the flat ends 148 of the adjacent interspinous process spacing device. To permit adding another interspinous process spacing device to the second interspinous process spacing device 132, the outer surfaces of the flat ends 148 of the attachment sides 144, 146 also include apertures 240 to receive fasteners, like those shown on the first interspinous process spacing device 130, or any other integration means. Any number of interspinous process spacing devices can be integrated together, permitting fusing a number of spinous processes and providing increased structural integrity over individually and un-integrated known spinous process spacing devices.

For example, in one embodiment in which three interspinous process spacing devices are attached. In this embodiment, the first interspinous process spacing device has substantially flat attachment sides, and the second and third interspinous process spacing devices have bent attachment sides with offset ends for overlapping adjacent devices. In this embodiment, the first interspinous process spacing device is implanted, after which the second and third interspinous process spacing devices are implanted such that each overlaps with a different end of the first interspinous process spacing device (e.g., one implanted superior to and the other implanted inferior to the first interspinous process spacing device). As shown, the second and third interspinous process spacing devices are oriented 180 degrees relative to each other to allow the offset ends of the bent attachment sides to overlap the attachment sides of the first interspinous process spacing device, depending upon whether being attached superior to or inferior to the first interspinous process spacing device. Thus, rotating the subsequent interspinous process spacing devices, if necessary, avoids having to manufacture two different interspinous process spacing device configurations—one for attaching superior to a flat device and one for attaching inferior to a flat device. Because the location of the securing means may differ when an interspinous process spacing device is rotated, different insertion instruments may be provided to accommodate the differing orientations of the device components.

In another embodiment, in which a stub implant is provided, instead of a first interspinous process spacing device. The stub implant simply consists of two stub sides proportioned to engage a single spinous process, and not intended to span two adjacent spinous processes. Accordingly, instead of attaching a second interspinous process spacing device to a first device, it is attached to a stub implant. In operation, the second interspinous process spacing device and the stub implant are likely implanted together, as the two stub sides are secured by the pressure exerted by the second interspinous process spacing device. Like the other interspinous process spacing devices, the stub sides can also include fasteners extending from their inner surfaces for securing to the spinous process, and apertures formed in their outer surfaces for receiving fasteners of the overlapping interspinous process spacing device, or any other integration means. This embodiment may serve to reduce the manufacturing costs, requiring only a single design for the interspinous process spacing device, and smaller, much simpler design for the stub implant.

FIGS. 7A-7E illustrate other example embodiments of an interspinous process spacing device that is configured for implanting at the L5-S1 vertebrae. As shown, an L5-S1 interspinous process spacing device 530 includes first and second attachment sides 540, 542, each having an angled end 545 and an opposite flat end 547 with various spiked bone fasteners 525 extending inwardly. The angled ends 545 allow better fit with the anatomy of a patient's sacrum. In certain embodiments not shown, the angled ends may be further adjustable with respect to the central portion of the device to match the angle on the patient's sacrum. The L5-S1 interspinous process spacing device 530 may include any securing means, such as are illustrated in and described herein, and any integration means. Moreover, in a base plate embodiment such as that illustrated in FIGS. 7A-7C with apertures 550 in the flat end 547, an additional interspinous process spacing link device can be implanted superior to the L5-S1 interspinous process spacing device 530 in an overlapping configuration by overlapping bent attachment sides of the superior interspinous process spacing device with the flat ends 547 of the L5-S1 interspinous process spacing device 530. However, in a link plate embodiment such as that illustrated in FIGS. 7D-7E, with fasteners 520 on an offset flat end 547, the L5-S1 interspinous process spacing device 530 has bent attachment sides such that the ends opposite the angled ends 545 are offset and overlap flat ends of a superior interspinous process spacing device. In certain embodiments, the bone fasteners 525 extend from opposing plates toward the bone at different opposing points to reduce the risk of bone fracture.

Figure 7A:
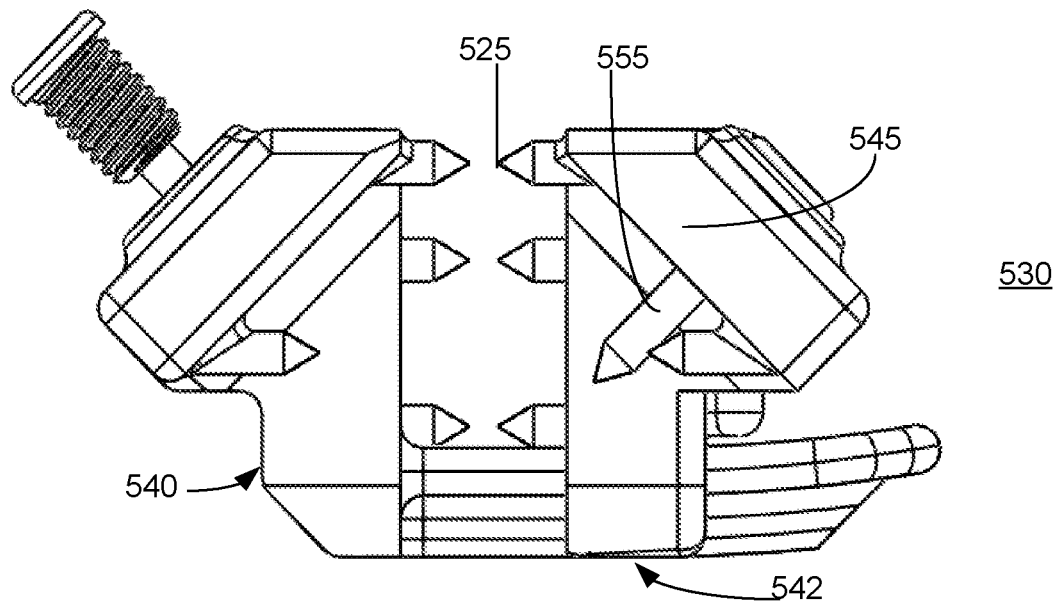
FIG. 7A is a side view of a L5-S1 sacrum interspinous process spacing base device, according to an example embodiment.
Figure 7B:
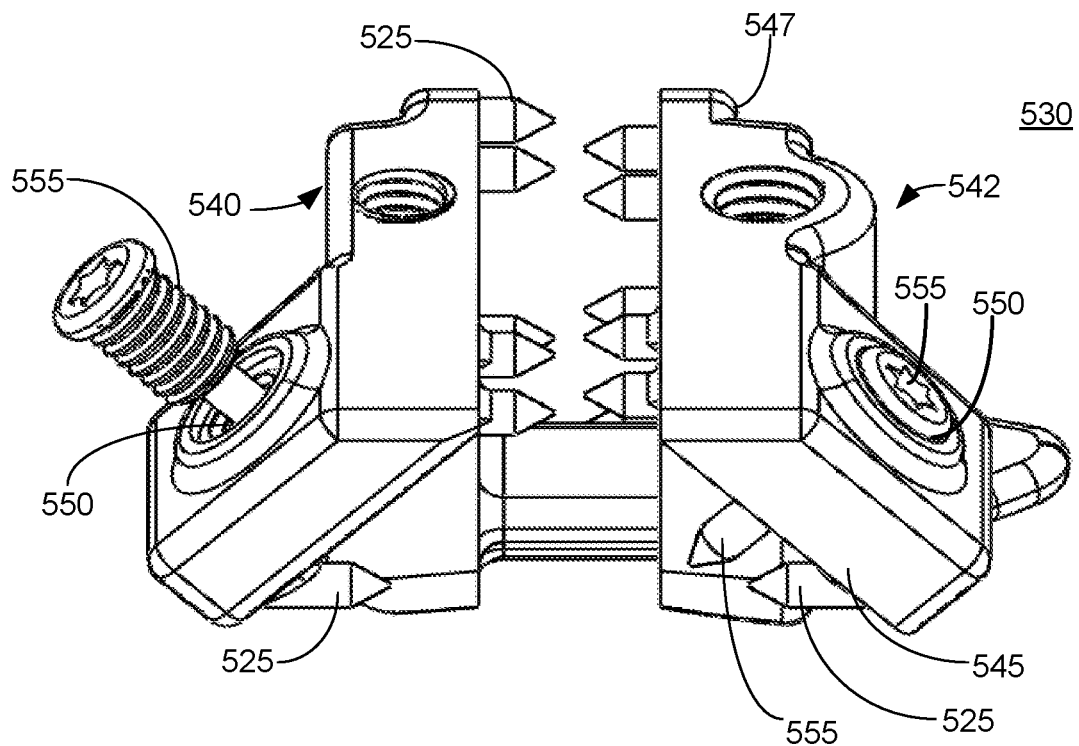
FIG. 7B is an isometric view of a L5-S1 sacrum interspinous process spacing base device, according to an example embodiment.
Figure 7C:
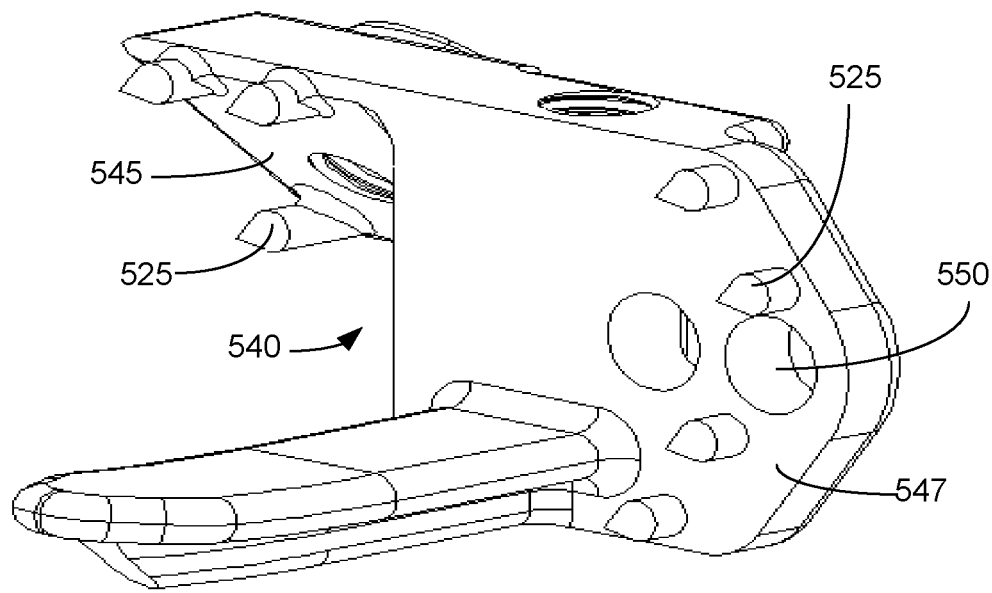
FIG. 7C is an isometric view of a first attachment side of an L5-S1 sacrum interspinous process spacing base device, according to an example embodiment.
Figure 7D:
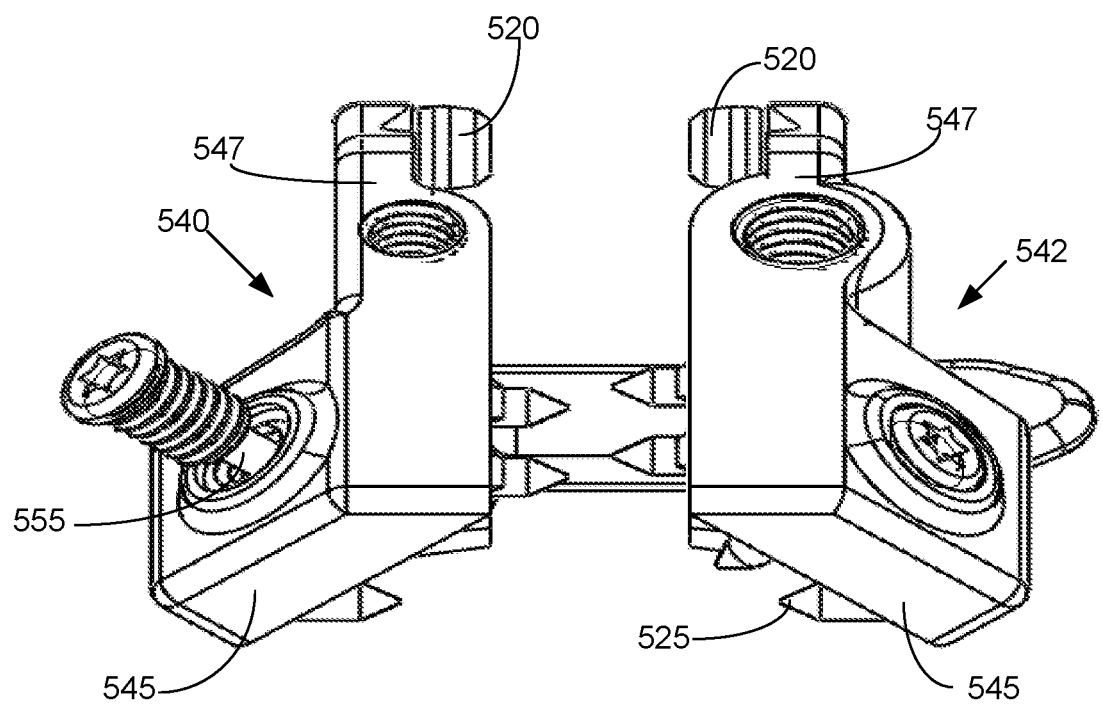
FIG. 7D is an isometric view of an alternative L5-S1 sacrum interspinous process spacing link device, according to an example embodiment.
Figure 7E:
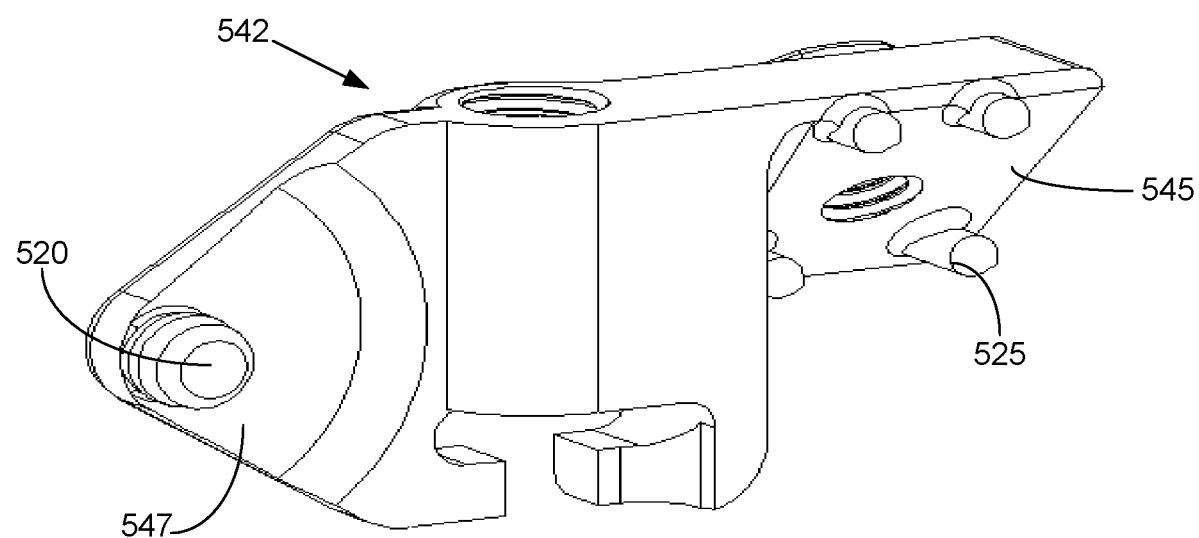
FIG. 7E is an isometric view of a second attachment side of a L5-S1 sacrum interspinous process spacing link device, according to an example embodiment.

FIG. 7B illustrates a view of a second attachment side 542 of an L5-S1 interspinous process spacing device 530. As shown, the angled end 545 of the second attachment side 542 may optionally include one or more apertures 550 for receiving one or more fastening means therethrough. Because the sacrum is typically more dense than spinous processes, one means to secure an L5-S1 interspinous process spacing device 530 to the sacrum includes fastening directly thereto through the one or more apertures 550, such as via screws, set screws, and the like. In particular, an angled fastener 555 can be provided at an angle different from the angle at which other fasteners 525 extend. In some embodiments such as shown, the angled fastener 555 is a bone screw and the other bone fasteners 525 are bone spikes, although any combination of movable, immovable, or expandable bone fasteners can be used.

FIG. 7A illustrates a side view of the interior surface of a second attachment side 542 of a L5-S1 interspinous process spacing device 530. In this embodiment, one or more fasteners 525, similar to the fasteners 225 described with reference to FIG. 2A, extend from the interior of the angled end 545 of the L5-S1 interspinous process spacing device 530. However, because of the orientation of the angled end 545 relative to the patient's sacrum, the fasteners 525 may extend at an angle other than 90 degrees (either acute or obtuse), such that they correctly engage the sacrum when tightening the two attachment sides together. It is appreciated that the second attachment side 542 is described and illustrated in detail by example, but that the first attachment side 540 may also include one or more apertures and one or more fasteners.

The integration means of certain embodiments includes a textured inner surface formed on the inner surface of the offset end and a textured outer surface formed on the outer surface of an adjacent flat end (on the same interspinous process spacing device or understood that the offset end of one interspinous process spacing device will overlap a portion of the flat end of an adjacent interspinous process spacing device). According to one embodiment, the textured inner surface has radially extending ridges arranged in a starburst or spoked pattern. Similarly, the textured outer surface can have one or more detents or nubs (or other surface patterns) approximately matching the radially extending pattern of the textured inner surface. The textured outer surface has multiple complementary detents to permit selective arrangement of the offset end in more than one position. It is appreciated that, while a radially extending pattern is described, any other textured surface may be applied to the inner and outer textured surfaces.

Moreover, according to one embodiment, the inner surface of the offset end may further include a pin extending inwardly, which can be at least partially inserted into one or more apertures formed in the outer surface of the flat end of the adjacent interspinous process spacing device. The pin can be positioned approximately in the center of the radially extending ridges and three apertures are formed in the flat end approximately in the center of the corresponding radial detents. It is appreciated that any number of pins and any number of apertures may be provided. Moreover, any other orientation of the pins and/or the apertures may be used. For example, according to another embodiment, the apertures may be formed in two dimensions to allow for both anterior/posterior and superior/inferior adjustment.

The interspinous process spacing devices and any associated components may be made of any suitable biocompatible material, including, but not limited to, metals, resorbable ceramics, non-resorbable ceramics, resorbable polymers, non-resorbable polymers, and/or any combination and/or alloys thereof. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluropolymers, and/or other suitable biocompatible materials and/or combinations thereof.

In use, an example method of implanting at least two interspinous process spacing devices can be understood with reference to FIGS. 1-21. In one embodiment, after gaining access to the surgical implantation site, and removing all necessary tissue, the second attachment side 142 of a first interspinous process spacing device 130 is attached to a securing means 1162 of the first arm 1132 of an insertion instrument 1130 prior to attaching the second arm 1134 to the insertion instrument 1130. The first arm 1132 is used to position the second attachment side 142 against one side of two adjacent spinous processes. Because of the reduced profile of the securing means, such as the threaded member 451 used in a worm gear securing means, the second attachment side 142 may be more easily inserted from a lateral direction through ligaments existing between the two spinous processes (although, the device may also be inserted by removing all or a substantial portion of the ligaments and inserted directly from the posterior direction). The second attachment side 142 may further be seated by striking a flattened surface of the insertion instrument 1130 with a mallet or tamp. The first attachment side is then attached to the securing means 1164 of the second arm 1134 of the insertion instrument 1130, and the second arm 1134 is pivotally attached to the first arm 1132. The physician then squeezes the handles of the insertion instrument 1130 to pivot the first attachment side 140 in place against the opposite side of the same two spinous processes, inserting the spacer tray 150 through the ligaments and aligning with its tray slot 210 on the second attachment side 142, while also operably aligning the securing means extending from the second attachment side 142 with the corresponding receiving member on the first attachment side 140. In one embodiment, a punch instrument may first be used prior to inserting either or both of the first and second attachment sides, 140, 142 to remove a portion of the ligaments to facilitate insertion and alignment of the attachment sides 140, 142. The punch instrument may operate in a manner similar to the insertion instrument 1130, but include a punch (or may simply dilate) that laterally passes through and removes the ligaments when the handles are squeezed together. The two attachment sides 140, 142 are pushed together enough to engage the securing means (e.g., worm screws meshing with the worm gearing, screws through a threaded collar, or shaft and gear meshing with the gearing/rack, etc.). Then, to tighten the attachment sides 140, 142 relative to each other, the operator can operate the securing means (e.g., turn the screw to operate the worm drive mechanism). Because of the ability of each attachment side 140, 142 to pivot relative to the other, the interspinous process spacing device 130 can be tightened against the spinous processes, irrespective of the possible varied thicknesses of each spinous process. Once in a tightened configuration, a set screw assembly may optionally be set to secure the second attachment end 142 to the spacer tray 150. It is appreciated that other insertion instrument embodiments may be used to position and implant an interspinous process spacing device, such as one in which a securing means (e.g., gearing, worm gear, screw, ratchet, etc.) is integrated as part of the insertion instrument, instead of, or in addition to, being integrated with the interspinous process spacing device. Thus, in this embodiment, the tightening can at least partially be achieved by operating securing means of the insertion instrument instead of on the device to both tighten and loosen the insertion instrument.

To implant a second (or subsequent) interspinous process spacing device 132, the same steps are repeated with the exception of aligning the integration means (e.g., fasteners, apertures, domes, pins, etc.) on the inner surfaces of the offset ends 149 (or a straight member) with the outer surfaces of the respective attachment ends of the adjacent interspinous process spacing device 130.

Modifications and variations of the devices and methods described herein will be obvious to those skilled in the art from the foregoing detailed description. Such modifications and variations are intended to come within the scope of the appended claims and the example inventions described herein.

What is claimed is:

1. An interspinous process spacing device, comprising:
a first attachment side;
a second attachment side; and
a spacer extending from the first attachment side and slideably insertable through a spacer aperture formed in the second attachment side, the spacer adapted to be positioned between a spinous process of a first vertebra and a spinous process of an adjacent second vertebra;
wherein the first attachment side and the second attachment side each comprise:
a central portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the central portion;

a first wing portion integrally formed with and extending from the central portion, the first wing portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the first wing portion;

a second wing portion integrally formed with and extending from the central portion, the second wing portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the second wing portion;

a first bone fastener extending inwardly from the inner surface of the first wing portion at a first fixed angle; and a second bone fastener extending inwardly from the inner surface of the second wing portion at a second fixed angle;

wherein the inner surface of the first wing portion extends in a direction transverse to the inner surface of the central portion;

wherein the anterior-posterior height of the first wing portion is less than the anterior-posterior height of the central portion;

wherein the inner surface of the first wing portion is not coplanar with the inner surface of the second wing portion;

wherein the inner surface of the central portion and the inner surface of the first wing portion each have a planar shape, and wherein the inner surface of the first wing portion is angled relative to the inner surface of the central portion to define a predefined acute angle between the inner surface of the first wing portion and the inner surface of the central portion.

2. The device of claim 1, wherein the posterior surface of the first wing portion is coplanar with the posterior surface of the second wing portion.

3. The device of claim 1, wherein the first attachment side and the second attachment side each further comprise:

a third bone fastener extending inwardly from the inner surface of the first wing portion at a third fixed angle; and a fourth bone fastener extending inwardly from the inner surface of the second wing portion at a fourth fixed angle.

4. The device of claim 3, wherein a longitudinal axis of the third bone fastener extends at a perpendicular angle relative to the inner surface of the central portion.

5. The device of claim 3, wherein a longitudinal axis of the third bone fastener extends parallel to a longitudinal axis of the first bone fastener.

6. The device of claim 3, wherein a distal tip of the first bone fastener and a distal tip of the third bone fastener are spaced apart from one another in a medial-lateral direction.

7. The device of claim 1, wherein a longitudinal axis of the first bone fastener extends at a non-perpendicular angle relative to the inner surface of the first wing portion.

8. The device of claim 1, wherein the longitudinal axis of the first bone fastener extends at a perpendicular angle relative to the inner surface of the central portion.

9. The device of claim 1, wherein a longitudinal axis of the second bone fastener extends at a perpendicular angle relative to the inner surface of the central portion.

10. The device of claim 1, wherein the first wing portion further comprises a second inner surface extending along a minority of the anterior-posterior height of the first wing portion, and wherein the inner surface of the first wing portion extends in a direction transverse to the second inner surface of the first wing portion.

11. The device of claim 10, wherein the second inner surface of the first wing portion has a planar shape, and wherein the inner surface of the first wing portion is angled relative to the second inner surface of the first wing portion to define a predefined acute angle between the inner surface of the first wing portion and the second inner surface of the first wing portion.

12. The device of claim 11, wherein the second inner surface of the first wing portion is coplanar with the inner surface of the central portion.

13. The device of claim 10, wherein a longitudinal axis of the third bone fastener extends at a perpendicular angle relative to the second inner surface of the first wing portion.

14. The device of claim 1, wherein the wherein the second wing portion further comprises a second inner surface extending along a minority of the anterior-posterior height of the second wing portion, and wherein the inner surface of the second wing portion extends in a direction transverse to the second inner surface of the first wing portion.

15. The device of claim 1, wherein the first wing portion and the second wing portion extend in opposite directions from the central portion.

16. The device of claim 1, wherein the anterior-posterior height of the first wing portion is less than the anterior-posterior height of the second wing portion.

17. The device of claim 1, further comprising securing means for securing the second attachment side relative to the first attachment side.

18. An interspinous process spacing device, comprising:
a first attachment side;
a second attachment side; and
a spacer extending from the first attachment side and slideably insertable through a spacer-aperture formed in the second attachment side, the spacer adapted to be positioned between a spinous process of a first vertebra and a spinous process of an adjacent second vertebra;
wherein the first attachment side and the second attachment side each comprise:
a central portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the central portion;

a first wing portion integrally formed with and extending from the central portion, the first wing portion comprising:

an anterior surface adapted to face anteriorly with respect to the first vertebra and the second vertebra;

a posterior surface adapted to face posteriorly with respect to the first vertebra and the second vertebra;

a first inner surface extending along a majority of an anterior-posterior height between the anterior surface and the posterior surface of the first wing portion; and a second inner surface extending along a minority of the anterior-posterior height between the anterior surface and the posterior surface of the first wing portion; and a second wing portion integrally formed with and extending from the central portion, the second wing portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the second wing portion;

wherein the first inner surface of the first wing portion extends in a direction transverse to each of the inner surface of the central portion and the second inner surface of the first wing portion;

wherein the inner surface of the first wing portion is not coplanar with the inner surface of the second wing portion;

wherein the anterior-posterior height of the first wing portion is less than the anterior-posterior height of the central portion;

wherein the inner surface of the central portion and the inner surface of the first wing portion each have a planar shape, and wherein the inner surface of the first wing portion is angled relative to the inner surface of the central portion to define a predefined acute angle between the inner surface of the first wing portion and the inner surface of the central portion.

19. An interspinous process spacing device, comprising:
a first attachment side;
a second attachment side; and
a spacer extending from the first attachment side and slideably insertable through a spacer aperture formed in the second attachment side, the spacer adapted to be positioned between a spinous process of a first vertebra and a spinous process of an adjacent second vertebra;

wherein the first attachment side and the second attachment side each comprise:

a central portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the central portion;

a first wing portion integrally formed with and extending from the central portion, the first wing portion comprising:

an anterior surface adapted to face anteriorly with respect to the first vertebra and the second vertebra;

a posterior surface adapted to face posteriorly with respect to the first vertebra and the second vertebra;

a first inner surface extending along a majority of an anterior-posterior height between the anterior surface and the posterior surface of the first wing portion; and a second inner surface extending along a minority of the anterior-posterior height between the anterior surface and the posterior surface of the first wing portion; and a second wing portion integrally formed with and extending from the central portion, the second wing portion comprising:

an anterior surface adapted to face anteriorly with respect to the first vertebra and the second vertebra;

a posterior surface adapted to face posteriorly with respect to the first vertebra and the second vertebra; and an inner surface extending along at least a majority of an anterior-posterior height between the anterior surface and the posterior surface of the second wing portion;

a first bone fastener extending inwardly from the first inner surface of the first wing portion at a first fixed angle;

a second bone fastener extending inwardly from the inner surface of the second wing portion at a second fixed angle; and a third bone fastener extending inwardly from the first inner surface of the first wing portion at a third fixed angle;

wherein the first inner surface of the first wing portion extends in a direction transverse to each of the inner surface of the central portion and the second inner surface of the first wing portion;

wherein the anterior-posterior height of the first wing portion is less than the anterior-posterior height of the central portion;

wherein a longitudinal axis of the first bone fastener extends parallel to a longitudinal axis of the third bone fastener;

wherein the inner surface of the central portion and the inner surface of the first wing portion each have a planar shape, and wherein the inner surface of the first wing portion is angled relative to the inner surface of the central portion to define a predefined acute angle between the inner surface of the first wing portion and the inner surface of the central portion.

\* \* \* \* \*